United States Patent
Whiteley et al.

(10) Patent No.: US 6,855,513 B1
(45) Date of Patent: Feb. 15, 2005

(54) QUORUM SENSING SIGNALING IN BACTERIA

(75) Inventors: Marvin Whiteley, Coralville, IA (US); Kimberly M. Lee, Iowa City, IA (US); E. Peter Greenberg, Iowa City, IA (US); Ute Muh, Iowa City, IA (US)

(73) Assignees: University of Iowa Research Foundation, Iowa City, IA (US); Vertex Pharmaceuticals (San Diego) LLC, San Diego, CA (US)

( * ) Notice: Subject to any disclaimer, the term of this patent is extended or adjusted under 35 U.S.C. 154(b) by 6 days.

(21) Appl. No.: 09/653,730

(22) Filed: Sep. 1, 2000

Related U.S. Application Data

(60) Provisional application No. 60/153,022, filed on Sep. 3, 1999.

(51) Int. Cl.[7] .......................... C12Q 1/00; C12Q 1/04; G01N 33/53; G01N 33/542; G01N 13/00

(52) U.S. Cl. .................. 435/34; 424/93.3; 424/170; 424/183.1; 435/4; 435/5; 435/7.2; 435/7.32; 435/7.4; 435/7.6; 435/7.8; 435/7.9; 435/29; 435/32; 435/34; 435/35; 435/69.8; 435/91.4; 435/170; 435/173.8; 435/218; 435/220; 435/252.34; 435/253.3; 435/340; 435/440; 435/463; 435/465; 435/480; 435/488; 530/389.5

(58) Field of Search .................. 435/4, 5, 7.2, 7.32, 435/7.4, 7.6, 7.8, 7.9, 29, 32, 34, 35, 69.8, 91.4, 170, 173.8, 218, 220, 340, 252.34, 253.3, 440, 463, 465, 480; 424/93.3, 170, 183.1; 530/389.5

(56) References Cited

U.S. PATENT DOCUMENTS 5,591,872 A    1/1997   Pearson et al.
5,593,827 A    1/1997   Bycroft et al. ................. 435/6

FOREIGN PATENT DOCUMENTS

WO       WO 98/57618 A1    12/1998

OTHER PUBLICATIONS

Latifi et al. 1996. Mol.Micro. 21(6):1137–1146.*
Passador et al. 1993. Science. 260:1127–1130.*
Passador et al. 1996. J. of Bacter. 178(20): 5995–6000.*
Pearson et al. 1994. PNAS. 91:197–201.*
Pearson et al. 1997. J. of bacter. 179(18): 5756–5756.*
Pesci et al. 1997. J. of bacter. 179(10): 3127–3132.*
GenBank Acc. No. AF005404; *Pseudomonas aeruginosa* pyocyanine biosynthesis operon, complete sequence.*
De Kievit, T. et al. Quorum sensing, gene expression, and Pseudomonas biofilms. *Methods Enzymol.* 1999;310–117–28.*
De Kievit, T. et al. RsaL, a novel repressor of virulence gene expression in *Pseudomonas aeruginosa J. Bacteriol.* Apr. 1999;181(7):2175–84.*
Mavrodi, D.V. et al. Functional Analysis of Genes for Biosynthesis of Pyocyanin and Phenazine–1–Carboxamide from *Pseudomonas aeruginosa* PAO1 *J. Bacteriol.* Nov. 2001;183 (21): 6454–6465.*

(List continued on next page.)

*Primary Examiner*—Lynette R. F. Smith
*Assistant Examiner*—J. Hines
(74) *Attorney, Agent, or Firm*—Lahive & Cockfield LLP; DeAnn F. Smith; Lisa M. DiRocco

(57) ABSTRACT

The invention provides methods for identifying a modulator of quorum sensing signaling in bacteria, and for identifying a quorum sensing controlled gene in bacteria. In addition, the invention provides quorum sensing controlled genetic loci in *Pseudomas aeruginosa*. Novel indicator strains and vectors for engineering the strains for use in the method of the invention are also provided.

33 Claims, 13 Drawing Sheets

OTHER PUBLICATIONS

Pierson, L., III et al. Phenazine antibiotic biosynthesis in *Pseudomonas aureofaciens* 30–84 is regulated by PhzR in response to cell density. *J. Bacteriol.* Jul. 1994;176(13):3966–74.*

Adar et al. (1993) "GroESL proteins facilitate binding of externally added inducer by LuxR protein–containing *E. coli* cells," *J Biolumin Chemilumin.* 8(5):261–6.

Baldwin, T.O. et al. (1989) "The complete nucleotide sequence of the lux regulon of *Vibrio fischeri* and the luxABN region of *Photobacterium leiognathi* and the mechanism of control of bacterial bioluminescence," *J. of Biolum. and Chemilum.* 4:326–341.

Brint, J. M. et al. (1995) "Synthesis of multiple exoproducts in *Pseudomonas aeruginosa* is under the control of RhIR–RhII, another set of regulators in strain PAO1 with homology to the autoinducer–responsive LuxR–LuxI family," *J. Bacteriol.* 177:7155–7163.

Britigan, et al. (1999) "The *Pseudomonas aaeruginosa* secretory product pyocyanin inactivates alpha1 protease inhibitor: implications for the pathogenesis of cystic fibrosis lung disease." *Infect Immun.* 67(3):1207–12.

Chapon–Herve, V. et al. (1997) "Regulation of the xcp secretion pathway by multiple quorum–sensing modulons in *Pseudomonas aeruginosa,*" *Mol. Microbiol.* 24:1169–1170.

Cormack, B. P. et al. (1996) "FACS–optimized mutants of the green fluorescent protein (GFP)," *Gene.* 173(1):33–38.

Cunliffe, H. E. et al. (1995) "Cloning and characterization of pvdS, a gene required for pyoverdine synthesis in *Pseudomonas aeruginosa*: PvdS is probably an alternative sigma factor," *J. Bacteriol.* 177: 2744–2750.

Davies, D. G. et al. (1998) "The involvement of cell–to–cell signals in the development of a bacterial biofilm," *Science.* 280(5361):295–8.

Devine, J.H. et al. (1989) "Identification of the operator of the lux regulon from the *Vibrio fischeri* strain ATCC7744," *PNAS* 86: 5688–5692.

Eberhard, A., et al. (1991) "Synthesis of the lux gene autoinducer in *vibrio fischeri* is positively autoregulated," *Arch. of Microbiol.* 155:294–297.

Evans, K., et al. (1998) "Influence of the MexAB–OprM multidrug efflux system on quorum sensing in *Pseudomonas aeruginosa,*" *J. Bacteriol.* 180:5443–5447.

Figurski, D. H. et al. (1979) "Replication of an origin–containing derivative of plasmid RK2 dependent on a plasmid function provided in trans," *Proc. Natl. Acad. Sci. USA* 76: 1648–1652.

Fuqua, et al. (1994) "Quorum sensing in bacteria: the LuxR–LuxI family of cell density–responsive transcriptional regulators," *J Bacteriol.* 176(2):269–75.

Fuqua, W.C. et al. (1996) "Census and consensus in bacterial ecosystems: the LxuR–Luxl family of quorum–sensing transcriptional regulatros," *Annu. Rev. Microbiol.* 50:727–751.

Fuqua, C. et al. (1998) "Self perception in bacteria: quorum sensing with acylated homoserine lactones," *Curr Opin Microbiol.* 1(2):183–189.

Gambello, M. J. et al. (1991) "Cloning and characterization of the *Pseudomonas aeruginosa* lasR gene, a transcriptional activator of elastase expression," *J. Bacteriol.* 173: 3000–3009.

Georgakopoulos, D. G. et al. (1994) "Cloning of a Phenazine Biosynthetic Locus of Pseudomonas Auerofaciens PGS12 and analysis of its expression in vitro with the ice nucleation reporter gene," *Appl. Environ. Microbiol.* 60:2931–2938.

Gray, K.M. et al. (1992) "Physical and functional maps of the luminescence gene cluster in an autoinducer–deficient *Vibrio fischeri* strain isolated from a squid light organ," *J. Bacteriol.* 174:4384–4390.

Hassan, H. M. et al. (1979) "Intracellular production of superoxide radical and of hydrogen peroxide by redox active compounds," *Arch Biochem Biophys.* 196(2):385–95.

Hassan, H. M. et al. (1980) "Mechanism of the antibiotic action pyocyanine," *J Bacteriol.* 141(1):156–63.

Holloway, B. W., et al. (1979) "Chromosomal genetics of *Pseudomonas,*" *Microbiol. Rev.* 43:73–102.

Jamin, M. et al. (1991) "Accumulation of acyl–enzyme in DD–peptidase–catalysed reactions with analogues of peptide substrates," *Biochem J.* 280(Pt 2):499–506.

Hanzelka, B.A. et al. (1995) "Evidence that the N–terminal region of the *Vibrio fischeri* LuxR protein constitutes an autoinducer–binding domain," *J Bacteriol.* 177:815–817.

Hanzelka, B.A. et al. (1996) "Quorum sensing in *Vibrio fischeri*: evidence that S–adenosylmethionine is the amino acid substrate for autoinducer synthesis," *J. Bacteriol.* 178:5291–5294.

Kaplan, H.B. et al. (1985) "Diffusion of autoinducer is involved in regulation of the *Vibrio fischeri* luminescence system," *J. Bacteriol.* 163:1210–1214.

Kohler, T., et al. (1997) "Characterization of MexE–MexF–OprN, a positively regulated multidrug efflux system of *Pseudomonas aeruginosa,*" *Mol. Microbiol.*; 23:345–354.

Latifi, A. et al. (1995) "Multiple homologues of LuxR and LuxI control expression of virulence determinants and secondary metabolites through quorum sensing in *Pseudomonas aeruginosa* PAO1," *Mol. Microbiol. Rev.* 17:333–344.

Latifi, A. et al. (1996) "A hierarchical quorum–sensing cascade in *Pseudomonas aeruginosa* links the transcriptional activators LasR and RhIR (VsmR) to expression of the stationary–phase sigma factor RpoS," *Mol. Microbiol.* 21:1137–1146.

Linn, T. et al. (1990) "Improved vector system for constructing transcriptional fusions that ensures independent translation of IacZ," *J. Bacteriol.* 172:1077–1084.

Mavrodi, D. V. et al. (1998) "A seven–gene locus for synthesis of phenazine–1–carboxylic acid by *Pseudomonas fluorescens* 2–79," *J. Bacteriol.* 180:2541–8.

Miller, V. L. et al. (1988) "A novel suicide vector and its use in construction of insertion mutations: osmoregulation of outer membrane proteins and virulence determinants in *Vibrio cholerae* requires toxR," *J. Bacteriol.* 170:2575–2583.

Moré, M. I. et al. (1996) "Enzymatic synthesis of a quorum–sensing autoinducer through use of defined substrates," *Science.* 272(5268):1655–8.

Ochsner, U.A., et al. (1995) "Autoinducer–mediated regulation of rhamnolipid biosurfactant synthesis in *Pseudomonas aeruginsa,*" *PNAS,* 92:6424–6428.

Parsek, M. R. et al. (1999) "Acyl homoserine–lactone quorum–sensing signal generation," *Proc. Natl. Acad. Sci. USA.* 96:4360–4365.

Passador, L., et al. (1993) "Expression of *Pseudomonas aeruginosa* virulence genes requires cell–to–cell communication," *Science* 260:1127–1130.

Passador, L. et al. (1996) "Functional analysis of the *Pseudomonas aeruginosa* autoinducer PAI," *J Bacteriol.* 178(20):5995–6000.

Pearson, J.P et al. (1994) "Structure of the autoinducer required for expression of Pseudomonas aeruginosa virulence genes," PNAS 91:197–201.

Pearson, J. P., et al. (1997) "Roles of Peudomonas aeruginosa las and rhl quorum–sensing systems in control of elastase and rhamnolipid biosynthesis genes," J. Bacteriol. 179:5756–5767.

Pearson, J. P. et al. (1999) "Active efflux and diffusion are involved in transport of Pseudomonas aeruginosa cell–to–cell signals," J. Bacteriol. 181:1203–1210.

Pesci, E.C. et al. (1997) "Regulation of las and rhl quorum sensing in Pseudomonas aeruginosa," J. Bacteriol. 179:3127–3132.

Pesci, E.C. et al.(1997) "The chain of command in Pseudomonas quorum sensing," Trends in Microbiol. 5(4):132–135.

Poole, K.et al. (1996) "Overexpression of the mexC–mexD–oprJ efflux operon in nfxB–type multidrug–resistant strains of Pseudomonas aeruginosa," Mol. Microbiol. 21:713–724.

Poole, K, et al. (1993) "Multiple antibiotic resistance in Pseudomonas aeruginosa: evidence for involvement of an efflux operon,"J. Bacteriol. 175:7363–7372.

Rombel, I. et al. (1995) "Identification of a DNA sequence motif required for expression of iron–regulated genes in pseudomonads," Mol. Gen. Genet. 246: 519–528.

Ruby, E.G. (1996) "Lessons from a cooperative, bacterial–animal association: the Vibrio fischeri–Euprymna scolopes light organ symbiosis," Ann. Rev. Microbiol. 50:591–624.

Rust, L. et al., (1996) "Analysis of the Pseudomonas aeruginosa elastase (lasB) regulatory region," J. Bacteriol. 178:1134–1140.

Salmond, G.P.C. et al. (1995) "The bacterial 'enigma': cracking the code of cell–cell communication," Mol. Microbiol. 16:615–624.

Schaefer, A. L. et al. (1996) "Genertion of cell–to–cell signals in quorum sensing: acyl homoserine lactone synthase activity of a purified Vibrio fischeri LuxI protein," Proc Natl Acad Sci USA. 93(18):9505–9.

Schaefer, A. L. et al. (1996) "Quorum sensing in Vibrio fischeri: probing autoinducer–LuxR interactions with autoinducer analogs," J Bacteriol. 178(10):2897–901.

Schweizer, H. P. (1993) "Small broad–host–rang gentamycin resistance gene cassettes for site–specific insretion and deletion mutagenesis," Biotechniques 15:831–833.

Seed, et al. (1995) "Activation of the Pseudomonas aeruginosa LasI gene by LasR and the Pseudomonas autoinducer PAI: an autoinduction regulatory hierarchy," J. Bacteriol. 177:654–659.

Simon, R. et al. (1986) "Plasmid vectors for the genetic analysis and manipulation of rhizobia and other gram–negative bacteria," Meth. Enzym. 118–640–659.

Simon, R., et al. (1983) "A broad host range mobilization system for in vivo genetic engineering: transposon mutagenesis in gram negative bacteria," Bio–Technology 1:784–791.

Sitnikov, D.M. et al. (1995) "Transcriptional regulation of bioluminesence genes from Vibrio fischeri," Mol. Microbiol. 17:801–812.

Stevens, A.M. et al. (1994) "Synergistic binding of the Vibrio fischeri LuxR transcriptional activator domain and RNA polymerase to the lux promoter region," PNAS 91:12619–12623.

Suh, S. J. et al. (1999) "Effect of rpoS mutation on the stress response and expression of virulence factors in Pseudomonas aeruginosa," J Bacteriol. 181(13):3890–7.

Tang, H. B. et al. (1996) "Contribution of specific Pseudomonas aeruginosa virulence factors to pathogensis of pneumonia in a neonatal mouse model of infection," Infect Immun. 64(1):37–43.

* cited by examiner

FIGURE 3

```
         |   10       |   20       |   30       |   40       |   50       |   60       |   70       |   80
       1 GACCATGGCG  CACGATCGGG  TCGATGGATG  TGTAGTCTTC  GGAGATATAT  CTGCTTTTCC  ATTCCCCTGG  GTAATTGGAC   80
      81 AGGAAATGAT  ATTTAGGCGC  GGTCAGCGGG  AAAGGCGCCC  GCGCACCGAA  TGAAAAGAAT  TCGAATCCAT  AATTACCGCA  160
     161 TATCTCGAGA  ACCAGGGAGA  AGAACTCTTC  CTCGGTTGTT  ATTCTTGACA  AAATCTCGAG  ATATCCCTCT  CTCTCATCAT  240
     241 GCATGCCAGC  TTCACCAGTC  AACAATCGAT  CCCGGCAGGA  TTCGGTTCTT  CAGCGTTTTT  ATTCTTTTTT  GTTTCCGTCT  320
     321 TATCCACTCA  TGACAATTCC  CTTTATCAAG  CCGGACCTGG  AAGTACATAT  CGCCACCGGC  CCTGTGCGGG  TGTTCCGGAC  400
     401 GAGGTCGAGC  CCATTCGCCG  CCCGCCGGGC  GACGACGAAA  CGAGGCTGAA  GAGAACTTCC  CGATGAGCAC  GGACACGAGG  480
     481 CGCCGCGCAG  GAACTGCGCT  GGGCTGGAGG  GGACGGCGCC  CCGGATCTTT  GCGGAAACCG  TAGAACGGCT  CTCCGATGGG  560
     561 CCTCACGGCG  GTCTTTCTCA  TTGTTCTTCT  CGCACGCTCC  ATCGTCGTCG  GGAGAGCCTC  CCGACAACAA  ACCTTGGCCC  640
     641 ATGGCGGGCC  TCGTCGACGA  GGCTCCCCGG  GGACCAGAAA  TGGCAACTAC  ATACTTCCCC  CCCTATCTCT  CCGCAGATAC  720
     721 CTGCCCGAA   GGGCAGGTTG  TCCCTGCCGG  GCTGTGACAA  TTTAATTCGA  CCAGGCATTT  CATTGTCCGT  GCCGATTTTC  800
     801 ACGAAGCGCA  TTCTGAGGCA  ATTAAAAAGA  GCGCTCCATT  CGACCATGGA  CAAGCTATCC  ACGCCTGACC  GAGATCGCCT  880
     881 TCCGAATATA  GCGAAGCGAT  AACCGCAGCC  TGCCGAGAAG  TGCTTCAGAC  AATAAACAGG  ACGCTGGCCT  TTCGTATCGA  960
     961 TGAAAGTTCC  GCATGGCGTC  CGCCCCTAAG  GAAGAGGAGA  TAAATATGAT  TTATTACTTG  ATCGGAGTGG  CGCTATTCAT 1040
    1041 CTTCATGCTG  GAACAGTTGG  TTCCCGGCTG  GAAATTGCCC  AAGGTGAGCA  CCTGGGTGGC  CCGGGTGATC  TTCCTCAACA 1120
    1121 TCGTCCAGGT  GTCGATCGCC  CTGCTCGCCG  GCATCACCTG  GAACAAATGG  ATGATGGGGC  ACAGCCTGCT  GCACACCTCG 1200
    1201 GATGCCCTGC  CACCACTGCT  GGCCGGCTTC  GCCGCCTACT  TCGTCAACAC  CTTCGTCACC  TACTGGTGGC  ATCGCGCGCG 1280
    1281 CCACGCCAAC  GACACGCTCT  GGCGGCTGTT  CCACCAGTTG  CACCACGCGC  CGCAACGCAT  CGAGGTATTC  ACCTCCTTCT 1360
    1361 ACAAGCATCC  GACCGAGATG  GTCTTCAACT  CGCTGCTGGG  CAGCTTCGTC  GCCTACGTGG  TGATGGGCAT  CAGCATCGAG 1440
    1441 GCCGGCGCCT  ACTACATCAT  GTTCGCCGCG  CTCGGCGAGA  TGTTCTACCA  CTCGAACCTG  CGCACCCGCC  ACGTCCTCGG 1520
    1521 CTACCTGTTC  CAGCGCCCGG  AGATGCACCG  CATCCACCAC  CAGCGCGACC  GTCACGAGTG  CAACTACAGC  GACTTCCCGA 1600
    1601 TCTGGGACAT  GTTGTTCGGC  ACCTACGAGA  ACCCCCGCCG  CATCGACGAG  CCGCAGGGCT  CGCCGGCGA   CAAGGAGCAG 1680
    1681 CAGTTCGTCG  ACATGCTGCT  GTTCCGCGAC  GTGCACGACC  TCCCCGGAAA  AACCCAGCCC  GCTCCCGTCC  TGGTCAAGCC 1760
    1761 CGACGTCAGG  TGAACGCCAT  GATTCCAGAC  ATCGATTCCC  GTCTCAGCCG  GAACATATTG  AAATCCATCT  CGTATGGCCT 1840
    1841 CCCCCTCGCC  CGAAAGTGGT  CC  CGACCATAC  CTATGCGGCA  CTGGAAACAC  GCCTCGGCGA  ACTGAAACGC  AGGTATCTGG 1920
    1921 AGCTGCGCAT  CTCCCACGGC  GCGCGCGAGC  TGCCGTTCAG  CAACTACCTG  TTCTACCTGA  TCCTCCAGTC  GCGCCACCAG 2000
    2001 GAATTCGACT  TCAAGCTGCG  CCAGGGCAAC  TCGGTGGTCA  CCAACATCCA  CCGATTCAAG  AGCAAGGGAC  GCATCCCGTC 2080
    2081 CCTGACCACC  CTGCTCCTGG  CCGATGCGGT  CAACGCCAAG  AGCGAGCTGG  AGCTCAAGCA  TCCGGACATC  CCGCAGCTCG 2160
    2161 ACCGCCACGC  TCGCGACATC  GAGCGCTGGC  TGGCCGCCGG  CAACGTCATG  CCGCCCAGCG  AGCGGGCCCT  GCGCGGCCTG 2240
    2241 GTTGAGGCGC  TGGAGCGCGG  CGCTGGCGAA  GGCCGTCCGT  TGCACCTGGT  GAGCGCGGTA  TGCCCGGACT  ACTCGCACTC 2320
    2321 CAGCGATGCC  GAGGGCAAGC  CGCGCTACAC  CTTCGAGCGA  GTCGGCGACC  AGCCCGGCCT  GGCCGGCGCC  AAGCTGGTCA 2400
    2401 GCGCCGGCCA  GGCGGTGCGC  GAGCTGCCCA  GGGCGCGCCA  GGTGGAAATC  CGCCACGCGA  TCCTCGGCGG  CGAGTTCAGG 2480
    2481 TACCTATCGT  TCAACCGCAA  CCCCGCCACC  GGCGAGACCC  GCGAGGGTTT  CCTCGGCAAG  GTCGAGCGCC  AGCTCGAGCG 2560
    2561 GATCGCCGGG  GCCCTGCCCT  GCCCGGCCGG  GACCTGCTCG  TTCTTCGAGA  TGTGCGGCGG  CGAGGACGGC  TGGCACCAGG 2640
    2641 CCCACGGCGA  GATCGTCCAG  CGCCTGGAAC  AGGGCGACTA  CGGCCAGACC  GGGCTGGCCT  ACCCGGCCCT  GGAATCGATC 2720
    2721 TTCCTGTCGC  GCCTGCCGCT  CTACGAGAAA  TGGTTCGCCA  GCCAGTCGCG  CGAGCAGATC  TGGGCCAGCT  TCGTCTCCCA 2800
    2801 GGCCGCCGAG  TACGCATTGA  TGGGAAAACT  CTTCGGCGAG  CGCTTCGACA  ACTTCGTCGT  GCTGGCCGTC  GATCACTACC 2880
    2881 GGATGGAGCC  GTTCTACTCG  TTCTTCGCGA  CCGTCCCGAC  GCTCTACATC  CGAACCGACT  ACCTGTAACG  AGGGAGCGCC 2960
    2961 TGCGCCATGC  AAGATGAACT  GTTCAAGACC  CGATACTCCA  AGTACGGATA  CGGCATCGAC  GTGCGCCGTA  CCTACAAGGA 3040
    3041 CCTGCCCTGC  CAGCCGTTCT  GGACCTGGGT  CACCGGCAAG  TCGCTGAACG  ACCGCCCGCC  GCGACGGCCG  AAAGCACCC  3120
    3121 TGCTCAAGCC  CTGGCAGCTC  TACCTGCACA  TCAGTTGGGG  CTACGCGGTG  TTCTTCCTCG  CGGTGATCTA  CGGCCAGCAA 3200
    3201 CTGCTCGCCT  CGCAGCAGCC  ATTGTGCTG   AAGTGCCTGC  TGGGCGCGTT  GATCATGTGC  CTGGTGGTCA  ACCGCCAGCG 3280
    3281 TGGCTTCCTC  CATACCTTCC  ACTACACCAC  CCATGGCGCC  AGCCTGGAGA  ACAAGGCGCT  GGCCCGCTTC  ACCTGCAAGT 3360
    3361 GGATCCTGTC  GATCCCGATC  CTGCACACCC  CGCGCGACGA  GTACGTGAAG  CTGCACGTGA  ACGAACACCA  CAGCGTGCGC 3440
    3441 ACCTTCAATA  CCGAGCACGA  CGTCGACCTG  GTCTTCATGA  AACAGCACGG  CTTCTACAAG  GGCATGTCCG  AGAGCGCCTT 3520
    3521 CTGGACCCGC  CTGGTGCTCG  CGCCCTTCCA  TCCGGCGCGG  ATCCTCGAGC  ACCTGAAGTT  CCGTTCGAC   GTCAGCTTCG 3600
    3601 TCTCCGCCCC  GCGCCACGAG  CGCGTCAGCC  GGGCGCTCTA  CTGGGCTGCG  CTGCTCGGCC  TGGTGTACGC  CAGCGGCTAC 3680
    3681 CTGGAGGCGT  TCGCGCTGTT  CTACCTGTTC  CCGATCTTCA  TCCTCACCCA  GTACTCGTCG  TGGATCCAGC  ACGTCCCGA  3760
    3761 GCACCTCTGG  TTCGCCCGCA  ACGAGCACGG  CCTGCCGCGC  TTCCTGCACT  ACGGCTCGCT  GAGCTGGGGA  CGCTTCCTCG 3840
    3841 GCCGCCCCTA  CCCGGCCGAC  AAGCAGGGCC  TGGCCTTCGC  CCTGGCGTTC  GTTCGCTGGA  GCCTGGGCGT  GCTGCTGATC 3920
    3921 GACATCCCGC  TGCGGGTGTT  CTCCTTCATG  CAGGACCTGC  CCAGCCACGA  CTTCCACCAT  CGCAAGCCGG  GAGTGAACTT 4000
         |   10       |   20       |   30       |   40       |   50       |   60       |   70       |   80
```

FIGURE 7

1: gentamicin resistance

QUORUM SENSING SIGNALING IN BACTERIA

RELATED APPLICATIONS

This application claims priority to U.S. Provisional Patent Application No. 60/153,022, filed on Sep. 3, 1999, incorporated herein in its entirety by reference.

GOVERNMENT SUPPORT

This research was supported by grants and fellowships from the National Institutes of Health (GM59026), and the National Science Foundation (MCB9808308 and DBI9602247).

BACKGROUND OF THE INVENTION

Bacteria communicate with each other to coordinate expression of specific genes in a cell density dependent fashion. This "bacterial signaling" is a phenomenon called quorum sensing and response. Quorum sensing enables a bacterial species to sense its own number and regulate gene expression according to population density. In other words, quorum sensing is cell density-dependent regulation of genes that involves a freely diffusible molecule synthesized by the cell called an autoinducer (Fuqua, W. C. et al. (1996) *Annu. Rev. Microbiol.* 50:727–751; Salmond, G. P. C. et al. (1995) *Mol. Microbiol.* 16:615–624; Sitnikov, D. M. et al. (1995) *Mol. Microbiol.* 17:801–812). Autoinducers are described, e.g., in U.S. Pat. Nos. 5,591,872 and 5,593,827.

The paradigm system for quorum sensing is the lux system of the luminescent marine bacterium, *Vibrio fischeri*. *V. fischeri* exists at low cell densities in sea water and also at very high cell densities within the light organs of various marine organisms, such as the squid *Euprymna scolopes* (Pesci, E. C. et al. (1997) *Trends in Microbiol.* 5(4) :132–135; Pesci, E. C. et al. (1997) *J. Bacteriol.* 179:3127–3132; Ruby, E. G. (1996) *Ann. Rev. Microbiol.* 50:591–624). At high cell densities, the *V. fischeri* genes encoding the enzymes required for light production are expressed. These genes are part of the lux ICDABEG operon and are regulated by the gene products of luxI and luxR (Baldwin, T. O. et al. (1989) *J. of Biolum. and Chemilum.* 4:326–341; Eberhard, A., et al. (1991) *Arch. of Microbiol.* 155:294–297; Gray, K. M. et al. (1992) *J. bacteriol.* 174:4384–4390).

LuxI is an autoinducer synthase that catalyzes the formation of the *V. fischeri* autoinducer (VAI), N-(3oxohexanoyl) homoserine lactone (Eberhard, A., et al. (1991) *Arch. of Microbiol.* 155:294–297; Seed, P. C. et al. (1995) *J. Bacteriol.* 177:654–659). The autoinducer freely diffuses across the cell membrane and at high cell densities, reaches a critical concentration (Kaplan, H. B. et al. (1985) *J. bacteriol.* 163:1210–1214). At this critical concentration, VAI interacts with LuxR, a DNA-binding transcriptional regulator. The LuxR-VAI complex then binds to an upstream sequence of the lux operon called the "lux box", and activates transcription (Devine, J. H. et al. (1989) *PNAS* 86: 5688–5692; Hanzelka, B. A. et al. (1995) *J. bacteriol.* 177:815–817; Stevens, A. M. et al. (1994) *PNAS* 91:12619–12623). Since one of the genes of the operon is luxI, an autoregulatory loop is formed.

Many gram-negative bacteria have been shown to possess one or more quorum sensing systems (Fuqua, W. C. et al. (1996) *Annu. Rev. Microbiol.* 50:727–751; Salmond, G. P. C. et al. (1995) *Mol. Microbiol.* 16:615–624). These systems regulate a variety of physiological processes, including the activation of virulence genes and the formation of biofilms. The systems typically have acylated homoserine lactone ring autoinducers, in which the homoserine lactone ring is conserved. The acyl side chain, however, can vary in length and degree of substitution. In addition, it has been recently demonstrated that quorum sensing is involved in biofilm formation (Davies, D. G. et al. (1998) *Science.* 280(5361) :295–8).

Biofilms are defined as an association of microorganisms, single or multiple species, that grow attached to a surface and produce a slime layer that provides a protective environment (Costerton, J. W. (995) *J Ind Microbiol.* 15(3) :137–40, Costerton, J. W. et al. (1995) *Annu Rev Microbiol.* 49:711–45). Typically, biofilms produce large amounts of extracellular polysaccharides, responsible for the slimy appearance, and are characterized by an increased resistance to antibiotics (1000- to 1500-fold less susceptible). Several mechanisms are proposed to explain this biofilm resistance to antimicrobial agents (Costerton, J. W. et al. (1999) *Science.* 284(5418):1318–22). One idea is that the extracellular matrix in which the bacterial cells are embedded provides a barrier toward penetration by the biocides. A further possibility is that a majority of the cells in a biofilm are in a slow-growing, nutrient-starved state, and therefore not as susceptible to the effects of anti-microbial agents. A third mechanism of resistance could be that the cells in a biofilm adopt a distinct and protected biofilm phenotype, e.g., by elevated expression of drug-efflux pumps.

In most natural settings, bacteria grow predominantly in biofilms. Biofilms of *P. aeruginosa* have been isolated from medical implants, such as indwelling urethral, venous or peritoneal catheters (Stickler, D. J. et al. (1998) *Appl Environ Microbiol.* 64(9):3486–90). Chronic *P. aeruginosa* infections in cystic fibrosis lungs are considered to be biofilms (Costerton, J. W. et al. (1999) *Science.* 284(5418) :1318–22).

In industrial settings, the formation of biofilms is often referred to as 'biofouling'. Biological fouling of surfaces is common and leads to material degradation, product contamination, mechanical blockage, and impedance of heat transfer in water-processing systems. Biofilms are also the primary cause of biological contamination of drinking water distribution systems, due to growth on filtration devices.

As noted earlier, many gram-negative bacteria have been shown to possess one or more quorum sensing systems that regulate a variety of physiological processes, including the activation of virulence genes and biofilm formation. One such gram negative bacterium is *Pseudomonas aeruginosa*.

*P. aeruginosa* is a soil and water bacterium that can infect animal hosts. Normally, the host defense system is adequate to prevent infection. However, in immunocompromised individuals (such as bum patients, patients with cystic fibrosis, or patients undergoing immunosuppressive therapy), *P. aeruginosa* is an opportunistic pathogen, and infection with *P. aeruginosa* can be fatal (Govan, J. R. et al. (1996) *Microbiol Rev.* 60(3):539–74; Van Delden, C. et al. (1998) *Emerg Infect Dis.* 4(4):551–60).

For example, Cystic fibrosis (CF), the most common inherited lethal disorder in Caucasian populations (~1 out of 2,500 life births), is characterized by bacterial colonization and chronic infections of the lungs. The most prominent bacterium in these infections is *P. aeruginosa*—by their mid-twenties, over 80% of people with CF have *P. aeruginosa* in their lungs (Govan, J. R. et al. (1996) *Microbiol Rev.* 60(3):539–74). Although these infections can be controlled for many years by antibiotics, ultimately they "progress to mucoidy," meaning that the *P. aeruginosa* forms a biofilm that is resistant to antibiotic treatment. At this point the prognosis is poor. The median survival age for people with CF is the late 20s, with *P. aeruginosa* being the leading cause of death (Govan, J. R. et al. (1996) *Microbiol Rev.* 60(3):539–74). According to the Cystic Fibrosis Foundation, treatment of CF cost more than $900 million in 1995.

*P. aeruginosa* is also one of several opportunistic pathogens that infect people with AIDS, and is the main cause of bacteremia (bacterial infection of the blood) and pneumonitis in these patients (Rolston, K. V. et al. (1990) *Cancer Detect Prev.* 14(3):377–81; Witt, D. J. et al. (1987) *Am J Med.* 82(5):900–6). A recent study of 1635 AIDS patients admitted to a French hospital between 1991–1995 documented 41 cases of severe *P. aeruginosa* infection (Meynard, J. L. et al. (1999) *J Infect.* 38(3):176–81). Seventeen of these had bacteremia, which was lethal in 8 cases. Similar, numbers were obtained in a smaller study in a New York hospital, where the mortality rate for AIDS patients admitted with *P. aeruginosa* bacteremia was about 50% (Mendelson, M. H. et al. 1994. *Clin Infect Dis.* 18(6):886–95).

In addition, about two million Americans suffer serious burns each year, and 10,000–12,000 die from their injuries. The leading cause of death is infection (Lee, J. J. et al. (1990) *J Burn Care Rehabil.* 11(6):575–80). *P. aeruginosa* bacteremia occurs in 10% of seriously burned patients, with a mortality rate of 80% (Mayhall, C. G. (1993) p. 614–664, Prevention and control of nosocomial infections. Williams & Wilkins, Baltimore; McManus, A. T et al. (1985) *Eur J Clin Microbiol.* 4(2):219–23).

Such infections are often acquired in hospitals ("nosocomial infections") when susceptible patients come into contact with other patients, hospital staff, or equipment. In 1995 there were approximately 2 million incidents of nosocomial infections in the U.S., resulting in 88,000 deaths and an estimated cost of $ 4.5 billion (Weinstein, R. A. (1998) *Emerg Infect Dis.* 4(3):416–20). Of the AIDS patients mentioned above who died of *P. aeruginosa* bacteremia, more than half acquired these infections in hospitals (Meynard, J. L. et al. (1999) *J Infect.* 38(3):176–81).

Nosocomial infections are especially common in patients in intensive care units as these people often have weakened immune systems and are frequently on ventilators and/or catheters. Catheter-associated urinary tract infections are the most common nosocomial infection (Richards, M. J. et al. (1999) *Critical Care Med.* 27(5):887–92) (31% of the total), and *P. aeruginosa* is highly associated with biofilm growth and catheter obstruction. While the catheter is in place, these infections are difficult to eliminate (Stickler, D. J. et al. (1998) *Appl Environ Microbiol.* 64(9):3486–90). The second most frequent nosocomial infection is pneumonia, with *P. aeruginosa* the cause of infection in 21% of the reported cases (Richards, M. J. et al. (1999) *Critical Care Med.* 27(5):887–92). The annual costs for diagnosing and treating nosocomial pneumonia has been estimated at greater than $2 billion (Craven, D. E. et al. (1991) *Am J Med.* 91(3B):44S–53S).

Treatment of these so-called nosocomial infections is complicated by the fact that bacteria encountered in hospital settings are often resistant to many antibiotics. In June 1998, the National Nosocomial Infections Surveillance (NNIS) System reported increases in resistance of *P. aeruginosa* isolates from intensive care units of 89% for quinolone resistance and 32% for imipenem resistance compared to the years 1993–1997 (see the NNIS webiste). In fact, some strains of *P. aeruginosa* are resistant to over 100 antibiotics (Levy, S. (1998) *Scientific American.* March). There is a critical need to overcome the emergence of bacterial strains that are resistant to conventional antibiotics (Travis, J. (1994) *Science.* 264:360–362).

*P. aeruginosa* is also of great industrial concern (Bitton, G. (1994) Wastewater Microbiology. Wiley-Liss, New York, N.Y.; Steelhanrner, J. C. et al. (1995) *Indust. Water Treatm.*:49–55). The organism grows in an aggregated state, the biofilm, which causes problems in many water processing plants. Of particular public health concern are food processing and water purification plants. Problems include corroded pipes, loss of efficiency in heat exchangers and cooling towers, plugged water injection jets leading to increased hydraulic pressure, and biological contamination of drinking water distribution systems (Bitton, G. (1994) Wastewater Microbiology. Wiley-Liss, New York, N.Y., 9). The elimination of biofilms in industrial equipment has so far been the province of biocides. Biocides, in contrast to antibiotics, are antimicrobials that do not possess high specificity for bacteria, so they are often toxic to humans as well. Biocide sales in the US run at about $ 1 billion per year (Peaff, G. (1994) *Chem. Eng. News:* 15–23).

A particularly ironic connection between industrial water contamination and public health issues is an outbreak of *P. aeruginosa* peritonitis that was traced back to contaminated poloxamer-iodine solution, a disinfectant used to treat the peritoneal catheters. *P. aeruginosa* is commonly found to contaminate distribution pipes and water filters used in plants that manufacture iodine solutions. Once the organism has matured into a biofilm, it becomes protected against the biocidal activity of the iodophor solution. Hence, a common soil organism that is harmless to the healthy population, but causes mechanical problems in industrial settings, ultimately contaminated antibacterial solutions that were used to treat the very people most susceptible to infection.

Regulation of virulence genes by quorum sensing is well documented in *P. aeruginosa*. Recently, genes not directly involved in virulence including the stationary phase sigma factor rpoS and genes coding for components of the general secretory pathway (xcp) (Jamin, M. et al. (1991) *Biochem J.* 280(Pt 2):499–506) have been reported to be positively regulated by quorum sensing. Furthermore, the las quorum sensing system is required for maturation of *P. aeruginosa* biofilms (Chapon-Herve, V. et al. (1997) *Mol. Microbiol.* 24, 1169–1170; Davies, D. G., et al. (1998) *Science* 280, 295–298). Thus it seems clear that quorum sensing represents a global gene regulation system in *P. aeruginosa*. However, the number and types of genes controlled by quorum sensing have not been identified or studied extensively.

SUMMARY OF THE INVENTION

In general, the invention pertains to the modulation of bacterial cell-to-cell signaling. The inhibition of quorum sensing signaling renders a bacterial population more susceptible to treatment, either directly through the host immune-response or in combination with traditional antibacterial agents and biocides. More particularly, the invention also pertains to a method for identifying modulators, e.g., inhibitors of cell-to-cell signaling in bacteria, and in particular one particular human pathogen, *Pseudomonas aeruginosa*.

Thus in one aspect, the invention is a method for indentifying a modulator of quorum sensing signaling in bacteria.

The method comprises:

providing a cell comprising a quorum sensing controlled gene, wherein the cell is responsive to a quorum sensing signal molecule such that a detectable signal is generated;

contacting said cell with a quorum sensing signal molecule in the presence and absence of a test compound;

and detecting a change in the detectable signal to thereby identify the test compound as a modulator of quorum sensing signaling in bacteria.

In one embodiment the cell comprises a reporter gene operatively linked to a regulatory sequence of a quorum sensing controlled gene, such that the quorum sensing signal molecule modulates the transcription of the reporter gene, thereby providing a detectable signal.

Another aspect of the invention is a method for identifying a modulator of a quorum sensing signaling in *Pseudomonas aeruginosa*. The method comprises:

providing a wild type strain of *Pseudomonas aeruginosa* which produces a quorum sensing signal molecule;

providing a mutant strain of *Pseudomonas aeruginosa* which comprises a reporter gene operatively linked to a regulatory sequence of a quorum sensing controlled gene, wherein the mutant strain is responsive to the quorum sensing signal molecule produced by the wild type strain, such that a detectable signal is generated;

contacting the mutant strain with the quorum sensing signal molecule and a test compound; and detecting a change in the detectable signal to thereby. identify the test compound as a modulator of quorum sensing signaling in *Pseudomonas aeruginosa*.

In one embodiment, the endogenous lasI and rhlI quorum sensing systems are inactivated in the mutant strain of *Pseudomonas aeruginosa*. In another embodiment the mutant strain of *Pseudomonas aeruginosa* comprises a promoterless reporter gene inserted at a genetic locus in the chromosome, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

A further aspect of the invention is a mutant strain of *Pseudomonas aeruginosa* comprising a promoterless reporter gene inserted at a genetic locus in the chromosome, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO: 18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

In one embodiment, the endogenous lasI and rhlI quorum sensing systems are, inactivated in the mutant strain of *Pseudomonas aeruginosa*. In another embodiment the mutant strain of *Pseudomonas aeruginosa* is responsive to a quorum sensing signal molecule such that a detectable signal is generated by the reporter gene. In yet another embodiment, the reporter gene is contained in a transposable element.

Yet another aspect of the invention is a method for identifying a modulator of quorum sensing signaling in *Pseudomonas aeruginosa*. The method comprises:

providing a wild type strain of *Pseudomonas aeruginosa* which produces a quorum sensing signal molecule;

providing a mutant strain of *Pseudomonas aeruginosa* which comprises a promoterless reporter gene inserted at a genetic locus in the chromosome of said *Pseudomonas aeruginosa*, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36; and wherein the mutant strain is responsive to the quorum sensing signal molecule produced by the wild type strain, such that a detectable signal is generated by the reporter gene;

contacting the mutant strain with the quorum sensing signal molecule and a test compound; and detecting a change in the detectable signal to thereby identify the test compound as a modulator of quorum sensing signaling in *Pseudomonas aeruginosa*.

Another aspect of the invention is an isolated nucleic acid molecule comprising a nucleotide sequence which comprises:

a regulatory sequence derived from the genome of *Pseudomonas aeruginosa*, wherein the regulatory sequence regulates a quorum sensing controlled genetic locus of the *Pseudomonas aeruginosa* chromosome, and wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36; and a reporter gene operatively linked to the regulatory sequence.

A further aspect of the invention provides an isolated nucleic acid molecule comprising a quorum sensing controlled genetic locus derived from the genome of *Pseudomonas aeruginosa*, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36, operatively linked to a reporter gene.

In one embodiment, the invention is an isolated nucleic acid molecule comprising a polynucleotide having at least 80% identity to a quorum sensing controlled genetic locus derived from the genome of Pseudomonas aeruginosa, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36, operatively linked to a reporter gene.

In another embodiment, the invention is an isolated nucleic acid molecule comprising a polynucleotide that hybridizes under stringent conditions to a quorum sensing controlled genetic locus derived from the genome of Pseudomonas aeruginosa, wherein the genetic locus comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36, operatively linked to a reporter gene.

In one embodiment, an isolated nucleic acid molecule of the invention comprises a reporter gene contained in a transposable element.

Accordingly, a further aspect of the invention pertains to a vector comprising an isolated nucleic acid molecule of the invention. In another aspect, the invention provides cells containing an isolated nucleic acid molecule of the invention.

An additional aspect of the invention is a method for identifying a modulator of quorum sensing signaling in bacteria. The method comprises: providing a cell containing an isolated nucleic acid molecule of the invention, wherein the cell is responsive to a quorum sensing signal molecule such that a detectable signal is generated;

contacting said cell with a quorum sensing signal molecule in the presence and absence of a test compound;

and detecting a change in the detectable signal to therby identify the test compound as a modulator of quorum sensing signaling in bacteria.

Accordingly, in another aspect, the invention provides a compound identified by a method of the invention which modulates, e.g., inhibits, quorum sensing signaling in Pseudomonas aeruginosa. In one embodiment, the compound inhibits quorum sensing signaling in Pseudomonas aeruginosa by inhibiting an enzyme involved in the synthesis of a quorum sensing signal molecule, by interfering with quorum sensing signal reception, or by scavenging the quorum sensing signal molecule.

The invention also pertains to a method for identifing quorum sensing controlled genes in a cell, and specifically in one particular human pathogen, Pseudomonas aeruginosa. Thus, in one aspect, the invention provides a method for identifying a quorum sensing controlled gene in a cell, the method comprising:

providing a cell which is responsive to a quorum sensing signal molecule such that expression of a quorum sensing controlled gene is modulated, and wherein modulation of the expression of said quorum sensing controlled gene generates a detectable signal;

contacting said cell with a quorum sensing signal molecule;

and detecting a change in the detectable signal to thereby identify a quorum sensing signaling controlled gene.

In one embodiment the cell comprises a reporter gene operatively linked to a quorum sensing controlled gene or a regulatory sequence of a quorum sensing controlled gene, such that modulation of the expression of the quorum sensing controlled gene modulates the transcription of the reporter gene, thereby providing a detectable signal. In another embodiment the reporter gene is contained in a transposable element. In yet another embodiment, the quorum sensing signal molecule is produced by a second cell, e.g., a bacterial cell. In a further embodiment, the quorum sensing signal molecule is an autoinducer of said quorum sensing controlled gene, e.g., a homoserine lactone, or an analog thereof.

BRIEF DESCRIPTION OF THE DRAWINGS

FIG. 3 depicts the nucleic acid sequence of the quorum sensing controlled locus on the P. aeruginosa chromosome mapped in the P. aeruginosa mutant strain qsc102.

FIG. 7 depicts putative las-type boxes in upstream DNA regions of qsc mutants. ORFs as described in Materials and Methods. Bases outlined in black represent residues conserved in all sequences and gray outlines are conserved in 8 of 10 sequences.

DETAILED DESCRIPTION OF THE INVENTION

Figure 1:
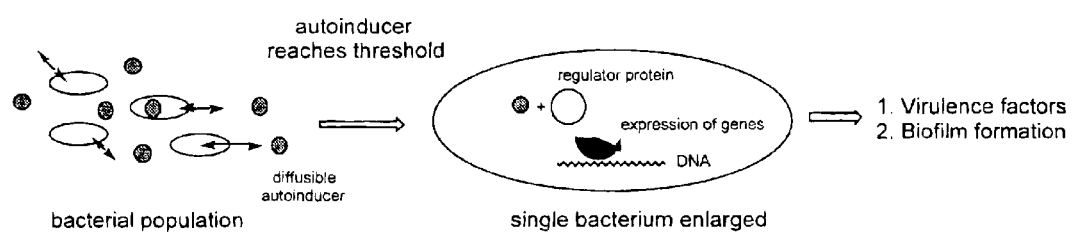
FIG. 1 depicts the paradigm for quorum sensing signaling in the target bacterium, Pseudomonas aeruginosa.

In gram-negative bacteria, such as *Pseudomonas aeruginosa*, quorum sensing involves two proteins, the autoinducer synthase—the I protein—and the transcriptional activator—the R protein. The synthase produces an acylated homoserine lactone (the "autoinducer"; see structure 1 below), which can diffuse into the surrounding environment (Fuqua, C. et al. (1998) *Curr Opin Microbiol.* 1(2):183–189; Fuqua, et al. 1994. *J bacteriol.* 176(2):269–75). The autoinducer molecule is composed of an acyl chain in a peptide bond with the amino nitrogen of a homoserine lactone (HSL). For different quorum sensing systems, the side-chain may vary in length, degree of saturation, and oxidation state. As the density of bacteria increases, so does the concentration of this freely diffusible signal molecule. Once the concentration reaches a defined threshold, it binds to the R-protein, which then activates transcription of numerous genes. Of particular interest are genes involved in pathogenicity and in biofilm formation (see FIG. 1).

*Pseudomonas aeruginosa* has two quorum sensing systems, las and rhl, named for their role in the expression of elastase, and the RhlI/RhlR proteins, which were first described for their role in rhamnotipid biosynthesis. (Hanzelka, B. A. et al. (1996) *J. Bacteriol.* 178:5291–5294; Baldwin, T. O. et al. (1989) *J. of Biolum. and Chemilum.* 4:326–341; Passador, L., et al. (1993) *Science* 260:1127–1130; Pearson, J. P et al. (1994) *PNAS* 91:197–201; Pesci, E. C. et al. (1997) *Trends in Microbiol.* 5(4):132–135; Pesci, E. C. et al. (1997) *J. Bacieriol.* 179:3127–3132). The two systems have distinct autoinducer synthases (lasI and rhlI), transcriptional regulators (lasR and rhlR), and autoinducers (N-(3-oxododecanoyl) homoserine lactone (HSL) and N-butyryl HSL) (Sitnikov, D. M. et al. (1995) *Mol. Microbiol.* 17:801–812). The rhl and las systems are involved in regulating the expression of a number of secreted virulence factors, biofilm development, and the stationary phase sigma factor (RpoS) (Davies, D. G. et al. (1998) *Science* 280:295–298; Latifi, A. et al. (1995) *Mol. Microbiol. Rev.* 17:333–344; Ochsner, U. A., et al. (1995) *PNAS,* 92:6424–6428; Pesci, E. C. et al. (1997) *Trends in Microbiol* 5(4):132–135; Pesci, E. C. et al. (1997) *J. bacteriol.* 179:3127–3132). Expression of the rhl system requires a functional las system, therefore the two systems in combination with RpoS constitute a regulatory cascade (Pesci, E. C. et al. (1997) *Trends in Microbiol.* 5(4) :132–135; Pesi, E. C. et al. (1997) *J. bacteriol.* 179:3127–3132, Seed et al. 1995).

The signal in the Las system is 3-oxo-dodecanoyl-HSL (3-oxo-C12-HSL) 2, while the signal used in the Rhl system is butanoyl-HSL (C4-HSL) 3. It has been shown that 3-oxo-C12-HSL increases expression of RhlR, indicating a hierarchy of regulation systems (Pesci, E. C. et al. (1997) *Trends Microbiol.* 5(4):132–4). The Las signal 3-oxo-C12-HSL is synthesized by LasI along with a small amount of N-(3-oxooctanoyl) HSL and N-(3-oxohexanoyl) HSL, while RhlI makes primarily the signal C4-HSL and a small amount of N-hexanoyl (Pearson, J. P. et al. (1997) *J. Bacteriol.* 179:5756–5757; Winson, M. K. et al. (1995) *PNAS* 92:9427–943 1).

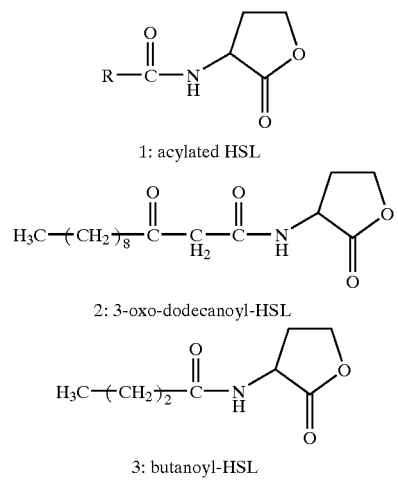

1: acylated HSL

2: 3-oxo-dodecanoyl-HSL

3: butanoyl-HSL

Bacterial signaling triggers the expression of a number of virulence factors in *P. aeruginosa* including two elastases, an alkaline protease and exotoxin A (Pesci, E. C. et al. (1997) *Trends Microbiol.* 5(4):132–4; Pesci, E. C. et al. (1997) *J Bacteriol.* 179(10):3127–32)—proteins that allow the organism to attack host tissue. Bacterial signaling also controls the expression of the antioxidant pyocyanin, a compound that allows the bacteria to neutralize one important host defense, the generation of superoxide radicals (Britigan, et al. (1999) *Infect Immun.* 67(3):1207–12, Hassan, H. M. et al. (1979) *Arch Biochem Biophys.* 196(2) :385–95, Hassan, H. M. et al. 1980. *J Bacteriol.* 141(1) :156–63). It has been shown in a neonatal mouse model that a defined mutant of *P. aeruginosa* which lacks the signal receptor protein (LasR) was significantly less virulent than the wild type PAO1, as measured by the ability to cause acute pneumonia, bacteremia and death (Tang, H. B. et al. (1996) *Infect Immun.* 64(1):37–43).

The invention is based on the interruption of bacterial cell-to-cell signaling, i.e., quorum sensing signaling in order to render a bacterial population more susceptible to treatment, either through the host immune-response or in combination with traditional antibacterial agents and biocides. Thus, the invention provides a bacterial indicator strain that allows for a high throughput screening assay for identifying compounds that modulate, e.g., inhibit bacterial cell-to-cell signaling. The compounds so identified will provide novel anti-pathogenics and anti-fouling agents.

Definitions

Before further description of the invention, certain terms employed in the specification, examples and appended claims are, for convenience, collected here.

The term "analog" as in "homoserine lactone analog" is intended to encompass compounds that are chemically and/ or electronically similar but have different atoms, such as isosteres and isologs. An analog includes a compound with a structure similar to that of another compound but differing from it in respect to certain components or structural makeup. The term analog is also intended to encompass stereoisomers.

The language "autoinducer compounds" is art-recognized and is intended to include molecules, e.g., proteins which freely diffluse across cell membranes and which activate tnanscription of various factors which affect bacterial viability. Such compounds can affect virulence, and biofilm development. Autoinducer compounds can be acylated homoserine lactones. They can be other compounds similar to those listed in Table 1. Homoserine autoinducer compounds are produced in vivo by the interaction of a homoserine lactone substrate and an acylated acyl carrier protein in a reaction catalyzed by an autoinducer synthase molecule. In isolated form, autoinducer compounds can be obtained from naturally occurring proteins by purifying cellular extracts, or they can be chemically synthesized or recombinantly produced. The language "autoinducer synthase molecule" is intended to include molecules, e.g. proteins, which catalyze or facilitate the synthesis of autoinducer compounds, e.g. in the quorum sensing system of bacteria. It is also intended to include active portions of the autoinducer synthase protein contained in the protein or in fragments or portions of the protein (e.g., a biologically active fragment). The language "active portions" is intended to include the portion of the autoinducer synthase protein which contains the homoserine lactone binding site. Table 1 contains a list of exemplary autoinducer synthase proteins of the quorum sensing systems of various gram-negative bacteria.

TABLE 1

Summary of N-acyl homoserine lactone based regulatory systems

| Bacterial species | Signal molecules[a] | Regulatory Proteins[b] | Target function(s) |
|---|---|---|---|
| Vibrio fischeri | N-3-(oxohexanoyl)-homoserine lactone (VAI-1) | LuxI/LuxR | luxICDABEG, luxR luminescence |
| | N-(octanoyl)-L-homoserine lactone (VAI-2) | AinS/AinR[c] | luxICDABEG, ? |
| Vibrio harveyi | N-β-(hydroxybutyryl)-homoserine lactone (HAI-1) | LuxM/LuxN-LuxO-LuxR[d] | luxICDABEG, luminescence and polyhydroxybutyrate synthesis |
| | HAI-2 | Lux?/LuxPQ-LuxO-LuxR[d] | luxCDABEG |
| Pseudomonas aeruginosa | N-3-(oxododecanyoyl)-L-homoserine lactone (PAI-1) | LasI/LasR | lasB, lasA, aprA, toxA, virulence factors |
| | N-(butyryl)-L-homoserine lactone (PAI-2) | RhII/RhIR | rhIAB, rhamnolipid synthesis, virulence factors |
| Pseudomonas aeureofaciens | (PRAI)[e] | PhzI/PhzR | phz, phenazine biosynthesis |
| Agroacterium tumefaciens | N-3-(oxooctanoyl)-L-homoserine lactone (AAI) | TraI/TraR-TraM | tra gens, traR, Ti plasmid conjugal transfer |
| Erwinia carotovora subsp. carotovora SCRI193 | VAI-1[f] | ExpI/ExpR | pel, pec, pep, exoenzyme synthesis |
| Erwinia carotovora subsp. carotovora SCC3193 | VAI-1[f] | CarI/CarR | cap, carbapenem antibiotic synthesis |
| Erwinia carotovora subsp. carotovora 71 | VAI-1[f] | HsII/? | pel, pec, pep, exoenzyme synthesis |
| Erwinia stewartii | VAI-1[f] | EsaI/EsaR | wts genes, exopolysaccharide synthesis, virulence factors |
| Rhizobium leguminosarum | N-(3R-hydroxy-7-cis-tetradecanoyl-L-homoserine lactone, small bacteriocin, (RLAI) | ?/RhiR | rhiABC, rhizosphere genes and stationary phase |
| Enterobacter agglomerans | VAI-1[f] | EagI/EagR | function unclear |
| Yersenia enterocolitica | VAI-1[f] | YenI/YenR | function unclear |
| Serratia liquifaciens | N-butanoyl-L-homoserine lacton (SAI-1) | SwrI/? | swarming motility |
| | N-hexanoyl-L-homoserine lacton (SAI-2) | SwrI/? | swarming motility |
| Aeromonas hydrophila | (AHAI)[e] | AhyI/AhyR | function unclear |
| Escherichia coli/?[g] | | ?/SdiA | ftsQAZ, cell division |

Autoinducer synthase molecules can be obtained from naturally occurring sources, e.g., by purifying cellular extracts, can be chemically synthesized or can be recombinantly produced. Recombinantly produced autoinducer synthase molecules can have the amino acid sequence of a naturally occurring form of the autoinducer synthase protein. They can also have a similar amino acid sequence which includes mutations such as substitutions and deletions (including truncation) of a naturally occurring form of the protein. Autoinducer synthase molecules can also include molecules which are structurally similar to the structures of naturally occurring autoinducer synthase proteins, e.g., biologically active variants.

TraI, LuxI, RhlI are the homoserine lactone autoinducer syntheses of *Agrobacterium tumefaceins, Vibrio fischeri,* and *Pseudomonas aeruginosa,* respectively. The term "RhlI" is intended to include proteins which catalyze the synthesis of the homoserine lactone autoinducer of the RhlI quorum sensing system of *P. aeruginosa*, butyryl homoserine lactone.

The term "biofilm" is intended to include biological films that develop and persist at interfaces in aqueous environments. Biofilms are composed of microorganisms embedded in an organic gelatinous structure composed of one or more matrix polymers which are secreted by the resident microorganisms. The language "biofilm development" or "biofilm formation" is intended to include the formation, growth, and modification of the bacterial colonies contained with the biofilm structures as well as the synthesis and maintenance of the exopolysaccharide matrix of the biofilm structures.

The term "compound" as used herein (e.g., as in "test compound," or "modulator compound") is intended to include both exogenously added test compounds and peptides endogenously expressed from a peptide library. Test compounds may be purchased, chemically synthesized or recombinantly produced. Test compounds can be obtained from a library of diverse compounds based on a desired activity, or alternatively they can be selected from a random screening procedure. In one embodiment, an indicator cell (e.g., a cell which responds to quorum sensing signals by generating a detectable signal) also produces the test compound which is being screened. For instance, the indicator cell can produce, e.g., a test polypeptide, a test nucleic acid and/or a test carbohydrate, which is screened for its ability to modulate quorum sensing signaling. In such embodiments, a culture of such reagent cells will collectively provide a library of potential modulator molecules and those members of the library which either stimulate or inhibit quorum sensing signaling can be selected and identified. In another embodiment, a test compound is produced by a second cell which is co-incubated with the indicator cell.

The terms "derived from" or "derivative", as used interchangeably herein, are intended to mean that a sequence is identical to or modified from another sequence, e.g., a naturally occurring sequence. Derivatives within the scope of the invention include polynucleotide derivatives. Polynucleotide or nucleic acid derivatives differ from the sequences described herein (e.g., SEQ ID Nos.: 1–38) or known in nucleotide sequence. For example, a polynucleotide derivative may be characterized by one or more nucleotide substitutions, insertions, or deletions, as compared to a reference sequence. A nucleotide sequence comprising a quorum sensing controlled genetic locus that is derived from the genome of *P. aeruginosa*, e.g., SEQ ID Nos.: 1–38, includes sequences that have been modified by various changes such as insertions, deletions and substitutions, and which retain the property of being regulated in response to a quorum sensing signaling event. Such sequences may comprise a quorum sensing controlled regulatory element and/or a quorum sensing controlled gene. The nucleotide sequence of the *P. aeruginosa* genome is available at the *Pseudomonas* Genome Project website.

Polypeptide or protein derivatives include polypeptide or protein sequences that differ from the sequences described or known in amino acid sequence, or in ways that do not involve sequence, or both, and still preserve the activity of the polypeptide or protein. Derivatives in amino acid sequence are produced when one or more amino acids is substituted with a different natural amino acid, an amino acid derivative or non-native amino acid. In certain embodiments protein derivatives include naturally occurring polypeptides or proteins, or biologically active fragments thereof, whose sequences differ from the wild type sequence by one or more conservative amino acid substitutions, which typically have minimal influence on the secondary structure and hydrophobic nature of the protein or peptide. Derivatives may also have sequences which differ by one or more non-conservative amino acid substitutions, deletions or insertions which do not abolish the biological activity of the polypeptide or protein.

Conservative substitutions (substituents) typically include the substitution of one amino acid for another with similar characteristics (e.g., charge, size, shape, and other biological properties) such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, prolinc, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

In other embodiments, derivatives with amino acid substitutions which are less conservative may also result in desired derivatives, e.g., by causing changes in charge, conformation and other biological properties. Such substitutions would include, for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics. The polypeptides and proteins of this invention may also be modified by various changes such as insertions, deletions and substitutions, either conservative or nonconservative where such changes might provide for certain advantages in their use.

As used herein, the term "genetic locus" includes a position on a chromosome, or within a genome, which is associated with a particular gene or genetic sequences having a particular characteristic. For example, in one embodiment, a quorum sensing controlled genetic locus includes nucleic acid sequences which comprise an open reading frame (ORF) of a quorum sensing controlled gene. In another embodiment, a quorum sensing controlled genetic locus includes nucleic acid sequences which comprise transcriptional regulatory sequences that are responsive to quorum sensing signaling (e.g., a quorum sensing controlled regulatory element). Examples of quorum sensing controlled genetic loci of *P. aeruginosa* are described herein as SEQ ID NOs.:1–38.

The term "modulator", as in "modulator of quorum sensing signaling" is intended to encompass, in its various grammatical forms, induction and/or potentiation, as well as inhibition and/or downregulation of quorum sensing signaling and/or quorum sensing controlled gene expression. As used herein, the term "modulator of quorum sensing signaling" includes a compound or agent that is capable of modulating or regulating at least one quorum sensing controlled gene or quorum sensing controlled genetic locus, e.g., a quorum sensing controlled genetic locus in *P. aeruginosa*, as described herein. A modulator of quorum sensing signaling may act to modulate either signal generation (e.g., the synthesis of a quorum sensing signal molecule), signal reception (e.g., the binding of a signal molecule to a receptor or target molecule), or signal transmission (e.g., signal transduction via effector molecules to generate an appropriate biological response). In one embodiment, a method of the present invention encompasses the modulation of the transcription of an indicator gene in response to an autoinducer molecule. In another embodiment, a method of the present invention encompasses the modulation of the transcription of an indicator gene, preferably an quorum sensing controlled indicator gene, by a test compound.

The term "operatively linked" or "operably linked" is intended to mean that molecules are functionally coupled to each other in that the change of activity or state of one molecule is affected by the activity or state of the other molecule. In one embodiment, nucleotide sequences are "operatively linked" when the regulatory sequence functionally relates to the DNA sequence encoding the polypeptide or protein of interest. For example, a nucleotide sequence comprising a transcriptional regulatory element(s) (e.g., a promoter) is operably linked to a DNA sequence encoding the protein or polypeptide of interest if the promoter nucleotide sequence controls the transcription of the DNA sequence encoding the protein of interest. In addition, two nucleotide sequences are operatively linked if they are coordinately regulated and/or transcribed. Typically, two polypeptides that are operatively linked are covalently attached through peptide bonds.

The term "quorum sensing signaling" or "quorum sensing" is intended to include the generation of a cellular signal in response to cell density. In one embodiment, quorum sensing signaling mediates the coordinated expression of specific genes. A "quorum sensing controlled gene" is any gene, the expression of which is regulated in a cell density dependent fashion. In a preferred embodiment, the expression of a quorum sensing controlled gene is modulated by a quorum sensing signal molecule, e.g., an autoinducer molecule (e.g., a homoserine lactone molecule). The term "quorum sensing signal molecule" is intended to include a molecule that transduces a quorum sensing signal and mediates the cellular response to cell density. In a preferred embodiment the quorum sensing signal molecule is a freely diffusible autoinducer molecule, e.g., a homoserine lactone molecule or analog thereof. In one embodiment, a quorum sensing controlled gene encodes a virulence factor. In another embodiment, a quorum sensing controlled gene encodes a protein or polypeptide that, either directly or indirectly, inhibits and/or antagonizes a bacterial host defense mechanism. In yet another embodiment, a quorum sensing controlled gene encodes a protein or polypeptide that regulates biofilm formation.

The term "regulatory sequences" is intended to include the DNA sequences that control the transcription of an adjacent gene. Gene regulatory sequences include, but are not limited to, promoter sequences that are found in the 5' region of a gene proximal to the transcription start site which bind RNA polymerase to initiate transcription. Gene regulatory sequences also include enhancer sequences which can function in either orientation and in any location with respect to a promoter, to modulate the utilization of a promoter, and other expression control elements (e.g., polyadenylation signals). Such regulatory sequences are described, for example, in Goeddel (1990) *Methods Enzymol.* 185:3–7. Transcriptional control elements include, but are not limited to, promoters, enhancers, and repressor and activator binding sites. The gene regulatory sequences of the present invention contain binding sites for transcriptional regulatory proteins. In one embodiment, a regulatory sequence includes a sequence that mediates quorum sensing controlled gene expression, e.g., a las box. In a preferred embodiment, gene regulatory sequences comprise sequences derived from the *Pseudomonas aeruginosa* genome which modulate quorum sensing controlled gene expression, e.g., SEQ ID NOs.:38 and 39. In another preferred embodiment, gene regulatory sequences comprise sequences (e.g., a genetic locus) derived from the *Pseudomonas aeruginosa* genome which modulate the expression of quorum sensing controlled genes, e.g., SEQ ID NOs.:1–36.

The term "reporter gene" or "indicator gene" generically refers to an expressible (e.g., able to be transcribed and (optionally) translated) DNA sequence which is expressed in response to the activity of a transcriptional regulatory protein. Indicator genes include unmodified endogenous genes of the host cell, modified endogenous genes, or a reporter gene of a heterologous construct, e.g., as part of a reporter gene construct. In a preferred embodiment, the level of expression of an indicator gene produces a detectable signal.

Reporter gene constructs are prepared by operatively linking an indicator gene with at least one transcriptional regulatory element. If only one transcriptional regulatory element is included, it is advantageously a regulatable promoter. In a preferred embodiment at least one of the selected transcriptional regulatory elements is directly or indirectly regulated by quorum sensing signals, whereby quorum sensing controlled gene expression can be monitored via transcription and/or translation of the reporter genes.

Many reporter genes and transcriptional regulatory elements are known to those of skill in the art and others may be identified or synthesized by methods known to those of skill in the art. Reporter genes include any gene that expresses a detectable gene product, which may be RNA or protein. Preferred reporter genes are those that are readily detectable. In one embodiment, an indicator gene of the present invention is comprised in the nucleic acid molecule in the form of a fusion gene (e.g., operatively linked) with a nucleotide sequence that includes regulatory sequences (e.g., quorum sensing transcriptional regulatory elements, e.g., a las box) derived from the *Pseudomonas aeruginosa* genome (e.g., SEQ ID NOs:38 and 39). In another embodiment, an indicator gene of the present invention is operatively linked to quorum sensing transcriptional regulatory sequences that regulate a quorum sensing controlled genetic locus derived from the *Pseudomonas aeruginosa* genome, e.g., a genetic locus comprising a nucleotide sequence set forth as SEQ ID NOs.: 1–36. In yet another embodiment, an indicator gene of the present invention is operatively linked to a nucleotide sequence comprising a quorum sensing controlled genetic locus derived from the *Pseudomonas aeruginosa* genome (e.g., SEQ ID NOs.:1–39). In certain embodiments of the invention, an indicator gene (e.g., a promoterless indicator gene) is contained in a transposable element.

The term "detecting a change in the detectable signal" is intended to include the detection of alterations in gene transcription of an indicator or reporter gene induced upon modulation of quorum sensing signaling. In certain embodiments, the reporter gene may provide a selection method such that cells in which the transcriptional regulatory protein activates transcription have a growth advantage. For example the reporter could enhance cell viability, relieve a cell nutritional requirement, and/or provide resistance to a drug. In other embodiments, the detection of an alteration in a signal produced by an indicator gene encompass assaying general, global changes to the cell such as changes in second messenger generation.

The amount of transcription from the reporter gene may be measured using any method known to those of skill in the art. For example, specific mRNA expression may be detected using Northern blots, or a specific protein product may be identified by a characteristic stain or an intrinsic activity. In preferred embodiments, the gene product of the reporter is detected by an intrinsic activity associated with that product. For instance, the reporter gene may encode a gene product that, by enzymatic activity, gives rise to a detection signal based on color, fluorescence, or lurninescence.

The amount of regulation of the indicator gene, e.g., expression of a reporter gene, is then compared to the amount of expression in a control cell. For example, the amount of transcription of an indicator gene may be compared between a cell in the absence of a test modulator molecule and an identical cell in the presence of a test modulator molecule.

As used interchangeably herein, the terms "transposon" and "transposable element" are intended to include a piece of DNA that can insert into and cut itself out of, genomic DNA of a particular host species. Transposons include mobile genetic elements (MGEs) containing insertion sequences and additional genetic sequences unrelated to insertion functions (for example, sequences encoding a reporter gene). Insertion sequence elements include sequences that are between 0.7 and 1.8 kb in size with termini approximately 10 to 40 base pairs in length with perfect or nearly perfect repeats. As used herein, a transposable element is operatively linked to the nucleotide sequence into which it is inserted. Transposable elements are well known in the art.

The present invention discloses a method for identifying modulators of quorum sensing signaling in bacteria, e.g., *Pseudomonas aeruginosa*. As described herein, the method of the invention comprises providing a cell which comprises a quorum sensing controlled gene, wherein the cell is responsive to a quorum sensing signal molecule such that a detectable signal is generated. A cell which responds to a quorum sensing signal molecule by generating a detectable signal is referred to herein as an "indicator cell" or a "reporter cell". In a preferred embodiment of the invention, the cell is a *P. aeruginosa* bacterial cell. In another preferred embodiment, the cell is from a mutant strain of *P. aeruginosa* which comprises a reporter gene operatively linked to a regulatory sequence of a quorum sensing controlled gene, wherein said mutant strain is responsive to a quorum sensing signal molecule, such that a detectable signal is generated. In yet another preferred embodiment, the cell is a mutant strain of *P. aeruginosa* which comprises a promoterless reporter gene inserted in the chromosome at a quorum sensing controlled genetic locus, e.g., a genetic locus comprising a nucleotide sequence set forth as SEQ ID NOs.:1–38, wherein said mutant strain is responsive to a quorum sensing signal molecule such that a detectable signal is generated by the reporter gene. In a preferred embodiment, the reporter gene is contained in a transposable element. In a further preferred embodiment, the cell is from a strain of *P. aeruginosa* in which lasI and rhlI are inactivated, such that the cell does not express the lasI and rhlI autoinducer synthases which are involved in the generation of quorum sensing signal molecules. A compound is identified as a modulator of quorum sensing signaling in bacteria by contacting the cell with a quorum sensing signal molecule in the presence and absence of a test compound and detecting a change in the detectable signal.

Quorum sensing signal molecules that are useful in the methods of the present invention include autoinducer compounds such as homoserine lactones, and analogs thereof (see Table 1). In certain embodiments, the quorum sensing signal molecule is either 3-oxo-C12-homoserine lactone or C4-HSL. In one embodiment, the cell does not express the quorum sensing signal molecule. For example, the cell may comprise a mutant strain of *Pseudomonas aeruginosa* wherein lasI and rhlI are inactivated. Therefore, the cell is contacted with an exogenous quorum sensing signal molecule, e.g., a recombinant or synthetic molecule. In another embodiment, the quorum sensing signal molecule is produced by a second cell (e.g., a prokaryotic or eukaryotic cell), which is co-incubated with the indicator cell. For example, an indicator cell which does not express a quorum sensing signal molecule can be co-incubated with a wild type strain of *Pseudomonas aeruginosa* which produces a quorum sensing signal molecule. Alternatively, the indicator strain which does not express a quorum sensing signal molecule is co-incubated with a second cell which has been transformed, or otherwise altered, such that it is able to express a quorum sensing signal molecule. In yet another embodiment, the quorum sensing signal molecule is expressed by the indicator strain.

Similarly, the test compound can be exogenously added to an indicator strain, produced by a second cell which is co-incubated with the indicator strain, or expressed by the indicator strain. Exemplary compounds which can be screened for activity include, but are not limited to, peptides, nucleic acids, carbohydrates, small organic molecules, and natural product extract libraries.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:45).

Examples of methods for the synthesis of molecular libraries can be found in the art, for example, in: DeWitt et al. (1993) *Proc. Natl. Acad Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angnew. Chem. Int. Ed. Engl.* 33:2059; Carell et al. (1994) *Angew Chem. Int. Ed. Engl.* 33:2061; and Gallop et al. (1994) *J. Med. Chem.* 37:1233.

Libraries of compounds may be presented in solution (e.g., Houghten (1992) Biotechniques 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Sci USA* 89:1865–1869) or on phage (Scott and Smith (1990) *Science* 249:386–390); (Devlin (1990) *Science* 249:404–406); (Cwirla et al. (1990) *Proc. Natl. Acad Sci. USA* 87:6378–6382); (Felici (1991) *J. Mol. Biol.* 222:301–310); (Ladner supra.).

In certain embodiments of the instant invention, the compounds tested are in the form of peptides from a peptide library. The peptide library may take the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached on the terminus of the thioredoxin protein, or, for short peptide libraries, inserted into the so-called active loop.

In one embodiment of the instant invention the cell further comprises a means for generating the detectable signal. For example, the cell may comprise a reporter gene, the transcription of which is regulated by a quorum sensing signal molecule. In a preferred embodiment, the reporter gene is operatively linked to a regulatory sequence of a quorum sensing controlled gene, e.g. a nucleotide sequence comprising at least one quorum sensing controlled regulatory element, e.g., a las box. In another embodiment, the reporter gene is operatively linked to a quorum sensing controlled genetic locus, e.g., a quorum sensing controlled gene, such that transcription of the indicator gene is responsive to quorum sensing signals. For example, in a preferred embodiment, a promoterless reporter gene is inserted into a quorum sensing controlled genetic locus derived from the genome of *P. aeruginosa*. Such quorum sensing controlled genetic loci, as described herein, include the loci in the *P. aeruginosa* genome which comprise the nucleotide sequences set forth as SEQ ID NOs.: 1–38. In another preferred embodiment, the promoterless reporter gene is contained in a transposable element that is inserted into a quorum sensing controlled genetic locus in the *P. aeruginosa* genome.

Examples of reporter genes include, but are not limited to, CAT (chloramphenicol acetyl transferase) (Alton and Vapnek (1979), *Nature* 282: 864–869), and other enzyme detection systems, such as beta-galactosidase (lacZ), firefly luciferase (deWet et al. (1987), Mol. Cell. Biol. 7:725–737); bacterial luciferase (Engebrecht and Silverman (1984), *PNAS* 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368), and horseradish peroxidase. In one preferred embodiment, the indicator gene is lacZ. In another preferred embodiment, the indicator gene is green fluorescent protein (U.S. Pat. No. 5,491,084; WO96/23898) or a variant thereof. A preferred variant is GFPmut2. Other reporter genes include ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, HIS1, HIS3, HIS4, HIS5, HOM3, HOM6, ILV1, ILV2, ILV5, INO 1, INO2, INO4, LEU1, LEU2, LEU4, LYS2, MAL, MEL, MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10.

In accordance with the methods of the invention, compounds which modulate quorum sensing singaling can be selected and identified. The ability of compounds to modulate quorum sensing signaling can be detected by up or down-regulation of the detection signal provided by the indicator gene. Any difference, e.g., a statistically significant difference, in the amount of transcription indicates that the test compound has in some manner altered the activity of quorum sensing signaling.

A modulator of quorum sensing signaling may act by inhibiting an enzyme involved in the synthesis of a quorum sensing signal molecule, by inhibiting reception of the quorum sensing signal molecule by the cell, or by scavenging the quorum sensing signal molecule. The term "scavenging" is meant to include the sequestration, chemical modification, or inactivation of a quorum sensing signal molecule such that it is no longer able to regulate quorum sensing gene control. After identifying certain test compounds as potential modulators of quorum sensing signaling, the practitioner of the subject assay will continue to test the efficacy and specificity of the selected compounds both in vitro and in vivo, e.g., in an assay for bacterial viability and/or pathogenecity.

In another aspect, the present invention discloses a method for identifying a quorum sensing controlled gene in bacteria, e.g., *Pseudomonas aeruginosa*. The method comprises providing a cell which is responsive to a quorum sensing signal molecule such that expression of a quorum sensing controlled gene is modulated, and wherein modulation of the expression of the quorum sensing controlled gene generates a detectable signal. The cell is contacted with a quorum sensing signal molecule and a change in the signal is detected to thereby identify a quorum sensing signaling controlled gene.

In one embodiment, the cell further comprises a means for generating the detectable signal, e.g., a reporter gene. For example, the cell may comprise a promoterless reporter gene that is operatively linked to a quorum sensing controlled genetic locus such that modulation of the expression of the quorum sensing controlled locus concurrently modulates transcription of the reporter gene. The position of the quorum sensing controlled genetic locus is then mapped based on the position of the reporter gene.

In a preferred embodiment of the invention, the cell is a *P. aeruginosa* bacterial cell. In another preferred embodiment, the cell is a mutant strain of *P. aeruginosa* which comprises a promoterless reporter gene inserted in the chromosome at a quorum sensing controlled genetic locus, e.g., a genetic locus comprising a nucleotide sequence set forth as SEQ ID NOs.:1–39, wherein said mutant strain is responsive to a quorum sensing signal molecule such that a detectable signal is generated by the reporter gene. In a preferred embodiment, the reporter gene is contained in a transposable element. In a further preferred embodiment, the cell is from a strain of *P. aeruginosa* in which lasI and rhlI are inactivated, such that the cell does not express the lasI and rhlI autoinducer synthases which are involved in the generation of quorum sensing signal molecules.

It is also to be understood that genomic sequences from a mutant bacterial strain (e.g., *P. aeruginosa*) in which a promoterless reporter gene (e.g., a reporter gene contained in a transposable element) has been inserted at a quorum sensing controlled locus, can be assayed in a heterologous cell that is responsive to a quorum sensing signal molecule such that quorum sensing signal transduction occurs. For exarnple, the genomic DNA of a strain of *P. aeruginosa* subjected to transposon mutagenesis, as described herein, can be engineered into a library, and transferred to another cell capable of quorum sensing signaling (e.g., a different species of gram negative bacteria), and assayed to identify a quorum sensing controlled gene.

In one embodiment, the cell is contacted with an exogenous quorum sensing signal molecule, e.g., a recombinant or synthetic molecule, as described herein. In another embodiment, the quorum sensing signal molecule is produced by a second cell (e.g., a prokaryotic or eukaryotic cell), which is co-incubated with the indicator cell. For example, an indicator cell which does not express a quorum sensing signal molecule can be co-incubated with a wild type strain of *Pseudomonas aeruginosa* which produces a quorum sensing signal molecule. Alternatively, the indicator strain which does not express a quorum sensing signal molecule is co-incubated with a second cell which has been transformed, or otherwise altered, such that it is able to express a quorum sensing signal molecule. In yet another embodiment, the quorum sensing signal molecule is expressed by the indicator strain.

Another aspect of the invention provides a mutant strain of *Pseudomonas aeruginosa* comprising a promoterless reporter gene inserted in a chromosome at a genetic locus comprising a nucleotide sequence set forth as SEQ ID NOs: 1–36, e.g., a quorum sensing controlled genetic locus. In one embodiment the reporter gene is contained in a transposable element. In another embodiment, the reporter gene is lacZ or GFP, or a variant thereof, e.g., GFPmut2. In yet another embodiment, lasI and rhlI are inactivated in the mutant strain of *P. aeruginosa*. The above-described cells are useful in the methods of the instant invention, as the cells are responsive to a quorum sensing signal molecule such that a detectable signal is generated by the reporter gene. These cells are also useful for studying the function of polypeptides encoded by the quorum sensing controlled loci comprising the nucleotide sequences set forth as SEQ ID NOs.:1–36.

Yet another aspect of the invention provides isolated nucleic acid molecules comprising a nucleotide sequence comprising a quorum sensing controlled genetic locus derived from the genome of *Pseudomonas aeruginosa* operatively linked to a reporter gene. In one embodiment, a reporter gene is operatively linked to a regulatory sequence derived from the genome of *P. aeruginosa*, wherein the regulatory sequence regulates a quorum sensing controlled genetic locus comprising a nucleotide sequence set forth as SEQ ID NO:1–36. In a preferred embodiment such regulatory sequences comprise at least one binding site for a quorum sensing controlled transcriptional regulatory factor (e.g., a transcriptional activator or repressor molecule) such that transcription of the reporter gene is responsive to a quorum sensing signal molecule and/or a modulator of quorum sensing signaling. In another embodiment, a reporter gene is operatively linked to a quorum sensing controlled genetic locus derived from the genome of *P. aeruginosa*, wherein the genetic locus comprises a nucleotide sequence set forth as SEQ ID NO:1–36. In yet another embodiment, a reporter gene is operatively linked to a nucleotide sequence which has at least 80%, and more preferably at least 85%, 90% or 95% identity to quorum sensing controlled genetic locus derived from the genome of *P. aeruginosa*, wherein the genetic locus comprises a nucleotide sequence set forth as SEQ ID NO:1–36. In a further embodiment, a reporter gene is operatively linked to a nucleotide sequence which hybridizes under stringent conditions to quorum sensing controlled genetic locus derived from the genome of *P. aeruginosa*, wherein the genetic locus comnprises a nucleotide sequence set forth as SEQ ID NO:1–36.

The term "isolated nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a CDNA molecule, can be substantially free of other cellular material, or culture medium when produced by recombinant techniques, or substantially free of chemical precursors or other chemicals when chemically synthesized. As used interchangeably herein, the terms "nucleic acid molecule" and "polynucleotide" are intended to include DNA molecules (e.g., cDNA or genomic DNA) and RNA molecules (e.g., rRNA) and analogs of the DNA or RNA generated using nucleotide analogs. The nucleic acid molecule can be single-stranded or double-stranded, but preferably is double-stranded DNA. The term "DNA" refers to deoxyribonucleic acid whether single- or double-stranded. As used herein, the terms "gene" and "recombinant gene" refer to nucleic acid molecules which include an open reading frame encoding a protein, preferably a quoumn sensing controlled protein, and can further include non-coding regulatory sequences, and introns.

The present invention includes polynucleotides capable of hybridizing under stringent conditions, preferably highly stringent conditions, to the polynucleotides described herein (e.g., a quorum sensing controlled genetic locus, e.g., SEQ ID NOs.:1–36). As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory*

Manual, Sam brook et al., Cold Spring Harbor Press, Cold Spring Harbor, N.Y. (1989), chapters 7, 9, and 11. A preferred, non-limiting example of stringent hybridization conditions includes hybridization in 4×sodium chloride/sodium citrate (SSC), at about 65–70° C. (or alternatively hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or alternatively hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$ where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5 M $NaH_2PO_4$, 7% SDS at about 65° C., followed by one or more washes at 0.02 M $NaH_2PO_4$, 1% SDS at 65° C. (see e.g., Church and Gilbert (1984) Proc. Natl. Acad. Sci. USA 81:1991–1995), or alternatively 0.2×SSC, 1% SDS.

The invention further encompasses nucleic acid molecules that differ from the quorum sensing controlled genetic loci described herein, e.g., the nucleotide sequences shown in SEQ ID NO:1–36. Accordingly, the invention also includes variants, e.g., allelic variants, of the disclosed polynucleotides or proteins; that is naturally occuring and non-naturally occurring alternative forms of the isolated polynucleotide which may also encode proteins which are identical, homologous or related to that encoded by the polynucleotides of the invention.

Nucleic acid variants can be naturally occurring, such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). Allelic variants result, for example, from DNA sequence polymorphisms within a population (e.g., a bacterial population) that lead to changes in the nucleic acid sequences of quorum sensing controlled genetic loci.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90% or 95% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48):444–453 (1970)) algorithm which has been incorporated into the GAP™ program in the GCGT™ software package (available at the ACCELRYS™ website), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP™ program in the GCG™ software package (available at the ACCELRYS™ website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci., 4:11–17 (1988) which has been incorporated into the ALIGN™ program (version 2.0) (available at the ALIGN™ website), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST™ and XBLAST™ programs (version 2.0) of Altschul, et al. (1990) J. Mol. Biol. 215:403–10. BLAST™ nucleotide searches can be performed with the NBLAST program, score=100, wordlength=12 to obtain nucleotide sequences homologous to nucleic acid molecules of the invention. BLAST™ protein searches can be performed with the XBLAST™ program, score=50, wordlength=3 to obtain amino acid sequences homologous to protein molecules of the invention. To obtain gapped alignments for comparison purposes, Gapped BLAST™ can be utilized as described in Altschul et al., (1997) *Nucleic Acids Res.* 25(17):3389–3402. When utilizing BLAST™ and Gapped BLAST™ programs, the default parameters of the respective programs (e.g., XBLAST™ and NBLAST™) can be used. See the National Center for Biotechnology website. Additionally, the "Clustal" method (Higgins and Sharp, Gene, 73:237–44, 1988) and "Megalign" program (Clewley and Arnold, *Methods Mol. Biol,* 70:119–29, 1997) can be used to align sequences and determine similarity, identity, or homology.

Accordingly, the present invention also discloses recombinant vector constructs and recombinant host cells transformed with said constructs.

As used interchangeably herein, a "cell" or a "host cell" includes any cultivatable cell that can be modified by the introduction of heterologous DNA. As used herein, "heterologous DNA", a "heterologous gene" or "heterologous polynucleotide sequence" is defined in relation to the cell or organism harboring such a nucleic acid or gene. A heterologous DNA sequence includes a sequence that is not naturally found in the host cell or organism, e.g., a sequence which is native to a cell type or species of organism other than the host cell or organism. Heterologous DNA also includes mutated endogenous genetic sequences, for example, as such sequences are not naturally found in the host cell or organism. Preferably, a host cell is one in which a quorum sensing signal molecule, e.g, an autoinducer molecule, initiates a quorum sensing signaling response which includes the regulation of target quorum sensing controlled genetic sequences. The choice of an appropriate host cell will also be influenced by the choice of detection signal. For example, reporter constructs, as described herein, can provide a selectable or screenable trait upon activation or inhibition of gene transcription in response to a quorum sensing signaling event; in order to achieve optimal selection or screening, the host cell phenotype will be considered.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such ivectors are referred to herein as "expression vectors". Expression systems for both prokaryotic and eukaryotic cells are described in, for example, chapters 16 and 17 of Sambrook, J. et al. *Molecular Cloning: A Laboratory Manual.* $2^{nd}$, ed., Cold Spring Harbor Laboratory, Cold Spring Harbor Laboratory Press, Cold Spring Harbor, N.Y., 1989.

In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transcriptional regulatory protein but is inactivated in terms of its ability to replicate in a normal lytic viral life cycle. See for example Berkner et al. (1988) *Bio Techniques* 6:616; Rosenfeld et al. (1991) *Science* 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. ((1985) *Mol. Cell. Biol.* 5:3251–3260) can be used.

In general, it may be desirable that an expression vector be capable of replication in the host cell. Heterologous DNA may be integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, N.Y., 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The vectors of the subject invention may be transformed into an appropriate cellular host for use in the methods of the invention.

As used interchangeably herein, a "cell" or a "host cell " includes any cultivatable cell that can be modified by the introduction of heterologous DNA. As used herein, "heterologous DNA", a "heterologous gene" or "heterologous polynucleotide sequence" is defined in relation to the cell or organism harboring such a nucleic acid or gene. A heterologous DNA sequence includes a sequence that is not naturally found in the host cell or organism, e.g., a sequence which is native to a cell type or species of organism other than the host cell or organism. Heterologous DNA also includes mutated endogenous genetic sequences, for example, as such sequences are not naturally found in the host cell or organism. Preferably, a host cell is one in which a quorum sensing signal molecule, e.g, an autoinducer molecule, initiates a quorum sensing signaling response which includes the regulation of target quorum sensing controlled genetic sequences. The choice of an appropriate host cell will also be influenced by the choice of detection signal. For example, reporter constructs, as described herein, can provide a selectable or screenable trait upon activation or inhibition of gene transcription in response to a quorum sensing signaling event; in order to achieve optimal selection or screening, the host cell phenotype will be considered.

A host cell of the present invention includes prokaryotic cells and eukaryotic cells. Prokaryotes include gram negative or gram positive organisms, for example, *E. Coli* or

*Bacilli.* Suitable prokaryotic host cells for transformation include, for example, *E. coli, Bacillus subtilis, Salmonella typhimurium,* and various other species within the genera *Pseudomonas, Streptomyces,* and *Staphylococcus.* In a preferred embodiment, a host cell of the invention is a mutant strain of *P. aeruginosa* in which lasI and rhlI are inactivated.

Eukaryotic cells include, but are not limited to, yeast cells, plant cells, fungal cells, insect cells (e.g., baculovirus), mammalian cells, and cells of parasitic organisms, e.g., trypanosomes. Mammalian host cell culture systems include established cell lines such as COS cells, L cells, 3T3 cells, Chinese hamster ovary (CHO) cells, embryonic stem cells, and HeLa cells. Other suitable host cells are known to those skilled in the art.

DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual 2$^{nd}$, ed,* Cold Spring Harbor Laboratory, Cold Spring Harbor Laboratory Press, Cold Spring Harbor, N.Y., 1989), and other laboratory manuals.

Host cells comprising an isolated nucleic acid molecule of the invention (e.g., a quorum sensing controlled genetic locus operatively linked to a reporter gene) can be used in the methods of the instant invention to identify a modulator of quorum sensing signaling in bacteria.

EXEMPLIFICATION

The invention is further illustrated by the following examples which should not be construed as limiting.

EXAMPLE 1

Identification of Quorum Sensing Genes of *P. Aeruginosa*

Materials and Methods

Bacteriol Strains, Plasmids, and Media. The bacterial strains and plasmids used in this example are listed in Table 2.

*E. coli* and *P. aeruginosa* were routinely grown in Luria-Bertani (LB) broth or LB agar (Sambrook, et al. (1989) *Molecular Cloning: a Laboratory Manual.* (Cold Spring Harbor Laboratory, Cold Spring Harbor, N.Y.)), supplemented with antimicrobial agents when necessary. The antimicrobial agents were used at the following concentrations: $HgCl_2$, 15 µg/ml in agar and 7.5 µg/ml in broth; nalidixic acid 20 µg/ml; carbenicillin, 300 µg/ml; tetracycline, 50 µg/ml for *P. aeruginosa* and 20 µg/ml for *E. coli*; and gentamicin, 100 µg/ml for *P. aeruginosa* and 15 µg/ml for *E. coli*. Synthetic acyl-HSL concentrations were 2 µM for $3OC_{12}$-HSL and 5 µM for $C_4$-HSL, and 5-bromo4-chloro-3-indolyl-β-D-galactopyranoside (X-Gal) was used at 50 µg/ml.

DNA Manipulations and Plasmid Constructions. DNA treatment with modifying enzymes and restriction endonucleases, ligation of DNA fragments with T4 ligase, and transformation of *E. coli* were performed according to standard methods (Ausubel, F. et al. (1997) *Short Protocols in Molecular Biology.* (John Wiley & Sons, Inc., New York, N.Y.)). Plasmid isolation was performed using QIAprep spin miniprep kits (Qiagen Inc.) and DNA fragments were excised and purified from agarose gels using GeneClean spin kits (Bio101 Corp.). DNA was sequenced at the University of Iowa DNA core facility by using standard automated sequencing technology.

To construct pMW10, the pBR322 tetA(C) gene-containing ClaI-NotI DNA fragment in pJPP4 was replaced with a tetA(B)-containing BstB1-NotI fragment from Tn10. It was necessary to use tetA(B) rather than tetA(C) to inactivate lasI because the tetA(C) gene from pBR322 was a hot spot for Tn5::B22 mutagenesis (Berg, D. E. et al. (1983) *Genetics* 105, 813–828).

To construct pMW300 a 1.6-kb SmaI fragment from pGMΩ1 that contained the aacC1 gene (encoding gentamicin acetyltransferase-3-1) was cloned into EagI digested pTL61T, which had been polished with T4 polymerase. The resulting plasmid pTL61T-GMΩ1 was digested with SmaI and MscI to release a 6.5-kb lacZ-aacC1 fragment. A

TABLE 2

| Bacterial strains and plasmids | | |
|---|---|---|
| Strain or plasmid | Relevant characteristics | Source (reference) |
| Strains | | |
| *P. aeruginosa* PAO1 | Parental strain | (1) |
| *P. aeruginosa* PDO100 | ΔrhlI::Tn501 derivative of PAO1, Hg$^r$ | (2) |
| *P. aeruginosa* PAO-MW1 | ΔlasI, ΔrhlI derivative of PDO100, Hg$^r$, Tc$^r$ | This study |
| *P. aeruginosa* PAO-MW10 | lasB::lacZ chromosomal insertion in PAO-MW1 | This study |
| *E. coli* DH5α | F$^-$φ80ΔlacZ, ΔM15, Δ(lacZYA-argF)U169, endA1, recA1, hsdR17, deoR, gyrA96, thi-1 relA1, supE44 | (3) |
| *E. coli* HB101 | F$^-$mcrB, mrr hsdS20, recA13, leuB6, ara-14 proA2, lacY1, galK2, xyl-5, mtl-1, rpsL20 (Sm$^r$), supE44 | (3) |
| *E. coli* SY327 λpir | (λpir), Δ(lac pro), argE(Am), rif, nlA, recA56 | (4) |
| *E. coli* S17-1 | thi, pro, hsdR, recA, RP4-2 (Tet::Mu) (Km::Tn7) | (5) |
| Plasmids | | |
| pJPP4 | oriR6K, mobRP4, ΔlasI, Tc$^r$, Ap$^r$ | (6) |
| pTL61T | lacZ transcriptional fusion vector, Ap$^r$ | (7) |
| pGMΩ1 | Contains aac1 flanked by transcriptional and translational stops, Gm$^r$ | (8) |

TABLE 2-continued

Bacterial strains and plasmids

| Strain or plasmid | Relevant characteristics | Source (reference) |
| --- | --- | --- |
| pTL61T-GMΩ1 | pTL61T with aac1 gene from pGMΩ1 upstream of lacZ, Ap$^r$, Gm$^r$ | This study |
| pMW100 | pJPP4 with 2.7-kb tetA(B) from Tn10 in place of the pBR322 tetA(C), Tc$^r$, Ap$^r$ | This study |
| pRK2013 | ori (ColE1), tra$^+$, (RK2)Km$^r$ | (9) |
| pSUP102 | pACYC184 carrying mobRP4, Cm$^r$, Tc$^r$ | (10) |
| pSUP102-lasB | pSUP102 carrying lasB on a 3.1-kb *P. aeruginosa* chromosomal DNA fragment, Cm$^r$, Tc$^r$ | This study |
| pMW300 | pSUP102-lasB containing lacZ-aac1 from pTL61T-GMΩ1 (lasB-lacZ transcriptional fusion knockout plasmid), Cm$^r$, Gm$^r$ | This study |
| pTn5-B22 | pSUP102 with Tn5-B22 ('lacZ), Gm$^r$ | (28) |

Abbreviations for antibiotics are as follows: kanamycin, Km; gentamicin, Gm; ampicillin, Ap; tetracycline, Tc; streptomycin, Sm.

3.1-kb *P. aeruginosa* PAO1chromosomal DNA fragment containing the lasB gene was amplified by PCR using the EXPAND™ Long Template PCR System (Boehringer Mannheim). This fragment was cloned into BamHI-digested pSUP102. The resulting plasmid, pSUP102-lasB was digested with NotI, polished with T4 polymerase and ligated with the 6.5-kb lacZ-aacCl fragment from pTL61T-GMΩ1 to generate pMW300. The promoterless lacZ gene in pMW300 is 549 nucleotides form the start of the lasB ORF, it is flanked by 1.5 kb upstream and 1.6 kb downstream *P. aeruginosa* DNA, and it contains the p15A ori, which does not support replication in *P. aeruginosa*.

Construction of *P. aeruginosa* Mutants. A lasI, rhlI mutant strain of *P. aeruginosa* PAO-MWI was generated by insertional mutagenesis of lasI in the rhlI deletion mutant, PDO100. For insertional mutagenesis, the lasI::tetA(B) plasmid, pMW100 was mobilized from *E. coli* SY327 λpir into PDO100 by triparental mating with the help of *E. coli* HB101 containing pRK2013. Because pMW100 has a λpir-dependent origin of replication, it cannot replicate in *P. aeruginosa*. A tetracycline-resistant, carbenicillin-sensitive exconjugant was selected, which was shown by a Southern blot analysis to contain lasI:tetA but not lasI or pMW100. To confirm the inactivation of the chromosomal lasI in this strain, PAO-MW1, the amount of 3OC$_{12}$-HSL in the fluid from a stationary phase culture (optical density at 600 nm, 5) was assessed by a standard bioassay (Pearson, J. P. et al. (1994) *PNAS*, 91, 197–201). No detectable 3-OC$_{12}$-HSL (<5 nM) was found.

A mutant strain, *P. aeruginosa* PAO-MW 10, which contains a lacZ reporter in the chromosomal lasB gene was constructed by introduction of pMW300 into PAO-MW1 by triparental mating as described above. Exconjugants resistant to gentamicin and sensitive to chloramphenicol were selected as potential recombinants. Southern blotting of chromosomal DNA with lasB and lacZ probes indicated that the pMW300 lasB-lacZ insertion had replaced the wt lasB gene.

Southern Blotting. Chromosomal DNA was prepared using the QIAMP™ tissue kit (Qiagen Inc.). Approximately 2 µg of chromosomal DNA was digested with restriction endonucleases, separated on a 0.7% agarose gel, and transferred to a nylon membrane according to standard methods (Ausubel, F. et al. (1997) *Short Protocols in Molecular Biology*. (John Wiley & Sons, Inc., New York, N.Y.). DNA probes were generated using digoxigenin-11-dUTP by random primed DNA labeling or PCR. The Southern blots were visualized using the GENIUS™ system as outlined by the manufacturer (Boehringer Mannheim).

Tn5 Mutagenesis. Tn5::B22, which carries a promoterless lacZ gene, was used to mutagenize *P. aeruginosa* PAO-MW1 (Simon, R. et al. (1989) *Gene* 80, 161–169). Equal volumes of a late logarithmic phase culture of *E. coli* S17-1 carrying pTn5::B22 grown at 30° C. with shaking and a late logarithmic phase culture of *P. aeruginosa* PAO-MWI grown at 42° C. without shaking were mixed. The mixture was centrifuged at 6000×g for 10 minutes at room temperature, suspended in LB (5% of the original volume), and spread onto LB plates (100 µper plate). After 16 to 24 hours at 30° C., the cells on each plate were suspended in 500 µl LB and 100 µl volumes were spread onto LB agar plates containing HgCl$_2$, gentamicin, tetracycline and nalidixic acid. The nalidixic acid prevents growth of *E. coli* but not *P. aeruginosa*. After 48 to 72 hours at 30° C., 20 colonies were selected from each mating and grown on LB selection agar plates containing X-gal. Ten of the 20 were picked for further study. The colonies picked showed a range in the intensity of the blue color on the X-gal plates. In this way, the selection of siblings in a mating were minimized. A Southern blot using a probe to lacZ was performed on 20 randomly chosen transconjugants indicated that the Tn5 insertion in each was in a unique location.

The Screen for qsc Fusions. A microtiter dish assay was used to identify mutants showing acyl-HSL-dependent β-galactosidase expression (quorum sensing-controlled or qsc mutants). Each transconjugant was grown in four separate wells containing LB broth without added autoinducer, with added 3OC$_{12}$-HSL, C$_4$-HSL, or both 3OC$_{12}$-HSL and C$_4$-HSL for 12–16 hours at 37° C. Inocula were 10 µl of an overnight culture and final culture volumes were 70 µl. The β-galactosidase activity of cells in each microtiter dish well was measured in microtiter dishes with a luminescence assay (Tropix) Luminescence was measured with a Lucy I microtiter dish luminometer (Anthos).

Patterns of Acyl-HSL Induction of β-galactosidase Activity in qsc Mutants. The pattern of β-galactosidase expression was examined in response to acyl-HSLs in each of 47 qsc mutants identified in the initial screen. Each mutant was grown in 1 ml of MOPS (50 mM, pH 7.0) buffered LB broth containing one, the other, both, or neither acyl-HSL signal in an 18 mm culture tube at 37° C. with shaking. A mid-logarithmic phase culture was used as an inoculum and initial optical densities (ODs) at 600 nm were 0.1. Growth was monitored as OD at 600 nm and β-galactosidase activity was measured in 0.1 ml samples taken at 0, 2, 5, and 9 hours after inoculation.

DNA Sequencing and Sequence Analysis. To identify DNA sequences flanking Tn5::B22 insertions, arbitrary PCR was performed with primers and conditions as described (Caetano-Annoles, G. (1993) *PCR Methods Appl.* 3, 85–92; O'Toole, G. A. et al. (1998) *Mol. Microbiol.* 28, 449–461). Tn5 flanking sequences that could not be identified using arbitrary PCR were cloned. For cloning, 3 μg of chromosomal DNA was digested with EcoRI and ligated with EcoRI-digested, phosphatase treated pBP22. *E. coli* DH5α was transformed by electroporation with the ligation mixtures and lasmids from gentamicin resistant colonies were used for sequencing Tn5-flanking DNA.

DNA sequences flanking Tn5-B22 insertions were located on the *P. aeruginosa* PAO1 chromosome by searching the chromosomal database at the *P. aeruginosa* Genome Project web site. The ORFs containing the insertions are those described at the web site. Functional coupling from the Argonne National Labs WIT website, sequence analysis, and expression patterns of the qsc mutants were used to identify potential operons (Overbeek, R. et al. (1999) *PNAS* 96, 2896–2901).

Results

Identification of *Pseudomonas aeruginosa* qsc Genes. Seven thousand Tn5::B22 mutants of *P. aeruginosa* PAO-MW1 were screened. Tn5::B22 contains a promoterless lacZ. *P. aeruginosa* PAO-MW1 is a lasI, rhlI mutant that does not make acyl-HSL signals. Thus, transcription of the Tn5::B22 lacZ in a qsc gene was expected to respond to an acyl-HSL signal. The screen involved growth of each mutant in a complex medium in a microtiter dish well with no added acyl-HSL, $3OC_{12}$-HSL, $C_4$-HSL, or both $3OC_{12}$-HSL and $C_4$-HSL. After 12–16 hours, β-galactosidase activity in each culture was measured. Two hundred-seventy mutants showed greater than 2 fold stimulation of β-galactosidase activity in response to either or both acyl-HSL. Of these, 70 showed a greater than 5-fold stimulation of β-galactosidase activity in response to either or both acyl-HSL, and were studied further. Each mutant was grown with shaking in culture tubes and 47 showed a reproducible greater than 5-fold stimulation of β-galactosidase activity in response to either or both of the acyl-HSL signals. These were considered to have Tn5::B22 insertions in qsc genes. It was shown by a Southern blot analysis with a lacZ probe that each mutant contained a single Tn5::B22 insertion.

Responses of qsc Mutants to Acyl-HSL Signals. For cultures of each of the 47 qsc mutants, β-galactosidase activity was measured at different times after addition of acyl-HSL signals. The basal levels of β-galactosidase varied depending on the mutant. The responses to the acyl-HSL signals could be grouped into 4 general classes based on which of the two signals was required for activation of lacZ, and whether the response to the signal(s) occurred immediately or was delayed until stationary phase. A response was considered immediate if there was a 5-fold or greater response within 2 hours of acyl-HSL addition (the optical densities(ODs) of the cultures ranged from 0.5–0.7 at 2 hours). A response was considered delayed or late if there was <5-fold induction at 2 hours but greater than 5-fold induction of β-galactosidase at 5 hours or later (ODs of 2 or greater). In some strains activation of lacZ required $3OC_{12}$-HSL, others required both $3OC_{12}$-HSL and $C_4$-HSL for full activation of lacZ. A number of strains responded to either signal alone but showed a much greater response with both $3OC_{12}$-HSL and $C_4$-HSL. None of the mutants responded well to $C_4$-HSL alone (Table 3). This was expected because expression of RhlR, which is required for a response to $C_4$-HSL is dependent on $3OC_{12}$-HSL (Pesci, E. C. et al. (1997) *J. Bacteriol.* 179, 3127–3132). Therefore at least some of the insertions exhibiting a response to both acyl-HSLs may be responding to the rhl system, which requires activation by the las system.

Figure 2:
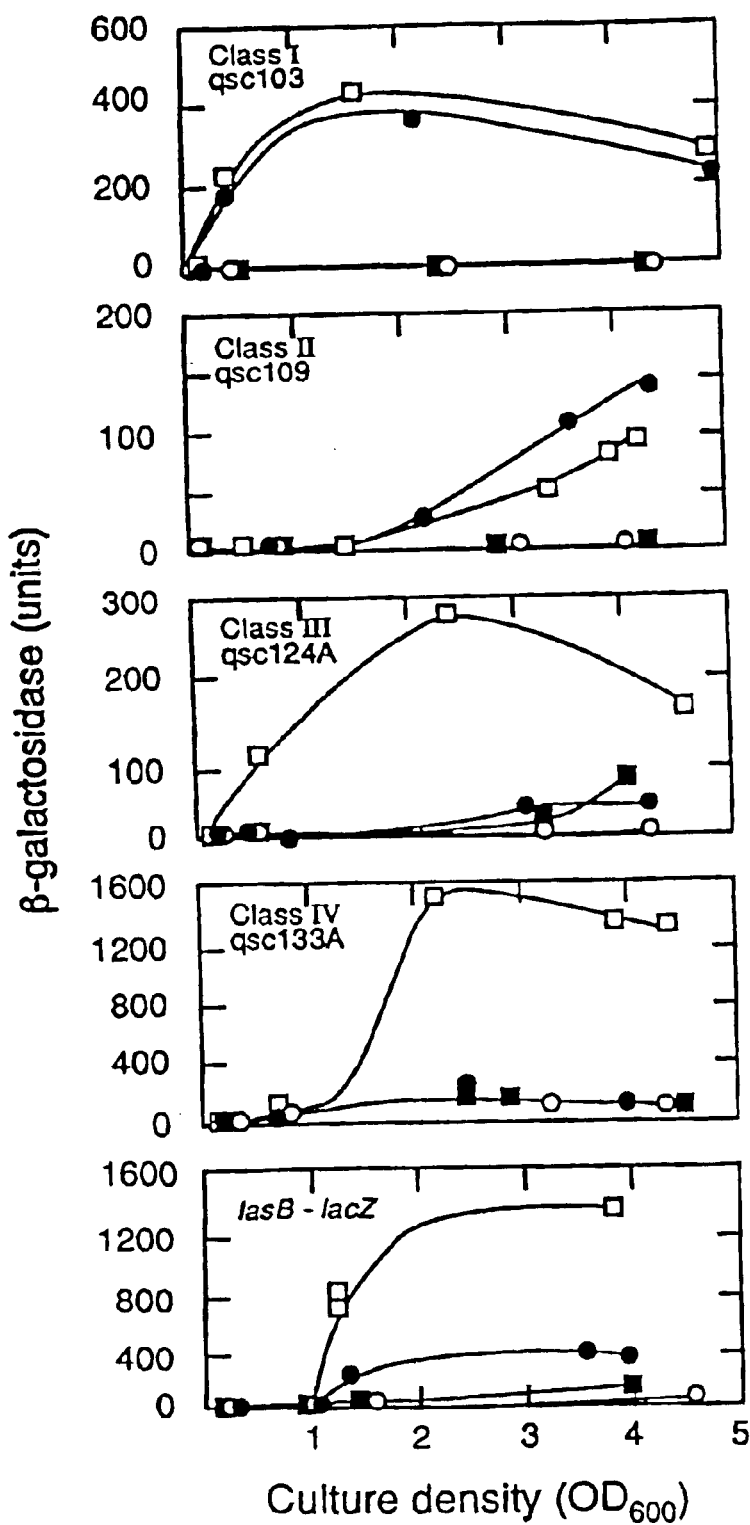
FIG. 2 depicts patterns of β-galactosidase expression in representative qsc mutants and in a strain with a lasB::lacZ chromosomal fusion generated by site-specific mutation. Units of β-galactosidase are given as a function of culture density for cells grown without added signal molecules (○), with added $3OC_{12}$-HSL (●), with added $C_4$-HSL (■), or with both signals added (□).

Class I mutants responded to $3OC_{12}$-HSL immediately, Class II responded to $3OC_{12}$-HSL late, Class III respond best to both signals early, and Class IV to both signals late. There were 9 Class I, 11 Class II, 18 Class III, and 9 Class IV mutants. FIG. 2 shows responses of representative members of each class to acyl-HSLs. Generally, most early genes (Class I and III genes) showed a much greater induction than most late genes (Class II and IV). Many of the Class III mutants showed some response to either signal alone but showed a greater response in the presence of both signals (Table 3 and FIG. 2).

Identity and Analysis of qsc Genes. The Tn5-B22-marked qsc genes were identified by coupling arbitrary PCR or transposon cloning with DNA sequencing. The sequences were located in the *P. aeruginosa* PAO1 chromosome by searching the *Pseudomonas aeruginosa* Genome Project web site (the *Pseudomonas* Genome Project website). To confirm the locations of the Tn5-B22 insertions in each qsc mutant, a Southern blot analysis was performed with Tn5-B22 as a probe. The sizes of Tn5-B22 restriction fragments were in agreement with those predicted based on the *P. aeruginosa* genomic DNA sequence (data not shown). The 47 qsc mutations mapped in or adjacent to 39 different open reading frames (ORFs). For example FIG. 3 depicts the nucleic acid sequence of the quorum sensing controlled locus on the *P. aeruginosa* chromosome mapped in the *P. aeruginosa* mutant strain qsc 102.

TABLE 3

Quorum sensing-controlled genes in *Pseudomonas aeruginosa*

| Classification | Identity[a] | Signal response[b] $3OC_{12}$-HSL | $C_4$-HSL | Both | Genomic Position[e] |
|---|---|---|---|---|---|
| Class I | | | | | |
| qsc100 | Peptide synthetase | 65 | 3 | 69 | 5801998 |
| qsc101 | No match | 145 | 1 | 184 | 7730 |
| qsc102 | No match | 350 | 1 | 400 | 5547 |
| qsc103 | No match | 85 | 1 | 95 | 3961920 |
| qsc104 | Polyamine binding protein | 7 | 2 | 8 | 5402505 |
| qsc105 | FAD-binding protein | 40 | 1 | 42 | 5410045 |
| qsc106A&B | No match | 9 | 1 | 10 | 2870317 |
| qsc107 | No match | 44 | 2 | 50 | 5799641 |
| Class II | | | | | |
| qsc108 | ORF 5 | 13 | 1 | 7 | 5617382 |
| qsc109 | Bacitracin synthetase 3 | 13 | 1 | 8 | 5651872 |

TABLE 3-continued

Quorum sensing-controlled genes in *Pseudomonas aeruginosa*

| Classification | Identity[a] | 3OC$_{12}$-HSL | Signal response[b] C$_4$-HSL | Both | Genomic Position[e] |
|---|---|---|---|---|---|
| qsc110A&B | Pyoverdine synthetase D | 10 | 1 | 7 | 5661697 |
| qsc111 | Pyoverdine synthetase D | 11 | 1 | 7 | 5666282 |
| qsc112A&B | Aculeacin A acylase | 15 | 1 | 12 | 5701004 |
| qsc113 | Trransmembrane protein | 5 | 1 | 5 | 3771157 |
| qsc114[c] | No match | 9 | 1 | 7 | 5209051 |
| qsc115[d] | No match | 4 | 1 | 5 | 1941557 |
| qsc116 | No match | 5 | 1 | 5 | 1138940 |
| Class III | | | | | |
| qcs117[d] | ACP-like protein | 22 | 22 | 186 | 41430 |
| qsc118 | RhlI | 38 | 14 | 70 | 4447967 |
| qsc119 | RhlB | 9 | 7 | 100 | 4446918 |
| qsc120 | Chloramphenicol resistance | 3 | 7 | 24 | 4592102 |
| qsc121 | 3-Oxoacyl ACP synthase | 13 | 27 | 105 | 4594988 |
| qsc122A&B | Cytochrome p450 | 2 | 10 | 90 | 4595538 |
| qsc123 | 9-Cis retinol dehydrogenase | 14 | 28 | 96 | 4597340 |
| qsc124A&B | Pyoverdine synthetase D | 35 | 50 | 148 | 4598281 |
| qsc125 | Zeaxanthin synthesis | 20 | 65 | 140 | 4600099 |
| qsc126 | Pristanimycin I synthase 3 & 4 | 3 | 5 | 24 | 4603518 |
| qsc127[c] | No match | 5 | 2 | 15 | 4608787 |
| qsc128 | Hydrogen cyanide synthase HcnB | 19 | 12 | 42 | 5924799 |
| qsc129A&B | Cellulose binding protein p40 | 15 | 1 | 100 | 1141723 |
| qsc130 | glc operon transcriptional activator | 5 | 1 | 14 | 2313744 |
| qsc131 | PhzC | 50 | 168 | 742 | 1110 |
| Class IV | | | | | |
| qsc132A&B | Unknown (*B. pertusis*) | 1 | 1 | 40 | 3616599 |
| qsc133A&B | AcrB | 1 | 1 | 9 | 3628342 |
| qsc134 | Saframycin Mx1 synthetase A | 6 | 1 | 28 | 3781254 |
| qsc135 | Cytochrome C precursor | 3 | 1 | 6 | 4942182 |
| qtc136[c] | No match | 7 | 3 | 45 | 851491 |
| qsc137 | Asparagine synthetase | 1 | 1 | 10 | 2007007 |
| qsc138 | No match | 3 | 5 | 32 | 2459178 |

[a]The bold letters indicate matches were to known *P. aeruginosa* genes.
[b]The signal response is given as β-galactosidase activity in cells grown in the presence of the indicated signal(s) divided by the β-galactosidase activity of cells grown in the absence of added signals. Maximum responses are indicated.
[c]The lacZ insertions in these strains are in the opposite orientation of the ORFs described in the *P. aeruginosa* Genome Project web site. The insertions are which in locations with no reported identity are been indicated.
[d]Insertions do not lie in but are near the putative ORFs indicated. In qsc117 the insertion is 129 bp downstream of the ACP ORF and interrupts a potential rho-independent transcription terminator. The qsc115 insertion is 60 bp upstream of the ORF listed in Materials and Methods.
[e]Genomic position as identified using sequence information described in the *P. aeruginosa* Genome Project web site (Jul. 15, 1999 release).

The genomic sequences comprising the ORFs in Table 3 are described in the *Pseudomonas aeruginosa* Genome Sequencing Project web site, as detailed in Table 4.

Only 2 genes were identified that already were known to be controlled by quorum sensing, rhlI and rhlB. Several other genes potentially involved in processes known to be regulated by quorum sensing were also identified including phzC (phenazine synthesis), a putative cyanide synthesis gene (related to the *Pseudomonas fluorescens* hcnB), and ORF 5 (pyoverdine synthesis) (Latifi, A. et al. (1995) *Mol. Microbiol.* 17, 333–344; Cunliffe, H. E. et al. (1995) *J. Bacteriol.* 177, 2744–2750). Interestingly, lasB was not identified by the assay, yet the LasI-LasR quorum sensing system was originally described as regulating lasB (Ganbello, M. J. et al. (1991) *J. Bacteriol.* 173, 3000–3009). A lasB-lacZ chromosomal fision in *P. aeruginosa* PAO-MW1 was constructed, so that regulation of lasB by quorum sensing could be compared to the genes identified by the assay. The lasB-lacZ fusion only responded slightly to 3OC$_{12}$-HSL (3-fold stimulation). The full response (12–13-fold over background) required both C$_4$-HSL and 3OC$_{12}$-HSL, and the response was late (FIG. 2). Thus, lasB shows the characteristics of a Class IV gene.

Some of the qsc mutants had obvious phenotypes. Unlike the parent, on LB agar, colonies of the Class II mutants qsc 108, 109, 110A and B, and 111 were not fluorescent. Because pyoverdine is a fluorescent pigment, and because the qsc110 and 111 mutations were in genes coding for pyoverdine synthetase-like proteins, it was suspected that these mutations define a region involved in pyoverdine synthesis. The insertion in qsc131 is in phzC which is required for pyocyanin synthesis. Although the parent strain produced a blue pigment in LB broth, qsc131 did not. The two qsc132 mutants also did not produce detectable levels of pyocyanin but did produce a water-soluble red pigment.

Figure 4:
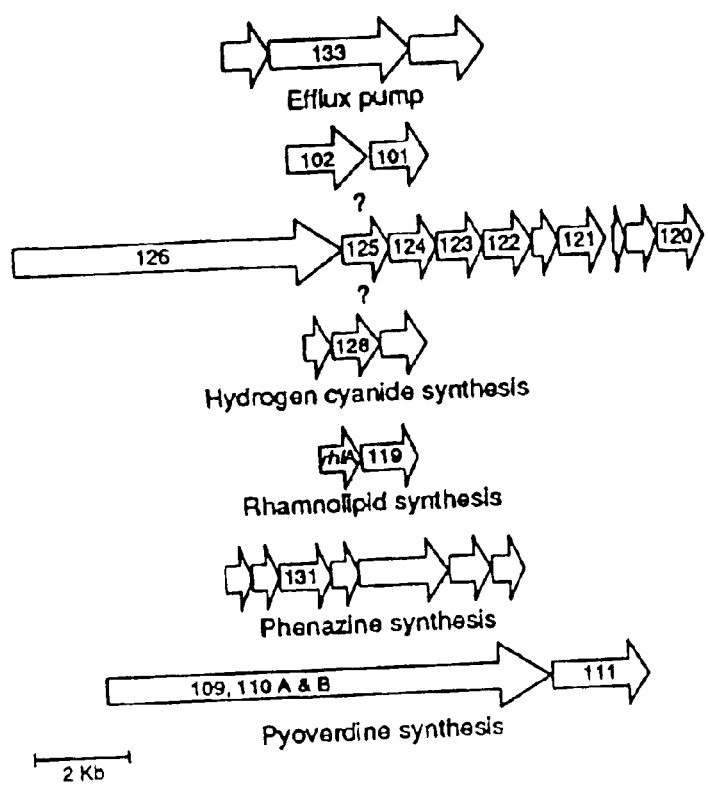
FIG. 4 depicts putative qsc operons. Open reading frames (ORFs) are indicated by the arrows. ORFs discovered in the qsc screen are indicated by their qsc number.

Functional coupling and sequence analysis were used to identify 7 putative qsc operons, one of which is the previously described rhlAB operon (FIG. 4). Functional coupling will not organize genes encoding polypeptides without known relatives into operons, and organization of genes in an operon was disallowed in cases where there was greater than 250 bp of intervening sequence between two adjacent ORFs. The

TABLE 4

ORFs of quorum sensing-controlled genes in *Pseudomonas aeruginosa*

| QSC | Insertion Jul. 15, 1999 release | Insertion Dec. 15, 1999 release | Open Reading Frame Dec. 15, 1999 release | Orientation | SEQ ID NO |
|---|---|---|---|---|---|
| 131 | 1110 | 4715256 | 4714774–4715991 | Forward | 1 |
| 102 | 5547 | 2067716 | 2066736–2068517 | Reverse | 2 |
| 101 | 7730 | 2065297 | 2064803–2065495 | Reverse | 3 |
| 117 | 41430 | 2031833 | 2031245–2031655 | Forward | 4 |
| 136 | 851491 | 1221771 | 1221374–1221961 | Reverse | 5 |
| 116 | 1138940 | 934322 | 934191–935210 | Reverse | 6 |
| 129 | 1141723 | 931539 | 930603–931772 | Reverse | 7 |
| 115 | 1941557 | 131753 | 131583–131792 | Reverse | 8 |
| 137 | 2007007 | 66507 | 66264–68135 | Forward | 9 |
| 130 | 2313744 | 6023975 | 6023787–6024542 | Forward | 10 |
| 138 | 2459178 | 5878418 | 5877776–5878597 | Forward | 11 |
| 106 | 2870317 | 5467402 | 5466520–5467887 | Forward | 12 |
| 132 | 3616599 | 4721118 | 4720249–4721457 | Forward | 13 |
| 133 | 3628342 | 4709375 | 4707483–4710572 | Forward | 14 |
| 113 | 3771157 | 4566558 | 4565369–4567903 | Reverse | 15 |
| 134 | 3781254 | 4556461 | 4555202–4558177 | Forward | 16 |
| 103 | 3961920 | 4375793 | 4375589–4376680 | Forward | 17 |
| 119 | 4446918 | 3890793 | 3890724–3892004 | Reverse | 18 |
| 118 | 4447967 | 3889744 | 3559088–3889738 | Reverse | 19 |
| 120 | 4592102 | 3745609 | 3744850–3746016 | Forward | 20 |
| 121 | 4594988 | 3742723 | 3742643–3743635 | Forward | 21 |
| 122 | 4595538 | 3742173 | 3740961–3742217 | Forward | 22 |
| 123 | 4597340 | 3740171 | 3740054–3740968 | Forward | 23 |
| 124 | 4598281 | 3739430 | 3738724–3740052 | Forward | 24 |
| 125 | 4600099 | 3737612 | 3737561–3738727 | Forward | 25 |
| 126 | 4603518 | 3734193 | 3730455–3737564 | Forward | 26 |
| 127 | 4608787 | 3728924 | | Reverse | |
| 135 | 4942182 | 3395532 | 3395274–3396677 | Reverse | 27 |
| 114 | 5209051 | 3128663 | 3127731–3129116 | Forward | 28 |
| 104 | 5402505 | 2935208 | 2934490–2935593 | Forward | 29 |
| 105 | 5410045 | 2927668 | 2926722–2927972 | Reverse | 30 |
| 108 | 5617382 | 2720329 | 2718890–2720643 | Reverse | 31 |
| 109 | 5651872 | 2678258 | 2671678–2679012 | Reverse | 32 |
| 110 | 5661697 | 2676014 | 2671678–2679012 | Reverse | 32 |
| 111 | 5666282 | 2671429 | 2669119–2671674 | Reverse | 33 |
| 112 | 5701004 | 2636707 | 2636467–2638800 | Reverse | 34 |
| 107 | 5799641 | 2538070 | 2532619–2539008 | Reverse | 35 |
| 100 | 5801998 | 2535711 | 2532619–2539008 | Reverse | 35 |
| 128 | 5924799 | 2412909 | 2412807–2414201 | Forward | 36 | qsc101 and 102 genes are an example of a putative operon that was not identified by functional coupling (FIG. 4). These two ORFs did not show significant similarities with other polypeptides. Nevertheless, they are transcribed in the same direction, closely juxtaposed, qsc101 and 102 are both Class I genes, and there is a las box-like element upstream of these ORFs. Expression of the qsc102 insertion is controlled by an upstream ORF (SEQ ID NO:37) which comprises the sequences between postions 2068711 to 267911 of the *P. aeruginosa* genome (Dec. 15, 1999 release) which in turn is preceded by a las box regulatory element (SEQ ID NO:38) which comprises the sequences between postions 2068965 to 2068946 of the *P. aeruginosa* genome (Dec. 15, 1999 release). The las box is a palindromic sequence found upstream of and involved in LasR-dependent activation of lasB (Rust, L. et at., (1996) *J. Bacteriol.* 178, 1134–1140).

The qsc133A and B insertions are in a putative 3-gene operon with similarity to acrAB-tolC from *E. coli* and the mex-opr family of efflux pump operons in *P. aeruginosa*, one of which (mexAB-oprN) has been shown to aid $3OC_{12}$-HSL efflux (Kohler, T., et al. (1997) *Mol. Microbiol.* 23, 345–354; Poole, K, et al. (1993) *J. Bacteriol.* 175, 7363–7372; Poole, K.et al. (1996) *Mol. Microbiol.* 21, 713–724; Evans, K., et al. (1998) *J. Bacteriol.* 180, 5443–5447; Pearson, J. P. et al. (1999) *J. Bacteriol.* 181, 1203–1 210). The qsc133 mutations are within a gene encoding a MexF homolog. The qsc133 mutants show typical Class IV regulation. Expression of lacZ is late and dependent on the presence of both acyl-HSL signals (Table 3 and FIG. 2). No las box-like sequences upstream of this suspected efflux pump operon were identified.

A third possible operon identified by functional coupling is about 8 kb and contains 10 genes. Eight strains with insertions in 6 of the 10 genes were obtained, all of which are Class III mutants (Table 3). A las box-like sequence was identified upstream of the first gene of this operon. The function of these 10 genes is unknown but the similarities shown in Table 2 suggest that they may encode functions for synthesis and resistance to an antibiotic-like compound.

The qsc128 mutation is within a gene coding for a polypeptide that shows similarity to the *P. fluorescens* hcnB product and appears to be in a 3-gene operon (Table 3, FIG. 4). By analogy to the *P. fluorescens* hcn operon, this operon is likely required for the production of the secondary metabolite, hydrogen cyanide. Previous investigations have shown that hydrogen cyanide production is reduced in *P. aeruginosa* rhl quorum sensing mutants. Consistent with this, qsc128 is a Class III mutant (Table 2). Full induction required both acyl-HSL signals, however, some induction of lacZ resulted from the addition of either signal alone (Table 3). A las box-like sequence was identified in the region upstream of the translational start codon of the first gene in this operon. This las-type box may facilitate an interaction with either LasR or RhlR.

Figure 5:
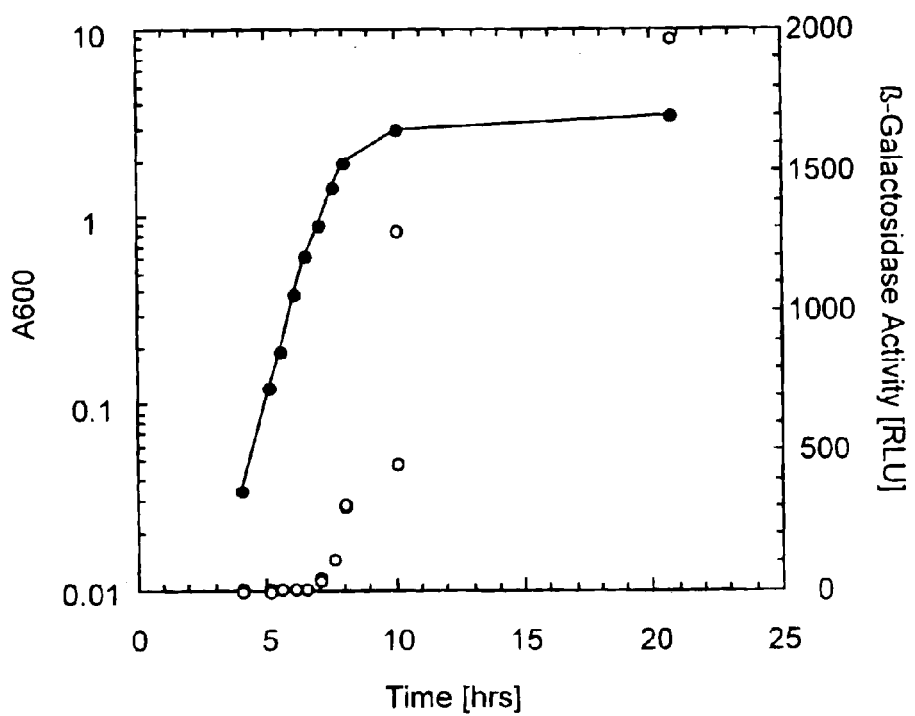
FIG. 5 depicts a growth curve of PAO1/pMW303G. Culture growth is monitored at 600 nm (closed circles) and β-galactosidase activity is measured with a chemiluminescent substrate analog in relative light units (RLU; open circles).

The phz operon, required for phenazine biosynthesis, has been described in other pseudomonads and the insertion in strain qsc131 is located in a gene encoding a phzC homolog. Analysis of the sequence around this phzC homolog revealed an entire phenazine biosynthesis operon, phzA-G (Georgakopoulos, D. G. et al. (1994). *Appl. Environ. Microbiol.* 60, 2931–2938; Mavrodi, D. V. et al. (1998) *J. Bacteriol.* 180, 2541–2548). As discussed above, qsc131 does not produce the blue phenazine pigment pyocyanin. PhzC is part of an operon of several genes including PhzBCDEFG, and transcription of this operon is controlled by the promoter region (SEQ ID NO:39) in front of the first gene in the operon, PhzA. The phz operon in *P. aeruginosa* also contains a las-box like sequence upstream of the first gene of the operon. The PhzA promoter region (SEQ ID NO:39) has been cloned into a plasmid, transcriptionally fused to lacZ. The resulting plasmid (pMW303G) was transformed into PAO1 and used as a reporter strain. The resultant bacterial strain generates a quorum sensing signal and responds to it by increased β-galactosidase activity. As shown in FIG. 5, this strain displayed a high level of induction between early and late growth, thus providing a dynamic range for detecting modulation (e.g., inhibition) of quorum sensing signaling. Accordingly this strain may be useful for a single strain assay for identifying for inhibitors of quorum sensing singaling, as d escribed herein.

The final putative operon consists of 2 or 3 genes, qsc109–111, which appear to be involved in pyoverdine synthesis. These ORFs were not identified in the *P. aeruginosa* genome project web site but were identified and shown to be functionally coupled with the Argonne National Laboratory web site.

For three of the qsc insertions, the lacZ gene was in an orientation opposite to the ORF described in the Genome Project web site (qsc114, 127, and 136).

Figure 6:
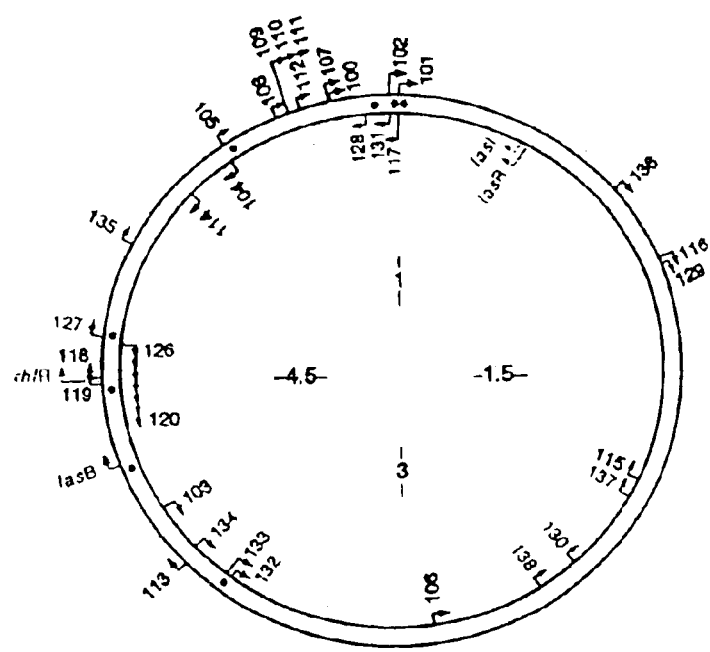
FIG. 6 is a map of the qsc insertions on the P. aeruginosa chromosome. Arrowheads indicate the direction of lacZ transcription. In addition to the qsc mutants, lasR and lasI, rhlR, and lasB are also mapped. The locations of las-boxes like elements are shown as black dots between the two DNA strands. The numbers indicate distance in megabases on the approximately 6 megabase chromosome.

Locations of qsc Genes on the *P. aeruginosa* Chromosome. The qsc genes were mapped to sites on the *P. aeruginosa* chromosome (FIG. 6). In addition lasB, lasR and lasI, and rhlR were placed on this map. The distribution of currently identified qsc genes is patchy. For example, 16 of the 39 qsc genes representing 3 of the classes mapped to a 600-kb region of the 6 megabase chromosome. A 140-kb island of 12 Class III genes, 8 transcribed in one direction and 4 transcribed in the other direction (including the rhl genes) formed another cluster on the chromosome.

Figure 7:
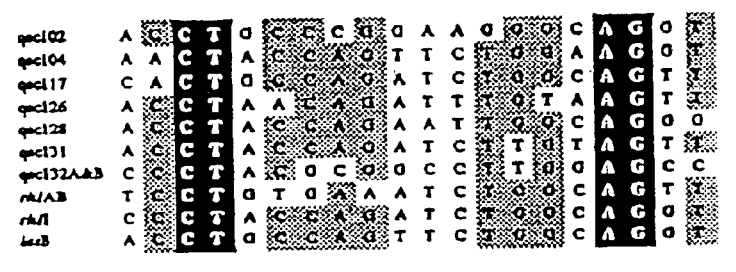

Identification of las Box-Like Sequences that Could be Involved in qsc Gene Control. As discussed above, the las box is a palindromic sequence found upstream of and involved in LasR-dependent activation of lasB (Rust, L. et al. (1996) *J. Bacteriol.* 178., 1134–1140). The las box shows similarity to the lux box, which is the promoter element required for quorum control of the *V. fischeri* luminescence genes (Devine, J. et al. (1989) *PNAS* 86, 5688–5692). Elements similar to a las box were identified by searching upstream of qsc ORFs. A search was done for sequences with at least 50% identity to the las box found 42 bp upstream of the lasB transcriptional start site (Rust, L. et al. (1996) *J. Bacteriol.* 178, 1134–1140). las box-like sequences were identified which are suspected to be involved in the regulation of 14 of the 39 qsc genes listed in Table 1 (FIG. 7). Because there is little information on the transcription starts of most of the genes identified in the screening assay, some relevant las boxes may have been missed and some of the identified sequences may not be in relevant positions.

Discussion

By screening a library of lacZ promoter probes introduced into *P. aeruginosa* PAO1 by transposon mutagenesis, 39 quorum sensing controlled (qsc) genes were identified. Most of these genes were not identified as quorum sensing-controlled previously. Mutations were not found in every gene in putative qsc operons (FIG. 4). Mutants that showed only a small degree of acyl-HSL-dependent lacZ induction in the initial screen were not studied. Thus, it is presumed that all of the quorum sensing controlled (qsc) genes have been identified. A conservative estimate is that about 1% of the genes in *P. aeruginosa* are controlled by quorum sensing (39 out of about 5,000–6,000 genes in the *P. aeruginosa* chromosome were confirmed to be qsc without saturating the mutagenesis). A more liberal estimation of 3–4% can be drawn from the finding of 270 mutants showing at least a 2-fold induction in response to one or both of the acyl-HSL signals in the initial screen of 7,000 mutants.

Several mutants, for example qsc101 and 102 showed an immediate and relatively large response to $3OC_{12}$-USL (Class I mutants, Table 3). The qsc101 and 102 genes code for proteins with no matches in the databases. Several mutants showed a relatively large and immediate response when both signals were supplied in the growth medium. Examples are qsc119 (rhlB), 121–125, and 129A and B. The qsc mutant showing the largest response was qsc131. lThe level of β-galactosidase activity when this mutant was grown in the presence of both signals was greater than 700 times that in the absence of the signals (Table 3). The qsc131 mutation is in phzC, which is a phenazine biosynthesis gene, and the qsc131 mutant did not produce the blue phenazine pigment pyocyanin at detectable levels. Many of the mutants that responded best to both signals early (Class III mutants) showed a small response when exposed to one or the other signal. The reasons for the small response to either signal are unclear at present but the data suggest that these genes may be subject to signal cross talk, or they may show a response to either LasR or RhlR. One reason they may respond to both signals better than they respond to $C_4$-HSL alone is that $3OC_{12}$-HSL and LasR are required to activate RhlR, the transcription factor required for a response to $C_4$-HSL (Latifi, A. et al. (1996) *Mol. Microbiol.* 21, 1137–1146; Pesci, E. C. et al. (1997) *J. Bacteriol.* 179, 3127–3132). There were two mutant classes that showed a delayed response to the signals; Class II mutants which required only $3OC_{12}$-HSL, and Class IV mutants, which required both signals for full induction. These mutants showed between 5 and 45-fold activation of gene expression (Table 3). There are a number of possible explanations for a delayed response to signal addition. It is possible that some of these genes are stationary phase genes. It is also possible that some are iron repressed. For example, it is known that the synthesis of pyoverdine is regulated by iron and the Class II, delayed response, qsc108–111 mutations are in genes involved in pyoverdine synthesis (Cunliffe, H. E. el al. (1995) *J. Bacteriol.* 177, 2744–2750; Rombel, I. et al. (1995) *Mol. Gen. Genet.* 246, 519–528). It is also possible that some of these genes are not regulated by quorum sensing, directly. The acyl-HSL signals might control other factors that influence expression of any of the genes that have been identified and this possibility seems most likely with the late genes in Classes II and IV. Indirect regulation may not be common for late genes. This is known because the lasB-lacZ chromosomal insertion which was generated by site-specific mutation was in Class IV, and it is known from other investigations that lasB responds to LasR and $3OC_{12}$-HSL, directly (Passador, L. et al. (1993) *Science* 260, 1127–1130;

Rust, L. et al. (1996) *J. Bacteriol.* 178, 1134–1140). The two classes of late qsc genes may be comprised of several subclasses.

Las boxes are genetic elements which may be involved in the regulation of qsc genes. Although sequences with characteristics similar to las boxes were identified, (FIG. 7), the locations of these sequences have not provided insights about the differences in the patterns of gene expression among the four classes of genes. It is possible that when the promoter regions of, the qsc genes are studied that particular motifs in the regulatory DNA of different classes of genes will be revealed.

Many of the qsc genes appear to be organized in two patches or islands on the *P. aeruginosa* chromosome (FIG. 7). Because LasR mutants are defective in virulence it is tempting to speculate that these gene clusters may represent pathogenicity islands. The rhlI–rhlR quorum sensing modulation occurs on one of the qsc islands, but none of the qsc genes are tightly linked to the lasR–lasI modulon. Genes representing each of the 4 classes occur over the length of the chromosome and on both DNA strands. This is consistent with the view that quorum sensing is a global regulatory system in *P. aeruginosa*. Of interest there is a third LuxR family member in *P. aeruginosa*. This gene is adjacent to and divergently oriented from qsc103.

Quorum sensing is critical for virulence of *P. aeruginosa* and for the development of mature biofilms. The methodology disclosed herein for identification of qsc genes provides a manageable group of genes to test for function in virulence and biofilm development. Furthermnore, the availability of the *P. aeruginosa* genome sequence will very likely lead to the development of a gene expression microarray for this organism. The methods described herein provide a set of 39 genes that respond to specific treatments in a predictable fashion (Table 3).

EXAMPLE 2

Screening Assay for Quorum Sensing Inhibiting Compounds

Figure 8:
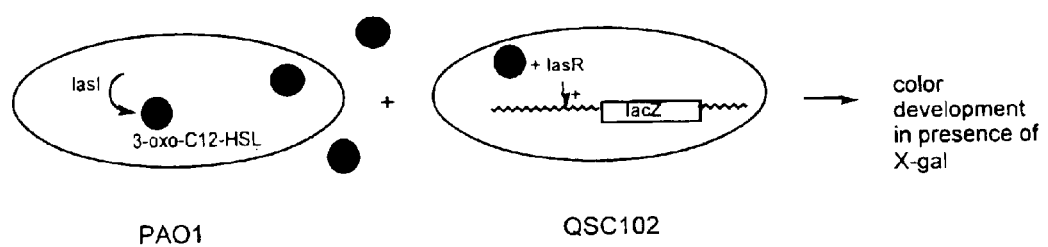
FIG. 8 depicts the principle of a bioassay for modulators of quorum sensing signaling. Strain PAO1 produces the signal 3-oxo-C12-HSL. Strain QSC102 responds by inducing lacZ.

In this example, the screening assay used two strains of *P. aeruginosa*: a wild type *P. aeruginosa* (PAO1) and QSC102, from Example 1 (see FIG. 8). This assay will detect inhibition of all aspects of quorum sensing signaling, e.g., signal generation and signal reception.

Procedural Overview

Microtiter plates are prepared by adding 200 µL Luria Broth ("LB") agar, containing 0.008% 5-bromo-4-chloro-3-indolyl-β-D-galactose (X-gal) to each well. Overnight cultures of PAO1 and QSC102 are subcultured in LB to a starting absorbance at 600 nm ("A600") of 0.05 and grown at 37° C to an A600 of 1.0. PAO1 is diluted $2.5 \times 10^5$-fold in LB and 5 µL of this is applied to the surface of the LB agar in each well. Plates are then dried in a laminar flow hood for 60 minutes. A tenfold dilution of QSC102 in LB is used to inoculate each well using a replicator. Plates are then sealed and incubated at 37° C for 40 hours. Growth and color development are evaluated visually and the data is recorded with a camera.

The test compound was present in a microtiter well and overlaid with LB agar and 5-bromo-4-chloro-3-indolyl-β-D-galactose (X-gal). Both strains were spotted on the agar in each well. PAO1 emitted the acyl-HSL signal (3-oxo-C12-HSL), to which QSC102 responded by turning blue. QSC102 expressed β-galactosidase only in response to the LasI signal (3-oxo-C12-HSL); the lacZ fusion in QSC102 did not respond to the RhlI signal (C4-HSL). Hence, the assay was selective for inhibitors of the Las system. Inhibition of signaling was evaluated qualitatively by the absence or weakening of the blue color development.

Figure 9:
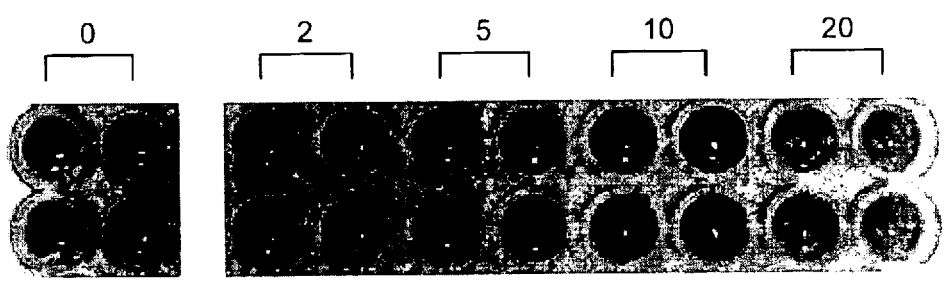
FIG. 9 depicts the results of an assay performed using the test compound acetyl-butyrolactone, which is present in the wells at increasing concentration (mM, as indicated). There are two rows and two columns per concentration to show reproducibily of the assay.

The assay was used to test 6 product analogs, two of which showed an inhibitory effect: butyrolactone and acetyl-butyrolactone. Although bacterial growth was not inhibited, the color development was reduced. Color reduction correlated directly with test compound concentration, although relatively high concentrations (~20 mM) were required to suppress color development completely (FIG. 9).

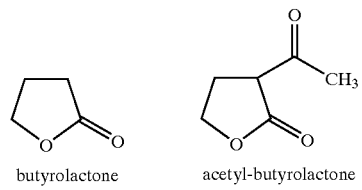

butyrolactone     acetyl-butyrolactone

EXAMPLE 3

Development of a *P. Aeruginosa* Strain for a High Throughput Screening Assay

Figure 10A:
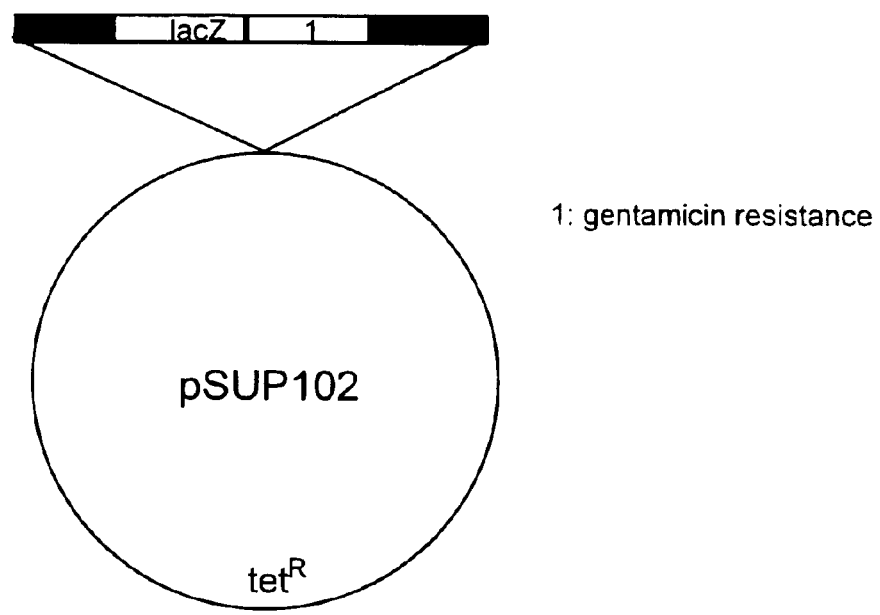
FIG. 10A depicts the structure of a mobilizable plasmid for generating an indicator strain. Filled boxes represent chromosomal DNA derived from the *P. aeruginosa* locus where lacZ is inserted in strain QSC102.

A. Construction of Reporter Strain-Chromosomal Insertion of Reporter A strain for use in high-throughput screening was constructed by inserting the lacZ transcriptional fusion, linked gentamicin resistance marker, and about 2 kb of flanking DNA from strain QSC102 into a mobilizable plasmid (such as pSUP102) as depicted in FIG. 10A. Plasmid pSUP102 confers tetracycline resistance and does not replicate in *P. aeruginosa* (Simon, R. et al. (1986) *Meth. Enzym.* 118:640–659). The pSUP102-derivative was then transferred into PAO1 by bi- or triparental mating, selecting for gentamicin resistance (Suh, S. J. et al. (1999) *J Bacteriol.* 181(13):3890–7). Gentamicin resistant isolates were screened for tetracycline sensitivity (i.e., a double cross-over event has resulted in a chromosomal insertion). Southern blotting was used to confirm the nature of the recombination event and to rule out candidates with more than one insertion. The resultant bacterial strain generates the signal (3-oxo-C12-HSL) and responds to it by increased β-galactosidase activity. A similar strategy is used to create a reporter strain that expresses gfp instead of lacZ. The initial GFP variant is the stable and bright variant GFPmut2 (Cormack, B. P. et al. (1996) *Gene.* 173(1):33–38).

Procedural Overview of Assay

A culture of PAQ1 reporter strain (carrying the reporter gene lacZ transcriptionally fused to the regulatory sequence of qsc102 in the wildtype background, PAO1) was grown in LB, 100 µg/ml gentarnicin overnight, such that the A600 was around 0.1. The culture was washed in LB twice and used to subculture at a 1:1000 dilution in LB. The subculture was grown in the presence or absence of test compound. Growth was monitored at A600 and expression of β-galactosidase activity is measured according to the Miller assay (Miller, J. A. (1976) in *Experiments in Molecular Genetics* pp 352–355, Cold Spring Harbor Lab. Press, Plainview, N.Y.).

The reporter strain was tested by growing it in microtiter plates in the presence and absence of known inhibitors of bacterial signaling. Examples of known inhibitors are: acetyl-butyrolactone, butyrolactone, and methylthioadenosine, a product of the synthase reaction that was shown to be inhibitory to the RhlI synthase (Parsek, M.

Figure 10B:
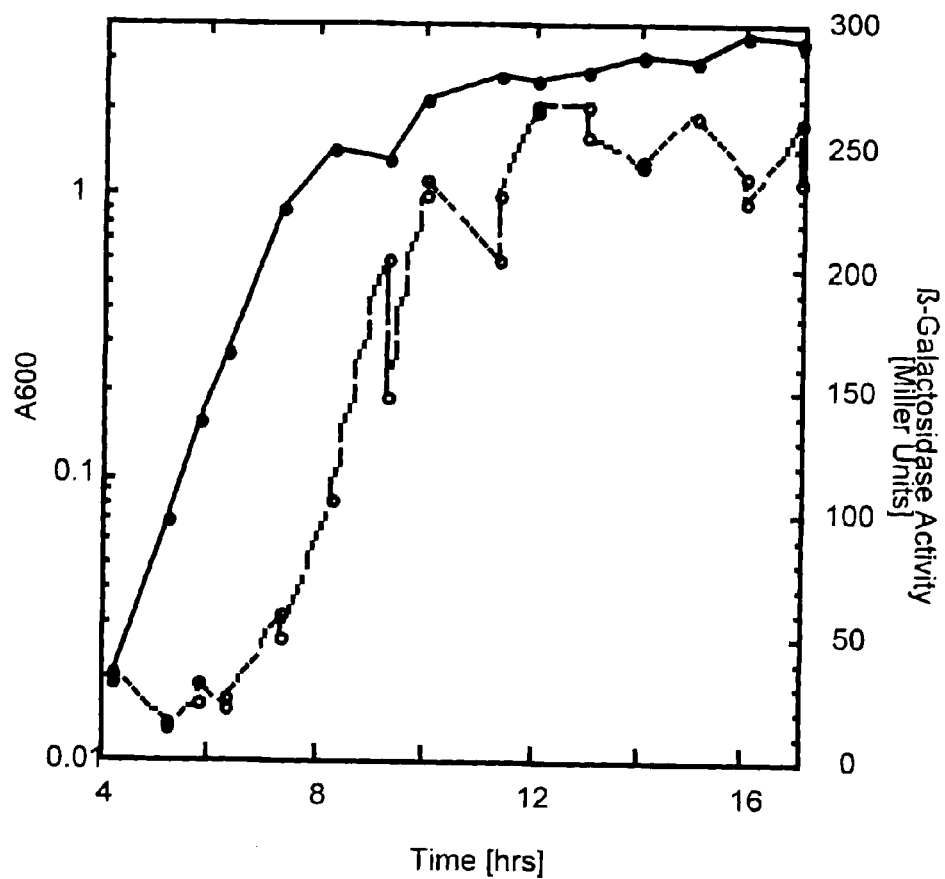
FIG. 10B depicts induction of β-galactosidase as PAQ1 reaches high density. Cell growth is monitored at 600 nm (closed circles) and expression of 13-galactosidase is measured in Miller units (open circles).

R. et al. (1999) *Proc. Natl. Acad. Sci. USA*. 96:43604365). Initial characterization of the assay entailed following the optical density (cell growth) in individual sample wells and measuring induction levels at different time points. FIG. 10B shows the induction of β-galactosidase as PAQ1 reaches high density, wherein cell growth is measured at 600 nm (closed circles) and expression of β-galactosidase is measured in Miller units (open circles). For GFP fusions, the fluorescence of the culture is determined after excitation at 488 nm.

B. Construction of Reporter Strain-Reporter on a Plasmid

The PAO1/pMW303G strain is constructed as described in Example 1 above.

Procedural Overview of the Assay

An overnight culture of PAO1/pMW303G was diluted to an A600 of 0.1 in LB, 300 µg/ml carbenicillin. Of this, 50 µL were added to microtiter plate wells and grown at 37° C, shaking at 250 rpm, in the presence or absence of test compounds. Culture growth was monitored directly in the microtiter plate at 620 nm. Expression of the reporter gene, β-galactosidase was measured with the Galacton substrate by Tropix as follows. 12A 20 µL aliquot of the culture was added to 70 µL of 1:100 diluted Galacton substrate (Tropix, PE Biosystems, Bedford, Mass.) and incubated in the dark at room temperature for 60 minutes. The reaction was stopped and light emission was triggered by the addition of 100 µL Accelerator II (Tropix, PE Biosystems, Bedford, Mass.), and luminescence was read with plate reader (SpectrofluorPlus, Tecan). Timepoints were taken at 5, 8 and 12 minutes.

In either embodiment of the assay (chromosomal insertion of reporter, or reporter on a plasmid), a satisfactory assay shows normal cell growth but reduced β-galactosidase activity or gfp expression in the presence of a known signaling inhibitor. Possible problems associated with the use of fluorescence in whole-cell systems are interference by turbidity as cell density increases and the production of pyocyanin and pyoverdine, fluorescent molecules that are excreted by wild type *P. aeruginosa*. However, interference due to endogenous fluorescent pigments may be reduced by using mutants that lack these pigments (Byng, G. S. et al. (1979) *J Bacteriol.* 138(3):846–52).

EXAMPLE 4

Screening Assay to Determine Inhibition of the Signal Synthase

An assay was developed to measure inhibition of RhlI activity, based on a previously published enzyme assay for RhlI (Parsek, M. R. et al. (1999) *Proc. Natl. Acad. Sci. USA*. 96:43604365). It was shown that the substrates for RhlI are S-adenosylmethionine (SAM) and butanoyl-acyl carrier protein (C4-ACP). It is proposed that RhlI can be used as a model enzyme to study inhibition of acyl-HSL synthases. This is based on the observation that TraI from *Agrobacterium tumefaciens* (Moré, M. I. et al. (1996) *Science*. 272 (5268): 1655–8) and LuxI from *Vibrio fischeri* (Schaefer, A. L. et al. (1996) *Proc Natl Acad Sci USA*. 93(18):9505–9), two homologs of RhlI and LasI, that also utilize SAM and the respective acylated-acyl carrier protein as their substrates.

Figure 11:
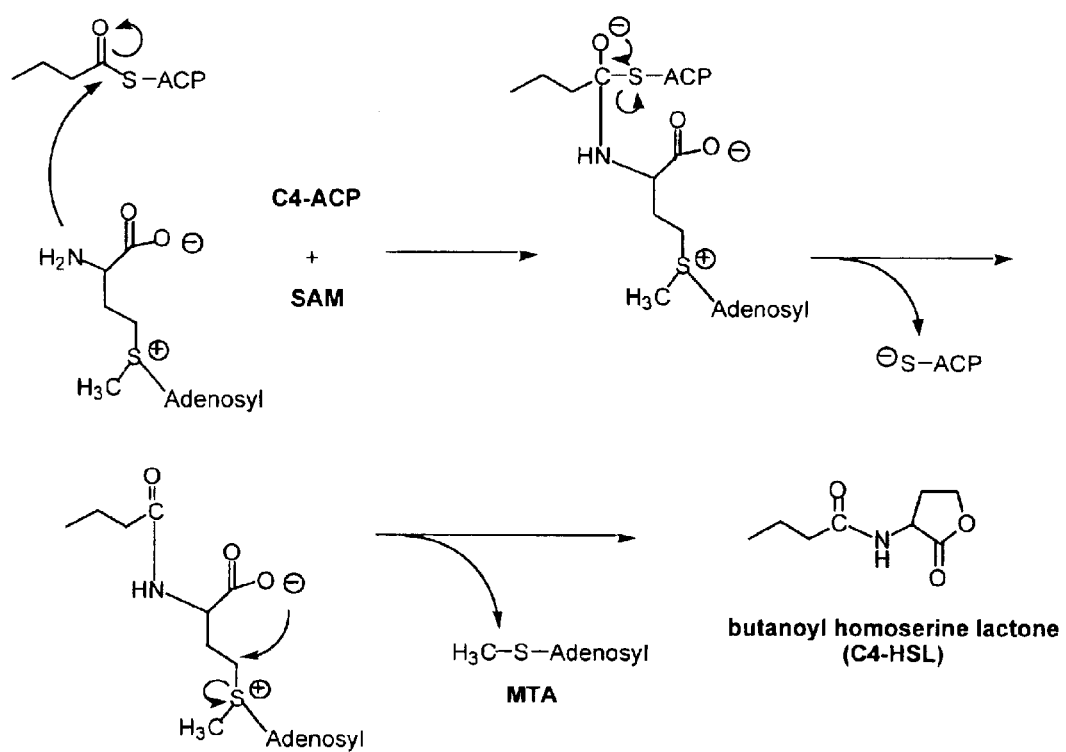
FIG. 11 depicts the reaction mechanism of the RhlI autoinducer synthase.

RhlI activity assay. Studies of autoinducer synthases have been hampered by the low solubility of the enzyme. It is only in the past year that the first rigorous characterization of an autoinducer synthase was published (Parsek, M. R. et al. (1999) *Proc. Natl. Acad Sci. USA*. 96:4360–4365). This study was performed on RhlI, which had been slightly overproduced in a LasI minus strain of *P. aeruginosa*, thereby avoiding previously encountered problems of solubility. The reaction mechanism deduced for RhlI is summarized in FIG. 11. The substrates for the synthase are butanoyl-acyl carrier protein (C4-ACP) and S-adenosylmethionine (SAM). The amino-group of SAM attacks the thioester of C4-ACP to form a peptide bond between butanoic acid and SAM. The first product, acyl carrier protein (ACP) is released. Next, the SAM-moiety undergoes internal ring closure to form a homoserine lactone (HSL). Methylthioadenosine (MTA) and butanoyl-HSL (C4-HSL) are released.

The enzyme assay reaction mixture contains 60 µM $^4$C-labeled SAM and 40 µM C4-ACP in a final volume of 100 µL (buffer: 2 mM dithiothreitol, 200 mM NaCl, 20 mM Tris-HCL, pH 7.8). The reaction is started with the addition of 70 ng RhlI, incubated at 37° C and quenched after 10 min by addition of 4 µL of 1 M HCl. Product formation is quantitated by extracting the reaction mixtures with 100 µL ethyl acetate and scintillation counting the radiolabeled C4-HSL, which partitions into the organic phase. (SAM remains in the aqueous phase.)

Other variations on the assay include detection of the non-acylated ACP (i.e., ACP with a free thiol group). Non-acylated ACP can be detected through the use of a thiol reagent such as dithionitrobenzoic acid (DTNB), which releases a highly colored thiolate ($\epsilon_{412}$=13 600 cm$^{-1}$ M$^{-1}$) upon reaction with thiol groups (Ellman, G. L. (1959) *Arch. Biochem. Biophys*. 82:70–77). Another variation of this assay uses an even more sensitive reagent, 4,4'-dithiobipyridyl which has a $\epsilon_{324}$=20 000 cm$^{-1}$ M$^{-1}$ (Jamin, M. et al. (1991) *Biochem J.* 280(Pt 2):499–506). Use of DTNB eliminates the need for radioactivity and allows for a continuous assay.

Another variation on the assay includes using a substitute for the substrate C4-ACP. It has already been found that RhlI turns over butanoyl-CoA in lieu of C4-ACP (Parsek, M. R. et al. (1999) *Proc. Natl. Acad. Sci. USA*. 96:4360–4365). The $K_M$ for the CoA substrate is 230 µM, compared to 6 µM for C4-ACP, but $v_{max}$ is only one order of magnitude slower. N-Acetylcysteamine represents a truncated moiety of CoA and acylated N-acetylcysteanines often function as substrate analogs for CoA-dependent enzymes (Bayer et al. (1995) *Arch Microbiol.* 163(4):310–2; Singh, N. et al. (1985) *Biochem Biophys Res Commun.* 131(2):786–92; Whitty, A. (1995) *Biochemistry*. 34(37): 11678–89). It will be determined whether butanoyl-N-acetylcysteamine is turned over by RhlI. If so, an assay will be developed for the release of free thiol groups with a thiol reagent such as DTNB. Butanoyl-N-acetylcysteamine is readily synthesized from the commercially available precursors butyrylchloride and N-acetylcysteamine.

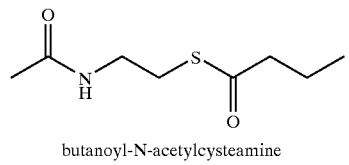

butanoyl-N-acetylcysteamine

LasI activity assay. In analogy with RhlI, TraI, and LuxI, proposed substrates for LasI are SAM and 3-oxo-C12-ACP. In this assay, compounds are tested for inhibiting the activity of LasI. This assay is based on observations that bacterial strains incubated with $^{14}$C-labeled methionine produce radiolabeled acylated-HSLs, which can be isolated from the culture supernatant and identified by their retention times (in comparison to known standards) when eluted over a high pressure liquid chromatography (HPLC) reversed phase column. A synthase-inhibitor assay has been set up using this methodology.

A *Pseudomonas* strain that expresses lasJ but not rhlI, such as PDO100, is grown in the presence and absence of the test compound (Brint, J. M. et al. (1995) *J Bacteriol.* 177(24):7155–63). Cells are pulsed for 10–30 minutes with $^{14}$C-labeled methionine (available from American Radiochemicals) and pelleted by centrifugation. The supernatant liquid is extracted with ethyl acetate and the products separated by HPLC. If the test compound inhibits LasI synthase, the amount of 3-oxo-C12-HSL produced will be significantly reduced when compared to the control.

An in vitro assay for LasI activity similar to the radiometric assay used to study RhlI will be developed. The substrates for this assay are $^{14}$C-labeled SAM (available Amersham Pharmacia) and 3-oxo-C12-ACP (similar methodology in Moré, M. I. et al. (1996) *Science.* 272(5268):1655–8). LasI activity is monitored by the appearance of radiolabeled 3-oxo-C12-HSL, after extraction into ethyl acetate and scintillation counting. Initially, crude extracts of LasI overexpressed in *E. coli* serve as the source of enzyme. Once a satisfactory assay is in place, a purification protocol will be developed to obtain LasI in a soluble and active form. The purification may involve expression at low levels (low plasmid copy number, weak promoter, low growth temperature) in a *P. aeruginosa* rhlI mutant. Purification will follow standard techniques such as ammonium sulfate precipitation, anion exchange chromatography, cation exchange chromatography and size-exclusion chromatography.

EXAMPLE 5

In Vivi Assays to Determine Inhibition of Signal Binding

In vivo assays were also used to determine whether a test compound inhibits signal reception by LasR.

One assay used the *P. aeruginosa* strain QSC102 (Table 3), which responds to the presence of exogenous 3-oxo-C12-HSL by inducing β-galactosidase activity up to 400-fold (Example 1). Cells were grown in the presence of a minimal concentration of 3-oxo-C12-HSL and in the presence and absence of the test compound. If the test compound interferes with signal reception, β-galactosidase activity is reduced. Interference can be a result of any of several mechanisms. The simplest is, if the test compound prevents the 3oxo-C12-HSL from binding to LasR. Alternatively, the test compound may prevent LasR from binding to DNA or interacting productively with RNA polymerase.

A further in vivo assay is used to determine whether a test compound inhibits binding of 3-oxo-C12-HSL to LasR. This assay is based on an observation originally made with LuxR of *Vibrio fischeri*. Namely, the autoinducer binds to *Escherichia coli* cells in which LuxR is produced, provided that LuxR is co-expressed with Hsp60 (Adar et al. (1993) *J Biolumin Chemilumin.* 8(5):261–6). This finding was used to develop a competition-assay for binding of inhibitors to LuxR (Schaefer, A. L. et al. (1996) *J Bacteriol.* 178(10):2897–901) and LasR (Passador, L. et al. (1996) *J Bacteriol.* 178(20):5995–6000). Briefly, cultures of *E. coli* harboring expression plasmids for Hsp60 and LasR (or LuxR) are induced for several hours, at which time an aliquot of cells is added to tritiated signal molecule, alone or in combination with a potential inhibitor. After 10–15 minutes, cells are pelleted by centrifuigation, washed, and the amount of radioactivity bound to the cells is determined by scintillation counting.

Plasmids for expression of LasR (pKDT37) (Passador, L. et al. (1996) *J Bacteriol.* 178(20):5995–6000) and Hsp60 (pGroESL) have been made. A simple method for preparing $^{14}$C-labeled 3-oxo-C12-HSL has been developed. *E. coli* cells expressing lasI excrete $^{14}$C-labeled 3-oxo-C12-HSL into the medium when incubated in the presence of $^{14}$C-labeled methionine. The $^{14}$C-labeled 3-oxo-C12-HSL can be recovered by extraction into ethyl acetate and purified by HPLC. The correct product is identified by its radioactivity and by the correct HPLC retention time compared to an unlabeled standard.

EXAMPLE 6

Assay for Inhibition of Biofilms

This assay tests whether compounds useful for inhibiting quorum sensing also inhibit or modulate the formation or growth of biofilms. The LasI/LasR signaling system was found to regulate not only the expression of virulence factors, but also the development of mature biofilms (Davies, D. G. et al. (1998) *Science.* 280(5361):295–8). This was demonstrated by using a simple flow-through system, as shown in FIG. 12, that allows fresh medium to be pumped through a small chamber in a Plexiglas body.

Cultures of *P. aeruginosa* expressing green fluorescent protein (GFP) were grown in a chamber that was sealed with a coverslip and flushed with fresh medium. Surface attachment and biofilm maturation were determined by examining the coverslip by epifluorescence and confocal microscopy. Both wild type PAO1 and a rhlI mutant strain were able to attach to the surface and form the mushroom-shaped structure characteristic of a biofilm. However, a lasI mutant that cannot synthesize the signal molecule 3-oxo-C12-HSL was only able to attach to the surface. It did not encase itself in an extracellular matrix or form any kind of three-dimensional structure. It also remained susceptible to 0.2% sodium dodecyl sulfate, which was used to mimic the susceptibility to a biocide. When the 3-oxo-C12-HSL signal was added back to the lasI mutant cells, the wild type phenotype was restored. The cells formed biofilms and remained resistant to sodium dodecyl sulfate.

Figure 12:
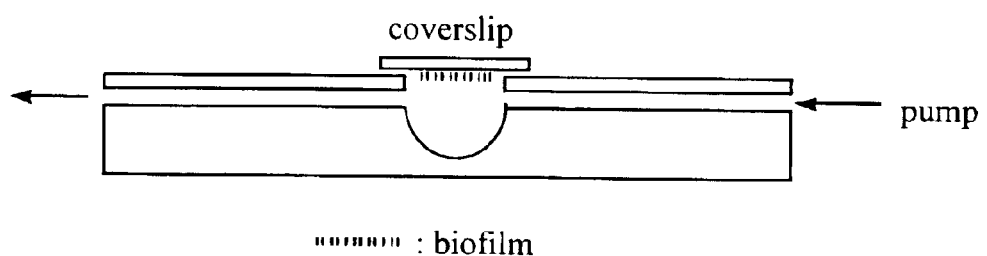
FIG. 12 depicts a continuous culture bioreactor.

Accordingly, the bioreactor depicted in FIG. 12 is inoculated with wild type *P. aeruginosa* PAO1 that expresses GFP. Test compounds (signaling inhibitors) are added to the flow-through medium to determine whether they prevent formation of the three-dimensional structures typical of a bacterial biofilm. Biofilm formation is monitored using a confocal microscope.

References

1. Holloway, B. W., Krishnapillai, V. & Morgan, A. F. (1979) *Microbiol. Rev.* 43, 73–102.
2. Brint, J. M. & Ohman, D. E. (1995) *J. Bacteriol.* 177, 7155–7163.
3. Sambrook, J., Fritsch, E. F. & Maniatis, T. (1989) *Molecular cloning: a laboratory manual* (Cold Spring Harbor Laboratory Press, Cold Spring Harbor, N.Y.).
4. Miller, V. L. & Mekalonos, J. J. (1988) *J. Bacteriol.* 170, 2575–2583.
5. Simon, R., Priefer, U. & Puhler, A. (1983) *Bio-Technology* 1, 37–45.

6. Pearson, J. P., Pesci, E. C. & Iglewski, B. H. (1997) *J. Bacteriol.* 179, 5756–5767.
7. Linn, T. & St Pierre, R. (1 990) *J. Bacteriol.* 172, 1077–1084.
8. Schweizer, H. P. (1 993) *Biotechniques* 15, 831–833.
9. Figurski, D. H. & Helinski, D. R. (1979) *Proc. Natl. Acad Sci. USA* 76, 1648–1652.
10. Simon, R., O'Connell, M., Labes, M. & Puhler, A. (1986) in *Methods in Enzymology, Vol.* 118, pp. 640–659.

Incorporation by Reference

The contents of all references, patents and published patent applications cited throughout this application, as well as the figures and the sequence listing, are incorporated herein by reference.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for identifying a modulator of quorum sensing signaling in bacteria, said method comprising:
providing a cell which is capable of endogenously synthesizing a quorum sensing signal molecule, wherein said cell comprises a regulatory sequence of a quorum sensing controlled gene operatively linked to a gene that generates a detectable signal in response to the quorum sensing signal molecule;
contacting said cell with a test compound, wherein said test compound is other than said quorum sensing signal molecule;
and comparing said detectable signal generated in the presence of said test compound with said detectable signal generated in the absence of said test compound, to thereby identify said test compound as said modulator of quorum sensing signaling in bacteria.

2. A method for identifying a modulator of quorum sensing signaling in bacteria, said method comprising:
providing a cell which comprises a quorum sensing controlled gene wherein said quorum sensing controlled gene comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36, operatively linked to a gene that generates a detectable signal in response to a quorum sensing signal molecule;
contacting said cell with said quorum sensing signal molecule in the presence and absence of a test compound;
and comparing said detectable signal generated in the presence of said test compound with said detectable signal generated in the absence of said test compound, to thereby identify said test compound as said modulator of quorum sensing signaling in bacteria.

3. A method for identifying a modulator of quorum sensing signaling in bacteria, said method comprising:
providing a cell which comprises a regulatory sequence of a quorum sensing controlled gene operatively linked to a gene that generates a detectable signal in response to a quorum sensing signal molecule;
contacting said cell with 3-oxo-C12 homoserine lactone in the presence and absence of a test compound;
and comparing said detectable signal generated in the presence of said test compound with said detectable signal generated in the absence of said test compound, to thereby identify said test compound as said modulator of quorum sensing signaling in bacteria.

4. A method for identifing a modulator of quorum sensing signaling in bacteria, said method comprising:
providing a cell which comprises a regulatory sequence of a quorum sensing controlled gene operatively linked to a gene that generates a detectable signal in response to a quorum sensing signal molecule;
contacting said cell with said quorum sensing signal molecule in the presence and absence of a test compound;
and detecting a change in said detectable signal to thereby identify said test compound as a modulator of quorum sensing signaling in bacteria.

5. The method of any one of claim 1, 2, 3, or 4, wherein said gene that generates said detectable signal comprises a reporter gene that is heterologous to said regulatory sequence.

6. The method of claim 5, wherein said detectable signal is provided by the transcription of said reporter gene or the translation product of said reporter gene.

7. The method of claim 6, wherein said reporter gene is selected from the group consisting of ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ, LEU1, LEU2, LEU4, luciferase, LYS2, MAL, MEL, MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA 10.

8. The method of claim 7, wherein said reporter gene is lacZ or GFP.

9. The method of any one of claim 2, 3, or 4, wherein said cell does not express said quorum sensing signal molecule.

10. The method of claim 9, wherein said quorum sensing signal molecule is produced by a second cell.

11. The method of claim 10, wherein said second cell is a prokaryote or eukaryote.

12. The method of claim 11, wherein said second cell is a bacterium.

13. The method of claim 12, wherein said second cell is wild type *Pseudomonas aeruginosa*.

14. The method of claim 12, wherein said bacterium is a gram negative bacterium.

15. The method of any one of claim 1, 2, 3, or 4, wherein said cell is a prokaryote or eukaryote.

16. The method of claim 15, wherein said cell is a bacterium.

17. The method of claim 16, wherein said bacterium is a gram negative bacterium.

18. The method of claim 17, wherein said gram negative bacterium is *Pseudomonas aeruginosa*.

19. The method of claim 16, wherein said bacterium is a mutant strain of *Pseudomonas aeruginosa* which comprises a regulatory sequence of a quorum sensing controlled gene operatively linked to a reporter gene, wherein in said mutant strain, lasI and rhlI are inactivated.

20. The method of claim 16, wherein said quorum sensing controlled gene encodes a virulence factor.

21. The method of claim 16, wherein said quorum sensing controlled gene encodes a polypeptide which inhibits a bacterial host defense mechanism.

22. The method of claim 16, wherein said quorum sensing controlled gene encodes a polypeptide which regulates biofilm formation.

23. The method of any one of claim 1, 2, 3, or 4, wherein said quorum sensing controlled gene is endogenous to said cell.

24. The method of any one of claim 1, 2, or 4, wherein said quorum sensing signal molecule is an autoinducer of said quorum sensing controlled gene.

25. The method of claim 24, wherein said autoinducer is a homoserine lactone.

26. method of claim 25, wherein said test compound is a homoserine lactone analog.

27. The method of any one of claim 1, 2, 3, or 4, wherein said modulator modulates the synthesis of said quorum sensing signal molecule by said bacterium.

28. The method of claim 27, wherein said synthesis is is inhibited.

29. The method of claim 27, wherein said synthesis is induced.

30. The method of any one of claim 1, 2, 3, or 4, wherein said modulator modulates reception of said quorum sensing signal molecule by said bacterium.

31. The method of claim 30, wherein said reception is inhibited.

32. The method of claim 30, wherein said reception is induced.

33. The method of any one of claim 1, 2, 3, or 4, wherein said modulator scavenges said quorum sensing signal molecule.

* * * * *

SEQUENCE LISTING

<160> NUMBER OF SEQ ID NOS: 39

<210> SEQ ID NO 1
<211> LENGTH: 1218
<212> TYPE: DNA
<213> ORGANISM: Pseudomonas aeruginosa

<400> SEQUENCE: 1

```
atggacgatc tattgcaacg cgtacggcgc tgcgaagcgc tgcagcaacc cgaatggggc      60
gatccgtcgc gcctgcgcga cgtgcaggcg tacctgcgcg gcagtccggc gctgatccgc     120
gccggcgaca tcctggccct gcgcgcgacc ctggcgcggg tcgcccgcgg cgaggcgctg     180
gtggtacagt gcggcgactg cgccgaggac atggacgacc accatgccga gaacgtggcg     240
cgcaaggccg ccgtgctgga actgctggcc ggcgccctgc gcctggccgg ccggcggccg     300
gtgatccgcg tcgggcgcat cgccgggcag tacgccaagc cgcgttccaa gccgcacgag     360
caggtcggcg agcagaccct gccggtctat cgcggcgaca tggtcaacgg ccgcgaggcc     420
catgccgaac agcgccgggc cgatccgcag cggatcctca agggctatgc ggcggcgcgc     480
aacatcatgc gccacctggg ctgggacgcc gcgtccgggc aggaggcgaa tgcctcgccg     540
gtctggacca gccacgagat gctgctgctc gactacgagc tgtcgatgct gcgcgaggac     600
gagcagcgcc gggtctatct cggttcgacc cactggccgt ggatcggcga gcgcacccgc     660
caggtcgacg gcgcccatgt ggcgctgctg gccgaggtgc tcaacccggt ggcctgcaag     720
gtcggtccgg agatcggccg cgaccagttg ctggcgctct gcgagcgcct cgatccgcgc     780
cgcgagccgg gacgcctgac gctgatcgcg cggatgggcg cgcagaaggt cggcgagcgc     840
ctgccgccgc tggtggaggc ggtgcgcgcg gccgggcacc cggtgatctg gctgagcgac     900
ccgatgcacg gcaacaccat cgtcgcgccc tgcggcaaca agacccgcct ggtgcgcagc     960
atcgccgagg aggtggcggc gttccgcctg ggatcctcta gccgaggcgg cgtgctcaac    1020
ggactgcacc tggaaaccac cccggacgac gtcaccgagt gcgtcgccga ttccagcggc    1080
ctgcaccagg tcagccggca ctacaccagc ctctgcgatc cgcggctgaa cccctggcag    1140
gcgctcagcg cggtgatggc ctggtccggc gcagaagcga tccagagcgc aaccttcccc    1200
ctggagaccg tggcatga                                                  1218
```

<210> SEQ ID NO 2
<211> LENGTH: 1782
<212> TYPE: DNA
<213> ORGANISM: Pseudomonas aeruginosa

<400> SEQUENCE: 2

```
atggatgatg gggcacagcc tgctgcacac ctcggatgcc ctgccaccac tgctggccgg      60
cttcgccgcc tacttcgtca acaccttcgt cacctactgg tggcatcgcg cgcgccacgc     120
```

-continued

```
caacgacacg ctctggcggc tgttccacca gttgcaccac gcgccgcaac gcatcgaggt    180
attcacctcc ttctacaagc atccgaccga gatggtcttc aactcgctgc tgggcagctt    240
cgtcgcctac gtggtgatgg gcatcagcat cgaggccggc gcctactaca tcatgttcgc    300
cgcgctcggc gagatgttct accactcgaa cctgcgcacc ccgcacgtcc tcggctacct    360
gttccagcgc ccggagatgc accgcatcca ccaccagcgc gaccgtcacg agtgcaacta    420
cagcgacttc ccgatctggg acatgttgtt cggcacctac gagaaccccc gccgcatcga    480
cgagccgcag ggcttcgccg cgacaagga gcagcagttc gtcgacatgc tgctgttccg    540
cgacgtgcac agcctccccg gaaaaaccca gcccgctccc gtcctggtca gcccgacgt     600 caggtgaacg ccatgattcc agacatcgat tcccgtctca gccggaacat attgaaatcc    660
atctcgtatg gcctccccct cgccgaagtg gtccccgacc ataccatgc gcaactggaa     720 acgcgcctcg gcgaactgaa acgcaggtat ctggagctgc gcatctccca cggcgcgcgc    780
gagctgccgt tcagcaacta cctgttctac ctgatcctcc agtcgcgcca ccaggaattc    840
gacttcaagc tgcgccaggg caactcggtg gtcaccaaca tccaccgatt caagagcaag    900
ggacgcatcc cgtccctgac caccctgctc ctggccgatg cggtcaacgc caagagcgag    960
ctggagctca gcatccggga catcccgcag ctcgaccgcc acgctcgcga catcgagcgc   1020
tggctggccg ccggcaacgt catgccgccc agcgagcggg ccctgcgcgg cctggttgag   1080
gcgctggagc gcgccgctgg cgaaggccgt ccgttgcacc tggtgagcgc ggtatgcccg   1140
gactactcgc actccagcga tgccgagggc aagccgcgct acaccttcga gcgagtcggc   1200
gaccagcccg gcctggccgg cgccaagctg gtcagcgccg gccaggcggt ggcggagctg   1260
gccagggcgc gccaggtgga atccgccac gcgatcctcg gcggcgagtt cgagtaccta    1320
tcgttcaacc gcaaccccgc caccggcgag accgcgagg gtttcctcgg caaggtcgag   1380
cgccagctcg agcggatcgc cggggccctg ccctgcccgg ccgcgacctg ctcgttcttc   1440
gagatgtgcg gcggcgagga cggctggcac caggcccacg gcgagatcgt ccagcgcctg   1500
gaacagggcg actacggcca gaccgggctg gactacccgg ccctggaatc gatcttcctg   1560
tcgcgcctgc cgctctacga gaatggttc gccagccagt cgcgcgagca gatctgggcc    1620
agcttcgtct cccaggccgc cgagtacgca ttgatgggaa aactcttcgg cgagcgcttc   1680
gacaacttcg tcgtgctggc cgtcgatcac taccggatgg agccgttcta ctcgttcttc   1740
gcgaccgtcc cgacgctcta catccgaacc gactacctgt aa                       1782
```

<210> SEQ ID NO 3
<211> LENGTH: 693
<212> TYPE: DNA
<213> ORGANISM: Pseudomonas aeruginosa

<400> SEQUENCE: 3

```
atgccgccaa ccagccccac accaaccaac ccgcatccca ggctaccgcc tgatcacaca     60
ggaaacccca tgaatactca gattgcccag atcacccaga gctggcagc caacggctgc    120 gcctatatca ccccagcga cgcgctctac gacgagcagg actgggaact gatgaaccag    180
gtcctggcca actcgaccct gccgtgggag aagatcctga tcggcgacgc cgacgaggag    240
aacgacctct acgtggcccg tttcatgacc gaccgcgacc gtcccacggt ggtcaaccat    300
gcgctgtcgg agctgatcat cccgcgcgt tgcaacgaca acgtgatgag cctgttccgc    360
aagctgatgg gcgacgacgc cttctacgtc cggcgcatgc aggtgaaccg gatgaaggcc    420
```

| | |
|---|---|
| ggctcgttca tcggccggca cctggatacc gacagcaacc cggactacca gtactccatc | 480 |
| gtcctgcagc tcggcaccta cttctccggc ggccagttcg tggtctacga ccgcgacggc | 540 |
| aacctgcgca cgacatcaa gccggagccg cgctcggtga tcatcagcga ctgtagctat | 600 |
| ccccacgagg tccagcaggt gaccgccggc gagcgcgtct cgctggtgtt cttcgtcagt | 660 |
| cgccatgcgg accggaaccg gcgggtctat tga | 693 |

<210> SEQ ID NO 4
<211> LENGTH: 411
<212> TYPE: DNA
<213> ORGANISM: Pseudomonas aeruginosa

<400> SEQUENCE: 4

| | |
|---|---|
| gtgacggact tcgaatcctc gcgtcgcgct ccgtccaccg gattgtccgg cgcgctgcgg | 60 |
| cggccgcgct ccagcgcagc gccactgcca gatctggcag ttgtcgctgg cggggacgga | 120 |
| ggctttagta gccgcacttt tttccagggc cgggcagtgg gaccgcaatg catgacgac | 180 |
| atcgagacca gagtgaggaa actggtagcc gcccggttcg gcgtggagga atgcgacatc | 240 |
| cggctggaca cgcgacttcc g taacgacttc ggtgccgagt cgctcgaggt agtcgaactg | 300 |
| gtcatggccc tggaagcgga gttcggcgtc gagatcgccg atgacgatgc ggaacggatc | 360 |
| gagaccgtgc gccaggccat cgactatctc gaggaagccg tgccgacctg a | 411 |

<210> SEQ ID NO 5
<211> LENGTH: 588
<212> TYPE: DNA
<213> ORGANISM: Pseudomonas aeruginosa

<400> SEQUENCE: 5

| | |
|---|---|
| atggccgtcc gggtcgagga agtagaacga atcgccctcg ctgcggttct gcttccattc | 60 |
| gcgcacgcca tgcgcgcgca gctgcgcggc gaagcgggcg aaatccgcgg cggcgatgcc | 120 |
| gaaggcgtag tgcgtgtagt ccgcggccgg cccgccgtac tgcggctccc gggacaggca | 180 |
| cagccacagc gaacccagtt cgagataggc gccctggtcc cagcgcgctt ccaggcgaaa | 240 |
| gccgagaaga tcgcggtaga aggcgatgct ggccggcagg tcggcgaccg ccagggtcag | 300 |
| gtgattgaga ccggtaagca tggggggctcc ttgcaagatg tggcgggagg tcgattcagg | 360 |
| cacgtcccag ccagtcgccg cggatcattt ccatcagttg gcgcaagccg ggttgcggct | 420 |
| ggcgtcggct cggatagtag aggcagaacg gcgcgcccat cgaggtccag tccggcaata | 480 |
| ccagttgcag ccggccgcta cgcagctcct cggcgattcc cacctccagg cagtaggcca | 540 |
| ggccgacacc gtccagggcc gcggcaaccg ccgtattgct ttcgttga | 588 |

<210> SEQ ID NO 6
<211> LENGTH: 1020
<212> TYPE: DNA
<213> ORGANISM: Pseudomonas aeruginosa

<400> SEQUENCE: 6

| | |
|---|---|
| atgaacggaa ccgccgccga taccctcgcc gtatcgcccc gcccctgcg caacctctgc | 60 |
| gacggccacg gccggctcga tccccgggcg gtcggctggt ccgcccggcc gcgggtgctc | 120 |
| tgccacatcc ccgccacttt cggccggcgc aagcgctgga accactggtg catcgtcagc | 180 |
| cccggctgga tgctctcgct gaccatcgcc gacctcgact acctgaccta cggcgccgcc | 240 |
| tatttcctcg acctggacag cggccaggcg gtagcgcaca cgcagatccg cttcttcggc | 300 |
| ctcggctgcc agttgcccga cgagccgcag gccagccatg ccttcgagca tccccgcctg | 360 |

-continued

```
caattgcgct tcgacgaaca gcccgggcgc ctgcgcgtca ccggccaggc cccggacctc    420
ggtggcctgc cgctggagct ggcgctggaa gtgcgacgac cgtcgcacct ggagtcggtg    480
aacctggtgg tgccgatggg cgaacacacc ttccatgcct gcagccgcca gctcggcctg    540
ccgatcagcg gctgcctgca gctcggccgc cgacgctacg actgccaggc gggccagagc    600
ttcgccgcgc tggacttcgg ccgcggtgtc tggccgctgc atacctactg gacccgcgcc    660
gccttcgccg ccccggcgg catcgccggc aacttcggca ccggctggac cgaagccagc    720
gacctgcgcg agaacgccct gtggttcggc ggcaagctca gccgcgtgct cgacgacgtg    780
cacatccgcg agcctcgcga cccgctggcc gaatggcgcc tggacagcgc ctgcggtcgc    840
gtcgagctgc tcttccgtcc cgaacagctg caccaggcgc ggcccagcgt cggcctgttc    900
tatgccaata cccgccagtg gttcggccgt ttcaacggca ccctgcgcca cgacgacggc    960
gactgcgtgc cggtggacgg cgccctcggc tggatcggtt cgacccgcgc gcgctggtga   1020
```

<210> SEQ ID NO 7
<211> LENGTH: 1170
<212> TYPE: DNA
<213> ORGANISM: Pseudomonas aeruginosa

<400> SEQUENCE: 7

```
atgaaacact actcagccac cctggcactc ctgccactca ccctcgccct gttcctgccc     60
caggcagccc atgcccacgg ctcgatggaa acgccgccca gtcgggtcta cggctgcttc    120
ctcgaaggtc cggagaatcc caagtcggcc gcctgcaagg ccgccgtcgc cgccggcggc    180
acccaggcac tgtacgactg gaatggcgtc aaccagggca cgccaacggc caaccaccag    240
gcggtggtcc ccgacggcca gctctgcggc ccggcaaggg cactgttcaa gggcctgaac    300
ctggctcgca gcgactggcc cagcactgcc atcgcgccgg acgccagcgg caacttccag    360
ttcgtctaca aggccagcgc gccgcacgcg cccgctact cgacttcta catcaccaag    420 gacggctata accccgagaa ccgctggcc tggagcgacc tggaacccgc gccgttctgc    480
tcgatcacca cgtcaagct ggagaacggc acctaccgga tgaactgccc gctgccccag    540
ggcaagaccg gcaagcatgt gatctataac gtctggcagc gctcggacag cccggaagcc    600
ttctacgcct gcatcgacgt gagcttcagc ggcgccgtcg ccaaccctg gcaagcgctg    660 ggcaacctgc gcgcgcagca ggacctgcca gccggtgcta ccgtcaccct gcgtctgttc    720 gatgccagg gccgcgacgc ccagcgtcac agcctgaccc tggccaggg cgccaacggt    780 gccaagcaat ggccgctggc gctggcgcag aaggtcaacc aggactccac cctggtcaac    840
atcggcgtgc tggatgccta cggggcggtc agcccggtgg ccagctcgca ggacaaccag    900
gtctacgtgc gccaggccgg ctaccgcttc caggtcgaca tcgaactgcc ggtcgagggc    960
ggcggcgagc aaccgggcgg cgacggcaag gtcgacttcg actatccgca aggcctgcag   1020
caatacgacg ccgggaccgt agtgcgcggt gccgatggca agcgctacca gtgcaagccc   1080
tacccgaact ccggctggtg caagggctgg gacctctact acgccccggg caagggcatg   1140
gcctggcagg acgcctggac cctgctgtaa                                     1170
```

<210> SEQ ID NO 8
<211> LENGTH: 210
<212> TYPE: DNA
<213> ORGANISM: Pseudomonas aeruginosa

<400> SEQUENCE: 8

| atgttgaaag tggcgatcgt cctgctactg ctggctaccc tggtgagcct gttcagcggc | 60 |
| ctgttcttcc tggtcaagga ccagggccat ggttcccgcg tggtcaattc gctgaccgtc | 120 |
| cgcgtggtgc tcgccgcggc gaccctggtg ctggtcgcct ggggcttcta cagcggcgag | 180 |
| ctgaacagcc acgcgccctg gcatttctga | 210 |

<210> SEQ ID NO 9
<211> LENGTH: 1872
<212> TYPE: DNA
<213> ORGANISM: Pseudomonas aeruginosa

<400> SEQUENCE: 9

| atgagtttcc cgataaacat caattatagg agtttcccta tgtgcggtct cgcgggttgg | 60 |
| gtggattaca cgcgcaagct cgacgacgaa tttccggcga tcttcgccat gaccgatacg | 120 |
| ctcgccttgc gcgggccgga tgccgagggc atctggaagc accgcaacgc cctgctgggt | 180 |
| caccggcggc tggcggtcat cgacctcagc ggcggcgtgc agccgatgtc ctatcgcttt | 240 |
| cccaccggcc aggaggtcac cctcgtctac accggcgagg tgtacaacca cgatgccctg | 300 |
| cgcgagcggt tgcgccgggc cggacatgag ttccgcaccc gcagcgatac cgaggtggtc | 360 |
| ctgcacgcct atctgcaatg gggcgagcgt tgttgcgagt acctgaccgg gatgttcgcc | 420 |
| ttcgccgtct tcgatggccg cgacggccac ctgctgctgg tgcgcgaccg cctgggcatc | 480 |
| aagccgctgt attacgcgcg gcaccgcgag ggactgctgt tcggctcgga gatcaagtcc | 540 |
| atcctggcgc atccggaatt cgccgccagg ctcgacgcgg tcggcctggt cgacctcctg | 600 |
| acgctgtccc ggggcacttc gcagacgccg ttccgcgagg tccaggaact gctgcccggc | 660 |
| cacctgctgt cctggcgtcc caattcccag gcgaagttgc ccgcctactg ggaggtgcgc | 720 |
| cgccaggagc atgccgacga cctgcagagc accgtgcagc gcacccgcga actggtcacc | 780 |
| cgcgccctgg gggcgcaatt gcacgccgac gttccggtgt gttcgctgct atcgggtggg | 840 |
| ctcgattcga ccgccctgac cggcatcgcc cagcgcatcg cgaaggcgga gcacggcggc | 900 |
| gacatcaatt cgttctcggt ggacttcgtc ggccaggccg agcagttccg cagcgacgac | 960 |
| ctgcgtcccg accaggacca gccgttcgcc ctgctggccg cgcagtacat cggcagccgt | 1020 |
| catcgcaccg tgctcatcga caatgccgaa ctggtctgcg aacgagcgcg cgaagaggta | 1080 |
| ttccgggcca aggacgtacc tttcaccttc ggcgacatgg atacctcgct gcacctgatg | 1140 |
| ttcggcgaga tccgccggca ttccacggtg gccatctccg gtgaaggcgc cgacgagctg | 1200 |
| ttcggtggct acggctggtt ccgcgatccg caggcggtgc ctgcggcgcg cttcccctgg | 1260 |
| gcctccaggg tgcgcctgcc ggccggcttc atcgacgccg gtttcaaccg ccgctgcgat | 1320 |
| ctcctccagt accagcaggc cagctacgac gatgggctgc gccaggtcga acacctggcc | 1380 |
| ggcgacagcc cggaggagcg gcggatgcgc gagttcagcc acctgcatct gaagcgctgg | 1440 |
| atggtgctgc tgctcgaacg caaggatcgc ctgagcatgt gcaacggcct ggaggtgcgg | 1500 |
| gtgccctaca ccgaccatga gctggtggag tacgtctaca acgtgccctg gtcgatcaag | 1560 |
| agccgggacg gcgaggagaa gtggctgctc aagcgggcct cgccgactac tgtcccggaa | 1620 |
| gccgtgctca agcgccgcaa gagcccttat ccgacttctg ccaacctcgg ctacgagcgt | 1680 |
| tcctgcgcg ggagcgtgcg gcgcctgctg gaggacgcgg tgaacccggt gttcggcatc | 1740 |
| gtttcgcgag agttcctggc cgccgaactg gagcatccgg agggtactt caacacccag | 1800 |
| gtgagccgcc acaacctgga gaccgcactg gcgctggaag gctggctcag gttgtacggg | 1860 |
| ctctccgcct ga | 1872 |

<210> SEQ ID NO 10
<211> LENGTH: 756
<212> TYPE: DNA
<213> ORGANISM: Pseudomonas aeruginosa

<400> SEQUENCE: 10

| | | | | | |
|---|---|---|---|---|---|
| atgcagaaac | agcgggtggc | cgaccaggtc | gcagagcgta | tcgagcggtt | gatcgtcgac | 60 |
| ggcgtgctca | aggtcggcca | ggcactgccg | tccgagcggc | gcctggtggc | caagctcggc | 120 |
| tgctcgcgct | cggccctgcg | cgagggcctg | cgggcgctgc | gcgggcgcgg | catcatcgac | 180 |
| accgagcatg | ccgtgggtc | gttcgtcgcc | gacctcgacc | gcaacgccga | cgtcagcccg | 240 |
| ctgatgcacc | tgttcggctc | ccagccgcgc | accctctacg | acctgctcga | agtccgcgcc | 300 |
| ctgctggagg | gcgaggcggc | ccgcctggca | gcgctacgcg | gcaccgaggc | agacttcgtc | 360 |
| ctgctcgccc | ggcgctacga | agagatgctc | gccagccacg | aggaaaccca | gccgatcgat | 420 |
| ccccgcgagc | acgcccgccg | cgaccacgcg | ttccaccggg | cgatcagcga | ggcatcgcac | 480 |
| aatccggtgc | tggtgcatac | cctgcaatcg | ctcaacgaac | tgctgctgag | cacggtgttc | 540 |
| gcctcagtga | acaacctcta | ccaccgaccg | ccgcagaaac | gccagatcga | ccgccagcac | 600 |
| gcgcgcctct | acgcggccct | ccgcgagcgc | cagccggacc | aggcgcaacg | ggcggcgcgc | 660 |
| gaacatatcc | acagcatccg | cgacaacctg | cgggagatcg | agcaggaaga | acagcgcctg | 720 |
| gtccgcgcca | ccctgcgcct | gaacggctgg | ggctga | | | 756 |

<210> SEQ ID NO 11
<211> LENGTH: 822
<212> TYPE: DNA
<213> ORGANISM: Pseudomonas aeruginosa

<400> SEQUENCE: 11

| | | | | | |
|---|---|---|---|---|---|
| atgaaccatg | tcatcacccc | ccacagcaag | ctgctcggcg | tcatcgagcc | ggtcctcaac | 60 |
| gacatgcccg | ccggaaccct | gcgccacgca | ctgttccggg | ccttctggga | cgagacggcg | 120 |
| tcgttgctgg | acatcgagga | cgccttcgcc | cgggtcaccg | cccggcgcca | ggcggtcgag | 180 |
| ccgctgcgca | agttcttcgc | cagttggtcg | aagaccaaca | actcggcggc | cagcgtttcc | 240 |
| ggactggcca | atcgccttac | cctgctggcc | cgttcggaac | agggttcggc | agcggcagac | 300 |
| cagctctatc | gagcctgcgg | cagcctgcaa | cggatcaccg | acgaagacct | cggcgccctc | 360 |
| ggcaacaccg | tgcatgccga | tcttttctac | accatggcca | ccaccctttg | cggcgacgac | 420 |
| cgctggctgc | tgcgcgagaa | ctgcctgcct | tcggcgcagg | cgttcaagga | ctggaccgac | 480 |
| cgccagcgcc | tgtgcgagcg | cgacctgatg | cagggactgc | tgaccacgct | ggtacacgag | 540 |
| gtctataccc | acggcgaggt | ggagtacatc | cacccgctgt | acaaggaatg | gttcagccgc | 600 |
| gacatgggcg | tacccgccga | acgcgcccgc | gccaccgtgg | cctgggtaac | ggtgcacacc | 660 |
| ggcggcaccg | agagcaatca | cttcgcccac | gccacggcgg | cggtgaacgc | cttcgtcgag | 720 |
| gcgatggaaa | tcgaggtgaa | cgaagaagcc | gcgcgcaacc | tgttcgggct | ctacctgcgc | 780 |
| aacaaggcgc | aggtcatgcg | tgactgcgcg | gcgctgttct | ga | | 822 |

<210> SEQ ID NO 12
<211> LENGTH: 1368
<212> TYPE: DNA
<213> ORGANISM: Pseudomonas aeruginosa

<400> SEQUENCE: 12

-continued

```
atgtcctccc gccaatcgtc ccgcaacgct tccaccccgt atctgaccaa ggccttccag      60
gcaacggcca tcgtcgtggt gagctacttc ctctactgga cctaccagct ctaccagtac     120
ggcgagattc ccatcagcaa gaaggacgtg atgctgcgcc aagccatcct cgcgcgcttt     180
ccggcggact acgaggtgga gatcaagggc gccgacctgc tcggcttcgg cgagaaattc     240
ctggtcgcct acggcaatcg gcgcttcgtc ggcaaggcct tcgccatgga cgaccaggtc     300
atcgagcgcc tggagcggaa ccaggacgg accaacctgc cgctggtgaa ggtgttctac      360
atcgccgaac ccggcctcct ctcctcgctg ctcaacctct ccccgttcct ggatatccag     420
aagaacatgg tcgagctgag cctccgggaa taccggaaga tccagttggt ccccttcgat     480
ccggacgcga agcggaaacc gcgcgagcag ttcgaaaccg attatgcctt ccccccagctg    540 ttcagcctca gccaactgga agtcgccgac tacgacggcg acggccgcga cgaactgcgc     600
ctgggctacc tgtcctacgc cggcggttcg ggagggacgc gctggtcggt gatctacgac     660
ctgaaggacg cgcgctgac cgcccattcc ggctatccgg aaatgctcga catcgacgtc      720
gcccggttca tccaggcggt caacctgtac gccggcctcg acggcacctt gccgcgcgac     780
cagcgtcagc tggaagacgt ggtcggccga ggcagcgagc gcttcgccct gaccgccgcg     840
gagcgccagg cactggtcgc cgacccgccg cagcgggacg actacgccag ggtcctgatg     900 agccttttcgc gcgctcgcc ctacgccccc gatcgcttca tcgacctcgg cgacggcagc     960
cgactgaccc tggccccgcg ccataccgac gattactcga ccttcctcga catcggcggg    1020
aagaaaatct tcgtcgaagc cttctacgtc gacgacgacg cctgccactg gtgcgagcat    1080
cgctggcgag tgatggcttt ccattacgac gacggtcgct ggatctcgga ccgcaccatc    1140
aacggcgaca gcttcaacgg gcaatggctg cgcaacgcgg agccgctggg cctcaacgac    1200
gttttcggta cctaccgcga ccagggcccg acgggcctgg cctggtcctt catcgacccg    1260
cgctggaccg cctccagcca gcatgacatg gacgatccgc tgggcgtggg aatgcgcacc    1320
ctgtcgccgg tggagcaatg ggtgaaggaa cgctatcggg aaaactga                 1368
```

<210> SEQ ID NO 13
<211> LENGTH: 1209
<212> TYPE: DNA
<213> ORGANISM: Pseudomonas aeruginosa

<400> SEQUENCE: 13

```
atgagcgaac ccatcgatat cctcatcgcc ggcgccggca tcggcggcct cagttgcgcc     60
ctggccctgc accaggccgg catcggcaag gtcacgctgc tggaaagcag cagcgagata    120
cgcccccttg gcgtcggcat caatatccag ccggcggcgg tcgaggccct tgccgaactg    180
ggcctcggcc cggcgctggc ggccaccgcc atccccaccc acgagctgcg ctacatcgac    240
cagagcggcg ccacggtatg gtccgagccg cgcggggtgg aagccggcaa cgcctatccg    300
cagtactcga tccatcgcgg cgaactgcag atgatcctgc tcgccgcggt gcgcgagcgc    360
ctcggccaac aggcggtacg caccggtctc ggcgtggagc gtatcgagga gcgcgacggc    420
cgcgtgctga tcgcgcccg cgacggacac ggcaagcccc aggcgctcgg tgccgatgtg    480
ctggtcggcg ccgacggtat ccattcggcg gtccgcgcgc acctgcatcc cgaccagagg    540
ccgctgtccc acgtgtggat caccatgtgg gcggcgtca ccgagttcga ccgcttcctc     600
gacggcaaga ccatgatcgt cgccaacgac gagcactggt cgcgcctggt cgcctatccg    660
atctcggcgc gtcacgcggc cgaaggcaag tcgctggtga actgggtgtg catggtgccg    720
agcgccgccg tcggccagct cgacaacgag gccgactgga accgcgacgg cgccctggag    780
```

-continued

```
gacgtgctgc cgttcttcgc cgactgggac ctgggctggt tcgacatccg cgacctgctg      840
acccgcaacc agttgatcct gcagtacccg atggtagacc gcgatccgct gccgcactgg      900
ggccggggac gcatcaccct gctcggcgac gccgcccacc tgatgtatcc gatgggcgcc      960
aacggcgctt cgcaagcaat cctcgacggc atcgagctgg ccgccgcgct ggcgcgcaac     1020
gccgacgtgg ccgcagccct gcgcgaatac aagaagcgc ggcggccgac cgccaacaag     1080
atcatcctgg ccaaccgaga acgggaaaaa gaggaatggg ccgcggcttc gcgaccgaag     1140
accgagaaga gcgcggcgct ggaagcgatc accggcagct accgcaacca ggtggaacgg     1200
ccacgctag                                                             1209
```

<210> SEQ ID NO 14
<211> LENGTH: 3090
<212> TYPE: DNA
<213> ORGANISM: Pseudomonas aeruginosa

<400> SEQUENCE: 14

```
atgacctttta ccgacctgtt cgtccgccgg ccggtgctgg cgctggtggt cagcacgctg       60
atcctgctgc tcggcctgtt ctccctgggc aagctgccga tccgccagta cccgctgctg      120
gaaagctcga ccatcaccgt caccaccgag taccccggcg cctccgccga tctcatgcaa      180
ggcttcgtca cccagccgat cgcccaggcg gtgtcgtcgg tggagggcat cgactacctt      240
tcctcgacct cggtgcaggg gcgtagcgtg gtgaccatcc gcatgctgct caaccgcgat      300
tcgacccagg cgatgaccga gaccatggcc aaggtcaact cggtgcgcta caagctgccc      360
gagcgtgcct acgactcggt gatcgaacgc tcttccggcg agaccaccgc ggtagcctac      420
gtcggctttt ccagcaagac cctgccgatc ccggcgttga ccgactacct gtcgcgggtg      480
gtcgagccga tgttctcttc catcgacggc gtggccaagg tccagacctt tggcggccag      540
cgcctggcca tgcgcctctg gctcgacgcc gaccgcctcg ccgggcgcgg cctgaccgcc      600
tccgacgtgg ccgaggcgat ccgccgcaac aactaccagg cggcgccggg gatggtgaag      660
gggcagtacg tgctgtccaa cgtgcgggtc aacaccgacc tgaccaacgt cgacgacttc      720
cgcgagatgg tcatccgcaa cgatggcaac ggcctggtgc cctgcgcga cgtcggtacc      780 gtcgaactgg cgccgcggc caccgagacc agcgcactga tggacggcga cccggcggtg      840
cacctggggt tgttcccgac gcccaccggc aacccgctgg tgatcgtcga cggcatccgc      900
aagctgctgc cggagatcca aagaccctg ccgccggatg tccgcgtcga cctcgcctac      960
gagacttcgc gcttcatcca ggcctccatc gacgaggtgg tgcggacccct ggtggaagcg     1020 ctgctgatcg tggtgctggt gatctacctc tgcctcggct cgctgcgcag cgtgctgatc     1080
ccggtggcga ccattcccct gtcgatgctc ggcgccgccg cgctgatgct ggccttcggc     1140
ttcagcgtca acctgctgac cctgctgcg atggtgctgg ccatcgggct ggtggtggac     1200
gacgccatcg tggtggtgga aacgtccac cgccacatcg aggaaggcaa gtcgccggtg     1260
gcggcggcgc tgatcggcgc ccgcgaagtg ccggcccgg tgatcgccat gaccatcacc     1320
ctggccgccg tgtacacccc catcggcctg atgggcggcc tcaccggcgc gctgttccgc     1380
gagttcgccc tgaccctggc gggcgcggt atcgtgtccg gggtggtggc gctgaccctg     1440
tcgccggtga tgagttcgct gctgctccag gcgcaccaga acgaggggcg catgggccgc     1500
gccgccgagt ggttcttcgg cggcctgacg cggcgctacg ggcaggtcct ggagttctcc     1560
ctgggccacc gctggctgac cggcggcctg gcattgctgg tgtgcatcag cctgccgctg     1620
```

| | | | | |
|---|---|---|---|---|
| ctgtattcga | tgcccaagcg | cgaactggcg | ccgaccgagg | accaggccgc ggtgctcacc | 1680 |
| gcgatcaagg | cgccgcagca | cgccaacctc | gactatgtcg | aactgttcgc gcgcaagctc | 1740 |
| gaccaggtct | acaccagcat | cccggaaacc | gtgagcacct | ggatcatcaa cggcaccgac | 1800 |
| ggaccggcgg | cgagcttcgg | cgggatcaac | ctggcggcct | gggaaaaacg cgagcgcgac | 1860 |
| gcctcggcga | tccagtccga | gctgcaaggc | aaggtcggcg | atgtcgaggg cagcagcatc | 1920 |
| ttcgccttcc | agttggccgc | cctgcccggc | tccaccggcg | gcctgccggt gcagatggtg | 1980 |
| ctgcgcagcc | gcaggacta | tccagtgctc | taccggacca | tggaagagat caagcagaag | 2040 |
| gcccgacaga | gcgggctgtt | cgtggtggtc | gacagcgacc | tcgactacaa caacccggtg | 2100 |
| gtccaggtcc | gcatcgaccg | cgccaaggcc | aacagcctgg | gcatccgcat gcaggacatc | 2160 |
| ggcgagtcgc | tggcggtgct | ggtgggcgag | aactacgtca | accgcttcgg catggagggc | 2220 |
| cgctcctacg | acgtgatccc | acagagcctg | cgcgaccagc | gtttcactcc gcaagcgctg | 2280 |
| gcacgacagt | tcgtgcgcac | ccaggacggc | aacctggtgc | cgctgtcgac ggtggtccgg | 2340 |
| gtggcgcttc | aggtcgaacc | gaacaagctg | atccagttcg | accagcagaa cgccgcgacc | 2400 |
| ctccaggcga | tccccgcgcc | cggcgtctcc | atgggccagg | cggtggcctt cctcgacgac | 2460 |
| gtggcgcgcg | gcctgccggc | cggcttcagc | cacgactggc | aatccgactc gcggcaatac | 2520 |
| acccaggaag | gcaacaccct | ggtgttcgcc | ttcctcgccg | ccctggtggt gatctacctg | 2580 |
| gtgctcgccg | cgcagtacga | gagcctggcc | gacccgctga | tcatcctgat caccgtgccg | 2640 |
| ctgtcgatct | gcggcgcgct | gctgccgctg | gcgctgggct | acgcgacgat gaacatctat | 2700 |
| acgcagatcg | gcctggtcac | cctgatcggc | ctgatcagca | agcacggcat cctcatggtc | 2760 |
| gagttcgcca | cgaactgca | actccacgag | gcctcgacc | gccgcgcggc gatcctgcgc | 2820 |
| gccgcgcaga | tccgcctgcg | gccggtgctg | atgaccaccg | cggcaatggt cttcggcctg | 2880 |
| gtgccgctgc | tcttcgccag | cggcgccggc | gccgccagcc | gcttcggcct gggcgtggtg | 2940 |
| atcgtctccg | ggatgctggt | cggcacccte | ttcaccctgt | tcgtgctgcc caccgtctat | 3000 |
| accctgctgg | cgcgcaacca | cgcggaagtc | gacaagagcc | cgcgcagccg gcaactggcc | 3060 |
| gaggccgatc | tgctggtgaa | caaggcatga | | | 3090 |

<210> SEQ ID NO 15
<211> LENGTH: 2535
<212> TYPE: DNA
<213> ORGANISM: Pseudomonas aeruginosa

<400> SEQUENCE: 15

| | | | | |
|---|---|---|---|---|
| gtggccgttg | cgtcaccggc | cggcgggttg | gacgcaccgt | cgcggcggat cgtcttcgac | 60 |
| gcgcagatgc | tggccctggg | gccgggcgga | cgctcgatcg | atacgtcgcg tttcgagcgc | 120 |
| ggcgacgtca | tcgagccagg | ccgctatcgc | ctcgacctgc | tgctcaacag ccgatggcgt | 180 |
| ggcgtcgagg | aagtcgagct | gcgccgccag | ccggggcgga | aaagcgcggt cttctgctac | 240 |
| gaccggggcc | tgctggagcg | ggcgggcatc | gacctggaga | gagcgcgcg tggccaggac | 300 |
| cgttcctcgg | ctcgcgatcc | tctgcccgaa | ggtttgcact | gcgaccctct cgagcgctat | 360 |
| gtgccgggg | cccgggtcaa | gctcgatatc | gccgagcagt | cgatctatgt ctcggtgccc | 420 |
| agctattacc | tgagcctgga | ttcttcgaag | acctatgtcg | atccggcgag ctgggacagc | 480 |
| ggcatttccg | ccgccttgct | caactacaac | agcaatctcc | acgtcaggga aaaccacggc | 540 |
| aggagcgcca | ccagcggcta | tgccgggatg | aacgccggct | tcaatttcgg gcgggcgcgc | 600 |
| ctgcgccaca | acggcacggc | cacctggtcg | cgccgcatgg | gcagccatta ccagcgtagc | 660 |

-continued

```
gcaacctatg tgcagaccga cctgccggcc tggcgtgcgc agttattgct gggagaaaac      720
tccaccagca gcgagttctt cgatgcggtg tccttccgtg gagtgcagct atccagcgat      780
gaccggatgc tgccggattc gctgcgctac tacgctccgg tggtccgtgg gaccgccagt      840
accaatgcgc gggtatcggt ctaccagcgc ggctacctca tctacgaaac cacggtggca      900
cccggggcgt tcgctctcga cgaactgcag accgccagct atggcgggga cctggaagtg      960
cgggtgaccg aagccagcgg ggaagtccgc agtttcatcg tgccgttcgc caccaccgta     1020
caactgctgc gccccgggac cacgcgctac agcctgacgg ccgggcggct caacgatccc     1080
agcctggagc gtcggccgaa catgctgcag ggcgtctacc agcgcggcct gggcaacgac     1140
gtcaccgcat acgcgggcgg ggccttcacc ggcagctaca tgtccgggtt gatgggcgcg     1200
gcgctgaaca cgccggtggg cggattctcc ggtgacgtga cgctggcgcg taccgaggtt     1260
cccggcgacg accgccttag cggctccagc taccgtctcg cctacagcaa gaacctgccg     1320
aacaccggca ccaactttc gctgctcgcc tatcgttact ccaccggtgg ctatctcggc      1380
ctgcgcgacg cggccttcat gcaggaccgg gtagagcgag gcgagccgct ggagtcgttc     1440
tcgcgcttgc gcaatcgtct cgacgccaac atcagccagc aactgggcaa cggcggcaac     1500 cttttacctga cggctcctc gcagcgctac tggagcggcg gcgggcgggc ggtcaacttc     1560
tccgtcggct acagcaacca gtggcgcgac gtcagttact ccatttccgc gcaacgcctg     1620
cgcagccagt acgaaggctt ttccagcggt gacaggcgcg gcgagaccag cacgctgttc     1680
agcctgaacc tgtccattcc gctcggcggc gctggacgcg ggtcgccgac cctgagcagc     1740
tacctgaccc gcgacagcaa cagcggaacc cagctcacca gcgggtttc cggcatgctg      1800 ggcaagcgtg gcgaggcctc ctactcgctg tcggcctccc atgaccgcga cagccggcag     1860
acctcgaaga gcgccagcct cgactatcga ctgccgcagg tcgaactcgg ctccagcctc     1920
tcgcagggac cgggctatcg gcagttgtcg gtcaaggccg cgggggggcct ggtcgcgcac    1980 agcggcggga tcaccgcggc acaaaccctg ggcgagacga tcggcctggt ccacgcgcca     2040
aatgccaggg gcgcggctgc cggctactcg ggaagccgga tcgaccgcca cggctatgcg     2100
gtgattccca acctgctgcc ctaccagttg aacagcgtcg acctcgaccc caacggcatg     2160
gccgacgaga tcgaactgag gtccagttcg cgcaacgtgg cgcccaccgc cggagcggtg     2220
gtgcgcctcg actatccgac gcgggtggca aggcccttgc tggtggatag ccggatgccc     2280
agcggcgagc ccctgccgtt cgccgcggaa gtgctcgatg cccacagcgg gcagtcggtg     2340
ggcgccgtcg gccagggcag ccgcctggtg ctgcgggtcg agcaggatcg cggctcggtt     2400
cgggtgcgct ggggcaacga gccgcagcag cagtgcctgg tcgactatgc gttgggcccg     2460
cgcgagacga cgcctcccgt cctgcaactg gcatgtcgcc cggcgtcggc cgccgaccgg     2520
gagcgcacgc tgtga                                                      2535
```

<210> SEQ ID NO 16
<211> LENGTH: 2976
<212> TYPE: DNA
<213> ORGANISM: Pseudomonas aeruginosa

<400> SEQUENCE: 16

```
atgtcgaaag attctgttct tggcttattc aggcaacacg cagatacccca tcccgaacgc      60 cccgccctcg tcgatcgcga gcgctcgttc agctaccgcg aactcgaccg gctcagcgac     120
cggctggccg cccacctggc caggcgcggc gtcgcccggg gcgagctgct gccccctgctg    180
```

```
gccgaacgct cggccgaact ggtcatcgcc atcctggcgg ccgccaagtg cgcagcggcc     240
tacgtaccgg tggaccgtcg gcaacccgac aggcgcaagc gggaagtcct ccgccagtgc     300
caagccccct tggccctcgc cacccatgcc gaggacctgc cggggcaacc ggtggaggtc     360
atcgcacagg cgctcgcgac gagtgcggcg ggtgccgcgc cgagaccggc gctcgacggc     420
agcgaagcgc tgtatgtgat cttcacctcg gcaccaccg cgaacccaa gggcgtggtg       480 atcgagagtc gctccctggc caacctcgtg ggctggcaca accggcgctt caatatggat     540
caacggagcc gcaccaccct gatggccggc gtcggcttcg acgtttccca atgggaaatc     600
tggtccaccc tgtgcgcagg cgcctgcctc cacctggtgc cgacgaggt gcgcccagac      660 ccggcggcgc tgctggcatt cttcgccgag cagcggatca gccacgcctt cgcgcctacc     720
gtgatggtgc ccgcgctggc ggagcagccc gccccgccgt cgctggcgct cgctacctg     780 ttctgcgccg gggaaaaact gccgccggtc gcaaccggcg ggctgcccta taccgtggtg    840
gattactacg gcccgaccga ggccacggtc ttcgccacct gccgcatcgt cgacgccgaa    900
gcacatcggc gacccgcctc gatcggcacg cccatcgacg gctgcgaggc attcatcctc    960
gacgccgacg accggccttg ccatggcgac cgacccggtg aactgaacct ggcgggcgtc   1020
tgcctggcgc gcgaatacct gcgcgacccg gacatgaccg ccaggcgctt ccactactcg    1080
caggcactgc ggcgtcggct ctaccgcacc ggcgacaagg cccgctggtt ggccgatggc    1140
agcctgcagt cctcggtcg gctggacgac caggtgaaga tccgcggcca ccgcgtcgaa    1200
ctcggcgacg tcgaggccgc gctgttgcgc cagccggcta tccacggcgc ggtggtgctg    1260
gcgcatgccg acccacgctc cggtagccag caattgagcg ccttcgtggt ccccgccag    1320 caggacggca tgccaggc cgtgctcgcc gccatcaaga ccgcactgcg ccaggaactg      1380
cccgactaca tgctgcccag ccgctacctg tcgctggaca gcctgccgac cacggtcaac    1440
ggcaagatcg accgccaggc cctgcgtcga cacctggacg aacaatgcca ggaacgactc    1500
gacgagcaac gcttcggcac ccccggcgaa ctgcaagtgg ccctgtcctg caggaagtg    1560 ctggggcata ccgacttcgg cctggacgac agcttcttcg aggtcggcgg ccattccctg    1620
ctggccgccg ccctggtgcg cgaattgagc cgacgcttcg gcaaccgtgc ctacatccac    1680
gacatctacc gcaccccgag cgtgcgccaa ctggcggcca gcctggcgcg cgcgccggc    1740 gaagcgccgc cggcgctgga cagcgaaccg gcccaggagc tgcaacggga cgtgcgcctg    1800
cccgccgacg tggatttcag ccgccccacg gacaccgccc aattgctggc gccacggcac    1860
atcctgctca ccgcgccag cgggctgatg gcgcccacc tgctcgccga gctgctggcc    1920
agccgcgagg ccgacctgca ttgtccggtc cgtgcgcaaa acgacgccca tgccctcgaa    1980
cgcctgcgcc aggccgcccg gcagcaccgc atcgaactcg ccgagacgga ctggcgacgg    2040
gtcagggcct acgccgccga cctcgcagaa ccaggtttcg gactaccggc ggaaacctat    2100
cgcgagctgg ccgcagcgt cgaccaggtc ttccattccg ccagcgcggt gaacttcatc    2160
cagccataca gctacatgaa gcgcgacaac gtcgaggggc tcggccaggt cctgcgcttc    2220
tgcgccagcg gccgctgcaa gccgctgatg ctgctgtcga gcatctcggt gtacagctgg    2280
ggccacctgc ataccggcaa gcgcctgatg cgcgaggacg acgacatcga ccagaacctg    2340
ccggcggtgg tcaccgacat gggctacgtg cgcagcaaat gggtgatgga aaagatcgcc    2400
gacctcgccg ccgaacgcgg cctgccgctg atgaccttcc gcctcggcta cgccacctgc    2460
cacagccgta ccgcgccta cgccgactac cagtggtgga gccggctggc gcggacctgc    2520
ctggagtacc gggccgtgcc gctcctgcgc gagctgcgcg agggcctgac cacggtggac    2580
```

-continued

```
tacatggtag aggcgatcag cgtcatcgcc cgccagcctt cggcgctggg caagaaattc      2640
aacctggtgc cgagcattcc gcgctgcctg accctggacg agttcttcgg ccgtctcggg      2700
cgacgcgccg ggcgtcccct tcggcagatg ccgttcgacg actgggtaag tctctgggaa      2760
gacaatcgcg acgcccgct ctatcccctg ctgagcatgt ccgcgacaa catgtacgcc        2820 ggccgcagca ccgtcgagtt gtaccaggac acctatctct gggactgcac caacgtcgag      2880
gaacacctgc gcgggagcgc cgtgcgcgag ccggagttcg acgaccgcct gctcgacctg      2940
tacctcgccg gcctgggcgg cagcgccatg cggtaa                                2976

<210> SEQ ID NO 17
<211> LENGTH: 1092
<212> TYPE: DNA
<213> ORGANISM: Pseudomonas aeruginosa

<400> SEQUENCE: 17
gtgggacggc ttcgacgagc cgcgctgcac cctgctggag gcgaaggcca actacgcctt        60
cctgttcgtc ccgctgctcg gcgtgcccag gccctgggca cgggccaagg tgaagtcgga      120
cctgctgcag aaggccgagg tccacagcga caaggcccga ccgaccccgc cggtgttcgt      180
cgaatggcac ttcctgcagc ggatcgtcta cgagtactgc gccgcggagt acctgcgcat      240
gggactggcc aacctgaagg cattctggaa tccgatgccg gaacggacg agcacgacga       300 ctaccaggaa acccgcgcga aggaacagga agagatgaaa aggttttgcg aagagaaccc      360
ggggtattgc gcatgacgga cgccaaggct ttcaggcgct acatattcga gctgtacttc      420
gatccggcac ggctcctcga actggacgac gaccagcacc tgcaacggat agaacgcttc      480
ctcgatgccc tcgcgcccct ccatccggtg ctggagaact ggtatctgtg cggcgactcc      540
ctgcgcgatg ccctcagcca acgtcacc gagcaccgcc aggatctcgc caaggccctg        600
tcgcgtgacc gacgcacccg ggcggtggaa ctggtgctat ggaacggcga ggaggatccg      660
ctcaagggcg ggttgtcgct ggactacgag gccagcggca gggccgtctc gtccaggctc      720
cagttggaag atgccggcag cctgctgcag gtgttcgacg caccggcgtc ctccttcgtc      780
gcgatcttcc tcgcggtgct ggaaatctgg cccgaaacga cctggggcat gctcgctccg      840
catgcgtact tcgtacacca gcggaccttc ccggaccgcc gcagcatcgg ctggatcggc      900
ttctgcccgc atccgctaag ggccacggac ttcccggcgg ctacggagct ggtcgacatt      960 cccgccgtg gcaccctgct gctgaacggc gcgaaccga tggacgaaac ccgtcgcgaa       1020
catttcgagc gcgtcggcga agcggacatc aagctgatgg aactgggcta cctgccgccg      1080
ctgcgcggct ga                                                         1092

<210> SEQ ID NO 18
<211> LENGTH: 1281
<212> TYPE: DNA
<213> ORGANISM: Pseudomonas aeruginosa

<400> SEQUENCE: 18
atgcacgcca tcctcatcgc catcggctcg gccggcgacg tatttcccTT catcggcctg        60
gcccggaccc tgaaactgcg cgggcaccgc gtgagcctct gcaccatccc ggtgtttcgc      120
gacgcggtgg agcagcacgg catcgcgttc gtcccgctga cgacgaact gacctaccgc       180 cggaccatgg gcgatccgcg cctgtgggac cccaagacgt ccttcggcgt gctctggcaa      240
gccatcgccg ggatgatcga gccggtctac gagtacgtct cggcgcagcg ccatgacgac      300
```

```
atcgtggtgg tcggctcgct atgggcgctg ggcgcacgca tcgctcacga gaagtacggg    360
attccctacc tgtccgcgca ggtctcgcca tcgaccctgt tgtcggcgca cctgccgccg    420
gtacacccca gttcaacgt gcccgagcag atgccgctgg cgatgcgcaa gctgctctgg    480
cgctgcatcg agcgcttcaa gctggatcgc acctgcgcgc cggagatcaa cgcggtgcgc    540
cgcaaggtcg gcctggaaac gccggtgaag cgcatcttca cccaatggat gcattcgccg    600
cagggcgtgg tctgcctgtt cccggcctgg ttcgcgccgc ccagcagga ttggccgcaa    660 cccctgcaca tgaccggctt cccgctgttc gacggcagta tcccggggac cccgctcgac    720
gacgaactgc aacgctttct cgatcagggc agccggccgc tggtgttcac ccagggctcg    780
accgaacacc tgcagggcga cttctacgcc atggccctgc gcgcgctgga acgcctcggc    840
gcgcgtggga tcttcctcac cggcgccggc caggaaccgc tgcgcggctt gccgaaccac    900
gtgctgcagc gcgcctacgc gccactggga gccttgctgc catcgtgcgc cgggctggtc    960
catccgggcg gtatcggcgc catgagccta gccttggcgg cggggggtgcc gcaggtgctg   1020 ctgccctgtg cccacgacca gttcgacaat gccgaacggc tggtccggct cggctgcggg   1080
atgcgcctgg gcgtgccgtt gcgcgagcag gagttgcgcg gggcgctgtg gcgcttgctc   1140
gaggacccgg ccatggcggc ggcctgtcgg cgtttcatgg aattgtcaca accgcacagt   1200
atcgcttgcg gtaaagcggc ccaggtggtc gaacgttgtc ataggggaggg ggatgctcga   1260 tggctgaagg ctgcgtcctg a                                             1281

<210> SEQ ID NO 19
<211> LENGTH: 651
<212> TYPE: DNA
<213> ORGANISM: Pseudomonas aeruginosa

<400> SEQUENCE: 19
atgccgcctt tttttctcg gccggcacga cacggggact tggtcatgat cgaattgctc     60
tctgaatcgc tggaagggct ttccgccgcc atgatcgccg agctgggacg ctaccggcat    120
caggtcttca tcgagaagct gggctgggac gtggtctcca cctccagggt ccgcgaccag    180
gaattcgacc agttcgacca tccgcaaacc cgctacatcg tcgccatgag ccgccagggc    240
atctgcggtt cgcccgcct gctgccgacg accgacgcct acctgctcaa ggacgtcttc    300 gcctaccgt gcagcgaaac cccgccgagc gatccgtcgg tctgggagct ttcgcgctac    360
gccgccagcg cggcggacga tccgcagctg gcgatgaaga tattctggtc cagcctgcaa    420
tgcgcctggt acctgggcgc cagttcggtg gtggcggtga ccaccacggc catggagcgc    480
tatttcgttc gcaacggcgt gatcctccag cgcctcggcc gccgcagaa ggtcaagggc    540 gagacgctgt cgcgatcag cttcccgcc taccaggagc gcggcctgga gatgctgctg    600
cgctaccacc cggaatggct gcagggcgta ccgctgtcga tggcggtgtg a             651

<210> SEQ ID NO 20
<211> LENGTH: 1167
<212> TYPE: DNA
<213> ORGANISM: Pseudomonas aeruginosa

<400> SEQUENCE: 20
atgcctttga ttgtctatgt gctcggtgcc gcgatcttcg ccctgaccac cagcgaatac     60
atggtcgccg ggctgatgcc ggcgctggcc gccgaattcg gcgtgtcctt cgccgcgatc    120
ggctacctgg tcaccttcta cgccggtgcg atggccgtcg gcggcccgct gttgaccacc    180
gccctgctcc gggtgccgcg caagaacgcc ctgctcggcc tgatcgcgct gttcgtggtc    240
```

```
ggccaggtca tcggcgccct ggcgccgggc tatgcggtga tggtcgcggc gcgactggtc        300
accgcggtcg ccgccgcggc cttcttcggc gtggcgctga ccgcctgcgc cgaactggtc        360
gaaggcaacc agttcggccg cgcgtcgtcg ctggtgctcg gtggcctgat ggtcggcacc        420
gtgctcggcc tgcccgtcgc cacctggctg gcgaatggt acggctggcg cgcgagcttc         480
ttcgcggtgg cgctggtggc ggtgctggtc ggcctgctgg tgttgcagct gatgccggcg        540
atcccggggt cggcgggcag cggctcgctg cgcgaggaac tgaaggtgtt caggaacgcc        600
catctatggt gggtctacgc caccagcctg ctgctgatcg gcgccaccttc gccggcttc        660 acctatttcg tgccgatcct caccgaggtc agcggcttct ccgcctcgac cgtaccgctg        720
ctgctggtgg tctacggcct ggcgacgctg gtgggcaaca acatcgtcgg ccgcctggcc        780
gaccgccata ccatcgcggt cctggccttc ggcctgctgg cggccatcgc cgcgatggtg        840
gccttcgccc tgttcggaca ggttccggcg gtggcggtgg cggcgctggt ggtgatcggc        900
ctgaccgggg tgtcgatgaa cccggcgctg gtgacccgcg cgcacgggt cggccataac         960 aacatgctgg tcaactcggt gcacactgcc tgcatcatgc tcggcgtaat ggccggttcc       1020
tggatcggcg gcctgggcat cgccggcgga ttcggcctgc agggcgcgct ctgggtcggc       1080
gcggccctcg gagtactggc gctgctgacc ctgctgccgg agctgcgctt cgcccgcgcc       1140
ccggtaggcg gggcgctggg ccgctga                                          1167

<210> SEQ ID NO 21
<211> LENGTH: 993
<212> TYPE: DNA
<213> ORGANISM: Pseudomonas aeruginosa

<400> SEQUENCE: 21
atgccgcgcg ccgccgtggt ctgcggcctg ggcagctacc tgcccgaggc cgtgctcagc         60
aacgacatgc tcgccgccga gctggacact tccgacgcct ggatcagcag ccgcaccggc       120
gtgcgccagc ggcatatcgc cggcgacctc ggcagcggcg acctggccct gcgggcggcc       180
tccgccgcgc tcgcctcggc ggggctggag cgagtcgatg cggtggtgct ggcaaccagc       240
accggcgact tctgctgccc ggccaccgcg cccagggtcg cggcgcgcct ggggttggtc       300
ggcgcgctcg cgttcgacct gtccgccgcc tgcaccggct tcgtctacgg cctggccagc       360
gtcggctcgc tgatcagcgc cgggctggcg gacagcgcgc tgctggtcgg ggtggacact       420
ttcagccata ccctcgaccc cgccgatcgc tcgaccccgcg cactgttcgg cgacggcgcc       480
ggagcggtgg tgctgcgtgc cggcgatgcc gaggaagaag gcgcgctgct ggccttcgac       540
ctcggcagcg acgccacca gttcgacctg ctgatgaccc ccgccgtcag tcgcgccgaa        600
cgcagttccg gacaggcctc caactacttc cggatggacg gcaaggcagt gttcggccag       660
gcggtgacgc agatgagcga ctcggtgcgc gggtgctcg accgggtcgg ctggcaagct       720
tcggacctcc atcacctggt cccgcaccag gccaacacac gcattctcgc ggcggtcgcc       780
gaccagctcg accttcccgt cgagcgagtg gtgagcaaca tcgccgaggt gggcaatacc       840
gtcgccgcct cgattcccct ggccctggcc cacggcctgc gccaaggcat cctgcgcgac       900
ggcggcaaca tggtcctcac cggtttcggt gccggactga cctggggttc ggtcgccctg       960
cgctggccga agatcgttcc gacaatggac tga                                   993

<210> SEQ ID NO 22
<211> LENGTH: 1257
<212> TYPE: DNA
```

<210> ORGANISM: Pseudomonas aeruginosa

<400> SEQUENCE: 22

```
gtgcctgatc gcaaactgag actgggcgag gaactgatct cgccactgca cgcgctctac      60
gacggcctgc aggtggacgg cgcgccgcgt cccgcgcatc gcgccgccga gcatccggtg     120
tgggtggtga cgcgctaccg cgacgcgcgc aaggtcctca accatccggg cgtccgccgc     180
gacgcccggc aggccgccga actctacgcg aagcgtaccg gcagcccgcg cgcggggatc     240
ggcgagggac tcagccacca catgctcaac ctcgacccgc cggaccatac ccgcctgcgc     300
tcgctggttg gccgcgcgtt caccccgcgc caggtggagc cctgcaacc gcatatagaa      360
cggatcaccg aggcattgct ggacgccatg gccggccgcg aacaggccga cctgatggcc     420
gacttcgcga tcccgctgac catcgcgtg atcttcgagc tgctgggcat cccgaggcc       480
gagcgcgaac acgcccgcca gtcctgggag cgccaggcgg aactgctgtc gccggaggag     540
gcccaggccc tggccgatgc gcaggtcgac tacctgcgcg tgctgctcga ggccaagcgc     600
cggcagccgg ccgacgacgt ctacagcggg ctggtgcagg ccgccgacga gagcggccag     660
ttgagcgaag cggaactcgt ctccatggcc cacctgctga tgatgagcgg cttcgagacc     720
accatgaaca tgatcggcaa cgcgctggtc accctgctgg tcaacccgga gcaactggcg     780
ttgctgcggg cgcagccgga actcctgccc aacgccatgg aagaactggt ccgccacgac     840
agtccggtgc gcgcctcgat gttgcgcttc accgtggaag acgtggaact ggacggggtc     900
accattcccg ccggcgaata catcctggtc tccaacctga ccgccaacca cgatgccgag     960
cgcttcgacg atcccgaccg cctcgacctc acccgcaaca ccgatggcca tctcggctac    1020
ggcttcggcg tgcactactg cgtcggcgcc tcgctggccc ggctggaggg gcggatcgcc    1080
atccagcgcc tgctcgcgcg cttccccgac ctccagttgg cggtgcccca cgcggagctg    1140
cagtggctgc cgatcacctt cctccgcgcc ctgatcagcg tgccggtgcg caccggatgc    1200
agcgccccgg cgaacaccgc ctcccacgcc aacccgatcg agaggatcgc ccaatga       1257
```

<210> SEQ ID NO 23
<211> LENGTH: 915
<212> TYPE: DNA
<213> ORGANISM: Pseudomonas aeruginosa

<400> SEQUENCE: 23

```
atgttattca ccagcaaacc tctctcgccc cagggccgcc acgtactgat caccggcgcc      60
tccagcggcc tcgccgggga aaccgcgctg cacctggcca acagggtttt ccaggtgatc     120
gccggggtgc gccgccagga ggatggcgag cgcctggcga acgcctgccc gtccggccgg     180
atcagcacgc tgctgatcga tgtcaccgac gaggaatcca ttggccgggc cgccgcgcag     240
gtggcggaga agtcggcga taccgggctc tggggcctgg tgaacaacgc cgggatctgc     300
atttccgcgc cgctggaatg cgtctccagc gacctgctgc ggcgccagct ggaagtcaac     360
ctgatcggcc agctcgcggt gacccggggcg atcctgccgc tgctgcgccg tggcggcgcg    420
gcgcgcctgt gaacgtcac ctcgggcctc ggctcggtcg ccattcccta cctgggcgcc      480
tactccgccg cgcagttcgc caaggaggga gtgagcgacg ccctgcgccg cgagctggca     540
cccatgggca tccaggtctc ggtggtcagc ccggggcga tctggacgcc gatcggggc       600
aagatcgcca gcgagggcga gcgcgccctg gccgacgccc cgacgccgt cgccgacctc     660
tatcgcgata cctacctgcg cttcctccag gccaacgagg acggcgcgcg caacagcgcg     720
accaagcccg ccgatgtcgc cgccgcggtg catgccgcgc tcaccgcggc caagccgcgg     780
```

-continued

```
acccgctacc gggtcggcgc cgacgtgcgc cgcggtaccc tgctggcgcg gctgctgccc    840
gatagcgtga tcgacgggat gttccgcccc atcgtcaccg ccgccccggc ggcgaaggag    900
gagcaacgtg cctga                                                    915
```

<210> SEQ ID NO 24
<211> LENGTH: 1329
<212> TYPE: DNA
<213> ORGANISM: Pseudomonas aeruginosa

<400> SEQUENCE: 24

```
atgatggccg agatacgacg cccgctgtcc gcggtggaac gctggtactg gctcagcgac     60
cagttctccg cgctgaacgt gatttcccgg gtgcgggtcc atggccggtt gtccatcgac    120
gacctgcgcc gcggcctcga cgcgctgcag gcgcggcatc cgctgctgcg cgcgcggatc    180
gagcacgatg ccgggctcga tccgcgctgg gtgccctgcg agcggcccat ccgctgcgc     240
gaggtgcgcg gcggcggcga ggagcaatgg ctgcgggaaa tcaacgagcg cgaattgccg    300
gaacgcatcg atccggacag cgggccactg atccgtaccg tggcgatcgc caccgacgcc    360
ggcgcccacg acctgctggt cgtggtaccg cacatcatcg ccgacggcac taccgtgctg    420
accctcgccg aacaatggct gaccctggcc gccgaccccg ccgcgcaacc ctggaccgcc    480
agcgccctgc cgccggcgga ggatctgcgt ccgcgccgct tcaccggcga cgaaggcgcg    540
gcgcgcctgg ccgagcagac cgcccaggac gaagcgctgg tcggccgcca ccgcccgggc    600
cggatcgagc cgagcaaccc ggtgccgctg aagcgcggc gtaccgcct gctgcaccgg    660
gagctggacg gcgcgcagct ggaacagctg caacgacgcg cccgcgaaca cggcaccacg    720
gtacacggcg cgctgaccgc ggcgctggcc atcgccgccg ccacgaccac ccagcgccgc    780
cctagccaca tcgccatcgg ctcgccgatc gacttccgcg acgaactgga gccgccggtg    840
cgccccgacg aagtaggcac ctacgtcgcc acggtaccgg tggtgctgga catcgcccgg    900
ccgttctggg aggtcgcccg cgcgctcacc gacgacctcg gcgaacgccg tcgccagggc    960
catcatttca acctggtcac cctggtcgcc agcgctgcgc cgcgctgcat ggccgacgcg   1020
cggccattca tggccttcat ggaagccgaa gggccgatca acctgtgctc ctccaacatc   1080
ggtcgctatc cgttccccga gcggatcggc gccttgcgcc tctccgacgc gcagttcctc   1140
accggcatct cggtgaacgg ctacttcgtg gccgccatca actccagcca tggccggctg   1200
ttctggaact tcacctatat cgacgaagcg gtccccggcg aacgcgccga acgcctggcc   1260
gaagattgcc tgggcaccct gctgtcggcg atccacgccc ccaacgatc cgccctcgag   1320
gagcaatga                                                          1329
```

<210> SEQ ID NO 25
<211> LENGTH: 1167
<212> TYPE: DNA
<213> ORGANISM: Pseudomonas aeruginosa

<400> SEQUENCE: 25

```
atgagcagac atcccctgaa gatcgtcatc gccggcgccg gcatcggcgg gctcgccgcg     60
gccgcctgcc tgaaagccgc cggcttcgag gtcgaactct acgagcgggc cagggagctg    120
cgcgcggtcg gctcggcgct gtcgctgatg cccaacgcgc tgaccgccct ggagagggtc    180
ggcgtgcgcc ctgaccttac ccgcgcccag gccttcgact cgctgcggtt cctcacccgg    240
cgcggggcgac cgatccgcgc catcgacttc ggcggcctgg cccgtcagct cggccagccg    300
```

```
agcctggcga tccaccgcgc gagcctgcag caggcgctgc tggaacaggc ccgcgactgc      360
cgcatcgaac tgggcgtgag cgccaccggc tacctgcgcc acgccgacgg cgaaggcgtc      420
accgtgctct gcagcgacgg ccgcgaagtg cacgccgacg tgctgatcgg cgccgacggc      480
ttcaactcgg cgatccgcgc caccatgacc ggcccggagc gtcccaccga ctggcactac      540
gtgatctggc gtgccacgcc ggcgttccgc catccgaagg tgacgccggg ctacgtcgcc      600
cattactggg gccgtgggca cgcttcggt ctcgccgaca tcggcgaagg caacgtctat       660
tggtggggca cccgcaacat gccggccgaa caggcgaagg actggcgcgg cggcaaggcg      720
ggcatccagc gcctctacgc cggctgggcc gacgaagtgc aggcggtcat cgaggcgacc      780
ccggaggccg acatcagcag cctgccggcc caggaccgac cgttcctgga gcgctggggc      840 gacgcccgg tgaccctgct cggcgatgcc gcgcatccga tgctgaccag cctcggccag       900
ggcgccgcca tcgccatcga agacgccgcg gtgctggccc actgcctggc caccatcgac      960
gacccgcaag ccgccctgcg cgcctacgag aaccgccgtc gcgaccgcgc cagggcgatg    1020
gtcgagacct cgcgggcgct gagccgcatc gagcagttgg agcatccgct gcgcaccgtc    1080
gcccgcgatc tctacttccg cttcgctccg gagcgaacct tcgcccggca gaacgaactg    1140
gcactgacct tcccaggagt cgaatga                                        1167

<210> SEQ ID NO 26
<211> LENGTH: 7110
<212> TYPE: DNA
<213> ORGANISM: Pseudomonas aeruginosa

<400> SEQUENCE: 26
gtgcggtgcc cgtgttcgcc gaatcgatgg attgttgaag aggacgcagg gatggttcgt       60
ttcgctcgct tgccgctatc gccctaccaa cgggacatct gggtcgccgc cgcgcagttt      120
ccggaactcg accagtacac catcttcagc tacgaccgct tcaccggcga ggtcgatacc      180
caggccctgg aacgagcgct gctgcaggcg gcgcgagaca ccgaggcgtt ccgcctgcgc      240
ctcggcgaga cggacggtac gccgtaccag tggctggaca cggatgccga gttcgaggcg      300
cgccacgtcg acctgcgcgc cgaccgcgac cccgaggccg ccgtgcgatc ctggctgcgc      360
gacgccttcc gtcacgccta cccgctggac ggccgcagcc tggtggacct ggccctgctg      420
catagcgacc aggcgctcta cgtctacgtg cgcacccacc atatcgtcag cgacgcctgg      480
ggcctgcagc tattcctcag ccgggtgcgc gccggctacc tgggtgagct aggcgagccg      540
caggcgcaga tgccgacggc ttccctcctg gcgcagctca agaccgacga ctactccggt      600
tcggaacagt accgcggcga ccgcgcctat ttcgccgagg ccctggaggg cctggagccg      660
gccctcttca cccgcaggcg cccggccggg ctgccgcgca ccgcgcgcca caggctgacg      720
ctggaacgca cactgctcga tgcgatccgc gatcgtggcg aatcgcccgtt cctgttcctc      780 tccgccgccg tggcgctgta cctggcgcgg atccaccaga acgacgacgt ggtcctcggc      840
gtaccggtgt tgaaccgcgc cgaccgcgcg gccaagcaag tggtcgggca cttcgccaat      900
accctgccgc tacgcatccg caccgcgccg gaacagaccg tcgacgaatt cctggcgcag      960
ttgcgcgagg cgaccccgga cgctgctgcg caccagaaga tgcccctcgg cgacctgttg    1020
cgcggcgcct cgccactgtt cgacaccacc ctttcctaca tgcgctggcc cgccgcccag    1080
gcgatcccga acgccagcgt cgagaccgtg cgcaaacccc acgccatga cccggacgcg      1140 ctggccatct gggtctccga gttcgacggg cacagcgacg cgcaggtgga tttcgaatac    1200
gcctgcgatg tgttcgacgc cgacttcccc atggacgccg cggcgcggca tatcgaaacc    1260
```

```
ttcctgcgcg ccctggtgga gggcggcgag cgccgcctcg gcgaactcga tccgctgtcg    1320
gccgccgagc gcgaggaact gatccacacc cgcaacgcca ccgaccaggc attccccgag    1380
caggctaccc tgcccacact gttcgccgag caggtggcgc gcaccccgca acgcaccgcg    1440
ctgctggaag ccgacggcgg cacgctcagc tatgccgagc tggacgccaa ggtccaggcc    1500
gtggccgacg ccctgcgcgc agcgggtgtg aggaccgacg agcgggtagc gctactggtc    1560
gcccgcggtc cccacctgct gccggcgatc cttggcgtgc agcgcgccgg cggcgcctat    1620
gtgccgatca atcccgacca tcccctggag gcgtccgcc tgctgttgga agactgcggt    1680
gcccgcgtgg tgctggtgga cgagcgcgca gcgacactcg gcgagagcct cggcgagacg    1740
cgcgtgctgc acctcgaacg cctgccgcag agcaccggcg acctgccggc ggccaacgtg    1800
gcgcccggcg acctggccta tgtcatctat acctccggtt cgaccggcat gcccaagggc    1860
gtcatggtcg agcaccgctc ggtggtcaac cgcctgaact ggatgcagcg tcgttatccg    1920
atcggcgaac gcgacgtgct tctgcaaaag actccggtga cgttcgacgt gtccgtctgg    1980
gaactgttct ggtggagttt caccggcgcc cgcctgtcgc tgttgccgcc cggcgccgag    2040
aaggacccgc gggaaatgct gcggagcatc cagcgcgacg cggtcacggt catccacttc    2100
gtgccgtcga tgctgacgcc gttcctcgac ctgctcgacg gcgacccgac cgcccgcgcg    2160
gcggcaagct cgctgcgcct ggtgttctgc agcggcgaag ccctcgcgcc gttgcaggtc    2220
gcgcgcttcc gccggctgtt cggcgacgcc gtgcgactgg tcaacctgta cggaccgacc    2280
gaggccaccg tcgacgtgtc cgaccatgaa tgcgccagcg acaaccccac gcgggtcccg    2340
atcggccggc cgatcgacaa cctgcgcctg tacgtcctcg accgcgcgct caggccgcag    2400
cccctcggtg ccgtcggcga gctatatata ggaggcgtcg gcgtcgcccg cggctacctg    2460
aaccggccgg agctgaacgc cgagcgcttc ctcgtcgacc ccttcgtcgc cggcggccgt    2520
ctctaccgta ccggcgacct ggcccgctgg ctggccgacg gcaacctcga atacctcggc    2580
cgcgccgacg accaggtgaa gatccgcggc aaccgggtcg aacccgacga agtacgcgac    2640
cgcctcgccg cgcttcccgg cgtacgcgac gccgcggtcg tggcacgcga ttcggcggta    2700
cgcggcacgc acctggtcgg ctactacgtg gctgcggcgg aactcgaccc cggtcaattg    2760
cgcgccggac tttcggcgac gctgccggac ttcatgctgc cagccttctt cgtgcgcatc    2820
gacagcctcc cgctcagcgc caacggcaag ctcgaccgcc ggcaactgcc ggcaccgccg    2880
gaacaggtgg cggcggttgc gccgcgcacg gcgaccgagg ccgaactggc ggcggtgtgg    2940
gccgatgtcc tcggcgtggc ggaggtcggc gtgcacgacg acttctacgc cctcggcggc    3000
gactcgatcc tgatgctgcg catccgcgcc gccgcacagc ggcgcggcct gggcttcgaa    3060
ctcgccgacc tgatgcgcaa cccgacggtg gcgggcctcg ccgagcgcct ggtgcgtccg    3120
ctcgcggagc gaagctacca gcccttcgaa ctggtttccg aagtcgacaa gccgcgcctg    3180
gaagggctgg aggacgcctt cccgaccagc cggctgagtc tcggcctgct cttccatagc    3240
cgccagcgcc ccgactcgtc ggtctaccac gacgtgttcc actaccgctt cgacctggcc    3300
tgggacgaag ccgcgttccg ccacgcgctg gaccgggtgg tcgccgccta tcccgcgctg    3360
cgttcgtcgt tcgacctcag cggtgcatcc gaaccgctgc aactggtgca tacccaggcg    3420
cgcagcgaac cgctgatcct ggacctgcgc ggcaacccgg aggccgggac ggtgctcgac    3480
gagcacatcc gccaacgccg cttccatcgc tattgctgc aacagcccgg gctattcctg    3540
ttcgccgcgt tcgtccgcga ggacggcctg gacctggtat tcagcttcca ccatgcgatc    3600
```

```
ctcgacggct ggagcgtggc caacctgatc gtcgcgctgg tcgccgccta ccgtggcgag   3660
ccgctgccgg gccccgcgcc ggcgctggcc tgccatgtcc gcgaggagct ggccgcgctg   3720
gcttcgccgg ccgccgtggg gtactggacc gggctgctgg agggcgcgag gatgacccgc   3780
ctcgacggct tcggcgccca cgagccgcaa gccgcgcaag gtccgccagc catcgcgaa    3840 gcgctgccgg acgggctgct cgaacgactc aaggccactg cggcgcaacg cggactgccg   3900
ttgaagtcgc tgctgctcgc cgcccattgc ctgaccctga tctgttctc ccgcagcgac    3960 agcgtggtca ccggcgcgat cagcaacggc cgccccgaac tgcccgacgc cgaccgcatg   4020
gtcggcctgt tcctgaatac cgtgccggtc cgctcggaga ttgccgggtg tagctggatc   4080
gaggtagccg atgcgctgtt ccgccaggag cgcgacggac acgcccaccg ccgctatccg   4140
ctcagcgcca tccagcagat cgtcggcgac gaactgagca cgccttcaa ctacgtcaac    4200 ctgcatgtcc tcgaaccgct gtggcaattg cgcgacttcc gcgtctggga agaaaccaac   4260
ttcgccctgc tggtcaacgt gatcgccacg cccagcgacg gcatgtacct gcgcatcgac   4320
agcgacggcc gcggcatcag ccgcagccag gccgcgctga tcggcgcgac cttcgtcgag   4380
ctcctgtggc gcctcgccga tcatcccgac gaagccgccg acttcgcctt cctcgccct    4440 cgccgcgacg ccgcttccca gcccgagccg ctggtcgacg tcgtcagcct gttcgaacgc   4500
caggtcgagg cgctgccggg cagcgccgcg ctggccttcg aggagcaacg ctggacctat   4560
cgcgacctcg accatgtggc gcgctgcgtg gccacccgcc tggtccgcgc cggcgcgcgc   4620
cgcggcgatg cgatcggagt ggcgctgaac cgttcgccgg agatgatcgc gacgatctgg   4680
ggcatcctgc gcgccggcct ggtctgcgtg ccgctggacg tcagctatcc cgcgcagcgc   4740
ctggcgctga tcctggagac cgcacagccg ttccgggtgg tcgcgcatcc cgagcacgcc   4800
catgtcgccg cggcggaacg ggtgctgccg gtagaggaac tggtcgccga catcgagccc   4860
gagaccttcg ccgcgccgca gctcgacgag ctggccatgc tgctgttcac ctctggttcc   4920
accgggcggc cgaagggcgt cgagcttagc caccggatgt gggccaacta cacccagtgg   4980
caattgcgcg tcgccagcgg cgtaccgggg ctgcgcacac tgcagttcgc gccgctgagc   5040
ttcgacatgg ccttccagga gatcttctcc acgctgtgcg gcggcggcga gctgcaactc   5100
atctccaacc gcgagcggat ggaccccctcc gcgttgctgc atgtcctcga acgccgccag   5160
gtccagcgcg tgctgttgcc cttcgtcgcc ctgcaacgcc tcgccgaggc ctccaacgcg   5220 ctggcgtgc gccccggcgc cctgcgcgtg gtggtgtcct ccggcgagca gttgcgcatc    5280
accgaagacg tccgcgcgtt ctgcgcggcg atgcccgggc tgctgctgga gaaccagtac   5340
ggtcccaccg agacgcacca ggtcacctac cactcgctga cggcgatcc ggcgcactac    5400 ccggacctgc cgccgatcgg ccggccgctg acgggtcg aggtgcaggt gctcgacgcc     5460
gcgctgcgcc cggtaccggt cggcgttacc ggcgagctgt acttcggcgg cgactgcctc   5520
gcgcgcggct accaccgcgc ccccaaactc accgccgagc gcttcgtcga acatccctgg   5580
cgccccggcg ccaggctcta ccgcaccggc gacctcgggc gcatcctcgg caacggcgag   5640
atcgtctggg tcgccgcgc cgatacccag gtcaaggtcc gcggcttccg catcgagccg    5700
gccgaggtcg agctggcgat catgcgccag gccgagcgcc agccgggcct gcgcggcgcg   5760
gcggtggtgg ctcgcgagcg ccagggcaac gatgcattcc tcgctgcctt cctgctcggc   5820
gagcccgagg cggtggatct cgccgaactg aagcaggcac tgcgcagcga actgccggaa   5880
cacatggtgc cggcacactt cgcctgggtc gacggcttcg ccctcacccc cagcggcaag   5940
cgcgacgacg ccgccctgcg cgcactgccg ctggagcacg ggacgaacat cgagtacctg   6000
```

-continued

```
gccccgcgcg acgactacga gcgcaccctg gccggactcc tcggcgagtt gctggatcgt    6060
ccccgggtag gcatccgcga cagcttcttc gacctcggcg gcacctcgct cagcgcgatg    6120
cgcttcatgc tgctgatcga gaagcgctat ggcgtcgacc tgccgatggc cgcgctgatc    6180
gagacgccga ccgtggaggg cctggccgaa cgcctgcggg aacgctcggc ggtgcgcgcc    6240
ttcgacccgc tggtaccgat ccgtgccggc ggcagccgcc cgccgctgtt cctcgtccac    6300
ccgctcggcg gccacgtgct ctgctacctg ccgctggtcc gcgcactgcc gccggaccag    6360
ccggtatatg ccctgcaggc ggccggcacc ggccagggca gtacgccgct ggcggtcctc    6420
gaggacatcg ccgccagtta cctcgcggcc atccgccggg tgcagccgga aggcccctat    6480
tacctcggcg gctggtcgtt cggcggcttc gtcgcctacg agatggcccg gcaactgcgc    6540
gcgctcgacc cgcaggcggt cgcccaactg atcgtgctcg actccatcac cgtcgaccgc    6600
aaccacgccg gcagcgccag cgacgaagcc ctgctgctgt tcttctactg ggaactggtc    6660
tggttcgagc gcagcgacaa ggaggtcgag ccgctgcctg aaggcgcgag cctggagcag    6720
aaactcgacc acatcgtcga acgcgccatc gaggccggcg tacttcccgc cggcaccccg    6780
cgcgccaccg tgcagcggct ctacgagctg ttccgggcga gctggcaggc actcatcggc    6840
tatcgcccgg aagtcagcga ccaggacatg accctgctgc gcgcggacgg cccgctgccg    6900
ctggcgctga agccgatgca cgacgccgcc ggcacccact acggcgaccc gaagaacggc    6960
tggcagcact ggaccagtgg ccgcctcgat gtgatcgacg tccccggcga ccacctggtg    7020
ctgatgaaag aacccctatgt cgagacgtcg gcggcagaga tcgccgcgtt gctcgaaccc    7080
tccacctcca gcgaacggac ccgcccatga                                      7110
```

<210> SEQ ID NO 27
<211> LENGTH: 1404
<212> TYPE: DNA
<213> ORGANISM: Pseudomonas aeruginosa

<400> SEQUENCE: 27

```
atgaaaacgc ccgcctggac gcgccatgcc ctctgggtca tgccgctcgc cctggggctg      60
caatccgccg tggtcgcggg ggatgagcag ccaagcaaga cttccagcta ttcgccggtg    120
gtgatcaatg aggacttcgc caccatcatg aagcgcatga cggcgaacaa accgtcgatc    180
gaacaggccc acaagacgct tctcgagcag cgttacgatc tcagcgacag gccggccaag    240
ggcgccagca tgacgcgcgg caagccgctg caggagggga tccgggtgaa gctgccggcc    300
ggcaccagct gggaggaact ggccaggctg agccccgagg aaatccgcaa gcaggggctg    360
ttccccggtg gcttcctgcc gctgccgcac cccaaccatg ccgaaggcgg gatggtcttt    420
cccaagttcc tcatcgacga gatcaagcgc caggaaagcc gcgacctgac ccgtttcgac    480
ctcgactacg acctgccgga ccacttcctg ccggaattcc cggcaccgat gttccttacc    540
acccggcctg acctgggcga tgtgtccaag ggcaagctgg tgaccatcga caactatttc    600
gagttgttca cgggattcct caatcccaag cagctggaag gctgcgcct gctgctaacg    660 gcctttccgc agcagcagtt caacctcacc gacgatcgcc gtagcgagca tccgagccgc    720
ggcgtagcct gcttcgactg ccatgcgaac ggccacacca atgccgctac tcacctggcc    780
ggcgatgtgc gcccgcagcc gttccgccac cgcatcgaca caccgacgct gcgcggggtg    840
aacatccagc ggttgttcgg ctcgcagagg gcgctgaaga ccgtcgagga cttcaccgag    900
ttcgagcagc gcgccgccta cttcgacggt gatccggtaa tcgccaccaa gaagggggtg    960
```

-continued

```
aacgtgctcg agcgtggcag tcaagtgcat ttcatgggtg agttccaggc gctgctggac    1020
ttccccccgg caccgaagct ggatgtggag gggcggctca atccgggcaa ggccagcgag    1080
caggaattgc gtggcgaaaa gctgttctac ggcaaggcgg cctgcgccgg gtgccatgcg    1140
ccgccttact tcaccgacaa cctgatgcac aacctgaagg tggagcgctt ctacgatccg    1200
aaactggtca atggcgtgat ggcgtccgcc gacgggccga tcaagacctt cccgttgcgc    1260
gggatcaagg attcgccgcc gtacctgcac gacgaccgcc tgctgaccct ggaggacacc    1320
gtggagttct tcaacctggt actggagcgc aagctgtccg cggaagagaa gggcgacctg    1380
gtggcctacc tgcgtaccct gtga                                           1404

<210> SEQ ID NO 28
<211> LENGTH: 1386
<212> TYPE: DNA
<213> ORGANISM: Pseudomonas aeruginosa

<400> SEQUENCE: 28
atgctcacgg tgtgtgcgaa ccccaagggt atttcccgac cagctccccc gcggtcggga     60 ttttttttg cctgtcgctc agcgcttcgg gtcgaagggc gaatagcccc gccggcgcag    120
gctcgccagg ggcgcgaaca gcggctccgg cagatcggcc caatcgaacc aggcccagcc    180
gtcgcacttg tccggctcca tgaggcgcgc ctcggcatcc tccgcgcaac cggccaggat    240
gaacgcggtg aggtagtggc gcccctcgaa gacgtcattg ctgaacgggc cgtggcgcag    300
ttcgctcagc gccaggtcgg tctcttccag ggcttcgcgc agggcgcagt cctccaccgc    360
ctcgccgaac tcgagatggc cgccgggcgc cgaccagcag ccagcgccat gactgccctt    420
gcggcgcccc agcaacacct tgccgtcccg caagatcagg acgcccacgc ctacctgcgg    480
tgccggcatc gtcgtactcc tgcttcggga tcagagatgg agcgtaccgc tcatgtacaa    540
cgccgccttg ccggagatga ccacccgctc gccgcgcacg tcgcattcca ggcgcccctt    600
gcgcgccccg ccctgctcgg cgctcagccg ggtcttgccc aggcgctgcg cccagtacgg    660
cgccagggag gtatgcgcgg agccggtcac cgggtcttcg ttgacgccga cgttgggccc    720
gaaccagcgc gagacgaaat cgaagcgctg gctgcgcgcg gtcaccgcca ccccgcggca    780
cggcaagccc ttcagccggg cgaagtcagg cgccagggcg gcgatcgtct tttcgtcgtc    840
gaccaccacg aggtaatcgt cggtcttcag cacttccgcc tcggcaatac ccagcgcctc    900
cagcagtccg tccggtgtcg cgcaaggctc cggacgcttg gccgggaagt ccatcgccag    960
cgagtcgccc tcgcgccgca cgctcagctc accgctacgg gtagcgaaac gcagtaccgg   1020
ggaagcgtcg tcgagcttgt ggatcagtac ccaggccgtc gccagggtcg catgaccgca   1080
caggtccacc tcgacctgcg gcgtgaacca gcgcaatcga tagtcgccgt cgcggccgac   1140
gacaaaggcg gtttccgaaa gattgttctc ttccgcgatg gcctgcaggc gctcgtcgtc   1200
cagccaggca tcgaggggc agaccgccgc cggattgccc tggaagggac tgtcggcgaa   1260
tgcgtctacc tggaagatcg tcagttccat gttccggact cctgtatcga tgggctgcgc   1320 acctagcag ccggaccgag accaggacaa tgccgcgccc cgcgcaggcg cctcgctcag   1380
atctga                                                              1386

<210> SEQ ID NO 29
<211> LENGTH: 1104
<212> TYPE: DNA
<213> ORGANISM: Pseudomonas aeruginosa

<400> SEQUENCE: 29
```

```
atgaaaaaag tttgtgcact ggcgttatcg atcctgacga cgatcggtgc gacagcggcg      60
gacagtgcat gggctgcgca aaccagcgtc catctttaca actggtatga cttcatcgcc     120
ccggaaacgc ccaaggcttt ccagaaggaa accggcaccc gtgtcgtcct cgacaccttc     180
gacagcgccg agaccgcgca gggcaagctg atggtcggcc gctccggcta cgacgtggtg     240
gtgatcacct ccaacatcct gcccgggctg atcaaggcgg cgtcctcca ggaactcgac      300
cgcgaccggc tcccccactg gaagaacctc gacgcggaca tcctcgggaa gcttcaggcc     360
aacgatcccg gcaatcgcta tgccgtacct tatctctggg aaccaccgg atcgcctac       420
gatgtggaca aggtccgcaa gctgctcggc cccgacgcgc cggtcgactc ctgggacctg     480
gtcttcaagg aggagaacat ctcccgcctc agccagtgcg cgtggccac gctggactcc      540
tccaccgagc tggtgtccat cgccctcaac tacctgggcc tgccgcacaa cagccagaat     600
cccgaggact accagaaagc ccaggaactg ttgctgaagg ttcgcccta cattcgctat      660
ttcgactcct ccagagtcga caccgatctc tccaacggca acgtctgcgt ggtggtcggc     720
tggcagggca cggcctacat ggcccaggtc aacaacgaac aggccgggaa cggtcgccat     780
atcgcctaca gcattccccg ggaaggctcg ctggtctggg ccgagaacat ggtgctgctc     840
aaggatgcac cgcatccgca gcagggttat cgcgctgatcg actacctgct gcgtccggag   900
gtcatcgcca ggacctccaa ctacgtgggc tatccgaatg caaccaggc ggcgctgccg      960
ctggtagagc ggaaactgcg ggaaaacccg gcggtttacc tgagcaagga aaccatggcg    1020
accctcttcc cgctggaaac cctgccactg aaggtcgaga gaatccgtac ccgggtctgg    1080
agccgggtca agaccgggag ctga                                           1104
```

<210> SEQ ID NO 30
<211> LENGTH: 1251
<212> TYPE: DNA
<213> ORGANISM: Pseudomonas aeruginosa

<400> SEQUENCE: 30

```
gtgggctgtc cggggcggct aggatggaca ttttcatcgt ctcgggcagg cctgtcgcga      60
ccgcgcgaag tcgcgacgga tgccgctgct aaggagcaac ggatgaccgt tcttatccag     120
ggggccggga tcgccggcct ggcgctggcg cgcgaattca ccaaggcagg catcgactgg     180
ctgctggtcg agcgggccag cgagatcagg cccatcggta ccggcatcac cctggcgagc     240
aatgcgttga cggcgttgtc cagcaccctg gatctcgacc ggctgttccg ccgtggcatg     300
ccgttggccg gcatcaacgt atacgcccac gacggttcga tgctgatgtc gatgccttcc     360
agtctgggtg ggaattcccg cggcggcctg gcgttgcagc gccacgaact gcatgcggcg     420
ctactggagg ggctggatga gtcgcgcatt cgggtcgggg tctccatcgt gcagatcctc     480
gacggactcg accacgaacg cgtgaccctg agcgacggca ctgtccacga ctgttcgctg     540
gtggtcggtg cggatggcat tcgttcgagc gtgcgacgtt atgtctggcc ggaggcgacc     600
ttgcgtcatt ccggcgaaac ctgctggcgc ctggtcgttc cccatcggct ggaggacgcc     660
gagctggcgg gagaggtctg ggggcacggc aagcgcctcg gcttcatcca gatcagcccg    720
cgcgagatgt atgtctacgc gaccctgaag gtgcgccggg aggagcccga ggacgaggag    780
ggcttcgtaa ccccgcaacg gctggccgcc cactacgcgg acttcgacgg catcggcgcg    840
agcatcgccc ggctcatacc gagcgccacc acgctggtgc acaacgacct cgaggagttg    900
gccggcgcct cctggtgccg cggacgggta gtgctgatcg gtgacgccgc acacgccatg    960
```

-continued

| | |
|---|---|
| acgccgaacc tggggcaggg cgcggccatg gccctggagg acgccttcct gctggcgcgc | 1020 |
| ctgtggtgcc tggcgccgcg cgccgagacg ctgatcctgt ccagcagca acgcgaggcg | 1080 |
| cggatcgagt tcatcaggaa gcaatcctgg atcgtcggcc gccttggtca gtgggaatcg | 1140 |
| ccctggagcg tctggctgag gaataccctc gttcgcctgg tgccgaatgc cagtcgcagg | 1200 |
| cgcctccacc agcgtctttt caccggtgtc ggtgagatgg ccgcacagta g | 1251 |

<210> SEQ ID NO 31
<211> LENGTH: 1754
<212> TYPE: DNA
<213> ORGANISM: Pseudomonas aeruginosa

<400> SEQUENCE: 31

| | |
|---|---|
| atgatggacg ccttcgaact tcccaccacc ctggtccagg ccctgcgtcg ccgcgctgtc | 60 |
| caggagcccg agcgcctggc gctgcgcttc ctcgccgagg acgatggcga aggcgtggtc | 120 |
| ctcagctatc gcgatctcga cctgcgcgcg cggagcatcg ccgcggccct gcaggcccat | 180 |
| gcgcagctgg gcgatcgcgc ggtactgctg tttcccagcg gccccgacta cgtcgcggcg | 240 |
| ttcttcggtt gcctgtatgc cggggtcatc gcggtgccgg cctacccgcc ggaatcggcg | 300 |
| cgccgccatc accaggaacg cctgttgtcg atcatcgccg acgccgagcc gcgcctggtc | 360 |
| ctgaccaccg ctgacctgcg cgagccattg ctgcagatga acgcgcaact gtccgccgcc | 420 |
| aacgccccgc aactgctctg cgtcgaccag ttggacccgg ccgttgccga ggcctgggac | 480 |
| gagccgcaag tgcgtcccga gcacatcgcc ttcctccagt acacctccgg ttcaaccgca | 540 |
| ttgcccaagg gcgtgcaggt cagccatggc aacctggtcg ccaacgaggt gctgatccgc | 600 |
| cgaggcttcg gcatcggtgc cgacgacgtg atcgtcagct ggctgccgct gtaccacgac | 660 |
| atgggcctga tcggcggcct gctgcaaccg atcttcagcg gcgtaccctg cgtgctgatg | 720 |
| tcgccgcgct acttcctcga acgtccggtg cgctggctgg aagccatcag ccagtacggc | 780 |
| ggcaccgtca gcggcggtcc cgatttcgcc taccggctgt gcagcgagcg ggtcgccgag | 840 |
| tcggccctgc agcgtctcga cctgagcggt tggcgggtag ccttctccgg ttccgagccg | 900 |
| atccgccagg acagcctgga acgcttcgcc gagaaattcg ccgccagccg cttcgacgcg | 960 |
| tccagtttct tcgcctgcta cggcctcgcc gaggcgaccc tgttcgtcac cggcggccag | 1020 |
| cgcggccagg gcattcccgc cctggcggtg gatggcgagg cgctggcgcg caaccgcatc | 1080 |
| gccgaaggcg aaggcagcgt gctgatgtgc tgcggccgca gccagccgga acacgccgtg | 1140 |
| ctgatcgtcg acgcggcgag cggcgaggtc ctcggcgacg acaacgtcgg cgagatctgg | 1200 |
| gccgccgggc cgagcatcgc ccacggctac tggcgcaacc cggaagcttc ggcgaaggcc | 1260 |
| ttcgtcgagc gtgacgggcg cacctggctg cgcaccggca acctcggctt cctccgcgac | 1320 |
| ggcgaactgt tcgtcaccgg gcgcctgaag gacatgctca tcgtccgcgg ccacaacctc | 1380 |
| tatccgcagg acatcgaacg caccgtcgag agcgaggtgc gtcggcgcg caagggcagg | 1440 |
| gtcgcggcct tcgcggtcac ggtcgatggc gaggaaggca tcggcatcgc gccgagatc | 1500 |
| ggtcgcggcg tccagaaatc ggtgccggcc caggagctga tcgactcgat ccgcaggcg | 1560 |
| gtggccgagg cctaccagga agcgccgaag gtggtggcgc tgctcaatcc cggcgccttg | 1620 |
| ccgaagacgt ccagcggcaa gctgcaacgt tccgcctgcc gcctgcgcct ggaagacggc | 1680 |
| agcctggaca gctatgcgct gtttcccggc ctccaggccg tgcaggaggc gcagccgccg | 1740 |
| gcaggcgacg acga | 1754 |

<210> SEQ ID NO 32
<211> LENGTH: 7335
<212> TYPE: DNA
<213> ORGANISM: Pseudomonas aeruginosa

<400> SEQUENCE: 32

| | | | | | |
|---|---|---|---|---|---|
| gtgttggtca | tcacccagca | ccatatcgtg | tccgacggtt | ggtcgatgca | ggtgatggtc | 60 |
| gacgaactgc | tccaggccta | tgccgcggcg | cgccgcggcg | aacaaccgac | gctggcgcca | 120 |
| ttgacgctgc | agtacgccga | ctatgctgcc | tggcatcgcg | cctggctgga | cagcggcgag | 180 |
| ggcgcgcgga | agctggatta | ctggcgtgag | cgcctgggcg | ccgagcagcc | ggtcctggaa | 240 |
| ctgcccgccg | accgggtgcg | cccggcccag | gccagcggac | gcgggcagcg | tctggacatg | 300 |
| gcgctgccgg | tgtcattatc | ggaggagctg | ctggcctgcg | cccggcggga | gggtgtcacc | 360 |
| ccgttcatgc | ttctattggc | ctcgttccag | gtgctgttga | agcgctatag | cgggcagtcg | 420 |
| gacattcgcg | tcggggtacc | tatcgccaac | cgcaaccgcg | ccgaggtcga | gcgcctgatc | 480 |
| ggcttcttcg | tcaataccca | ggtgctgcgt | tgccaggtcg | atgctggcct | ggctttccgc | 540 |
| gatctactgg | gccgcgtgcg | cgaggcggcg | ctgggcgcgc | aggcgcacca | ggatctgccg | 600 |
| ttcgagcaat | tggtcgatgc | cttgcagccc | gaacgcaatc | tcagccacag | cccgttgttc | 660 |
| caggtgatgt | ataaccacca | gagcggcgag | cggcaggatg | cccaagtcga | tggtttgcac | 720 |
| atcgagagtt | ttgcctggga | tggtgctgcc | gcacagttcg | atcttgccct | cgatacctgg | 780 |
| gaaaccccgg | acggccttgg | ggcggcgctg | acctacgcga | ccgacctgtt | cgaggcgcgg | 840 |
| accgtcgagc | gcatggcgcg | gcattggcag | aacctgctgc | gcggcatgct | ggaaaacccg | 900 |
| caggccagcg | tcgactcgct | gccgatgctc | gatgccgagg | agcgtggcca | gttgctggaa | 960 |
| ggctggaacg | ccactgccgc | cgagtacccg | ctgcaacgcg | cgtgcaccg | gttgttcgag | 1020 |
| gagcaggtcg | agcgcacgcc | gacggcgccg | gcgctggcct | tcggcgagga | acgcctggac | 1080 |
| tacgccgagc | tgaaccgccg | ggccaaccgc | ctggcgcatg | ccctgatcga | gcgcggggtc | 1140 |
| ggtgcggacc | gcctggtggg | cgtggccatg | gagcgttcca | tcgagatggt | cgtggccctg | 1200 |
| atggcgatcc | tcaaggccgg | cggcgcctac | gtgccggtgg | acccggagta | ccccgaggag | 1260 |
| cgccaggcct | acatgctgga | ggacagcggc | gtgcagctgc | tgctcagcca | gtcgcacctg | 1320 |
| aagctgccgc | tggcgcaagg | cgtgcagcgg | atcgacctgg | accaggccga | tgcctggctg | 1380 |
| gaaaaccatg | ccgagaacaa | tccggggatc | gagctgaacg | gcgagaatct | tgcctatgtc | 1440 |
| atctacacct | ccggctccac | cggcaagccc | aagggtgccg | gcaaccgcca | ttcggcgctg | 1500 |
| agcaaccgct | tgtgctggat | gcagcaggcc | tacggcctgg | gcgtcggcga | cacggtgttg | 1560 |
| cagaagaccc | cgttcagctt | cgacgtgtcg | gtctgggagt | tcttctggcc | gctgatgagt | 1620 |
| ggggcacgtt | tggtggtggc | cgcgccgggt | gaccatcgcg | acccggcgaa | gctggtggcg | 1680 |
| ctgatcaacc | gcgaaggggt | cgacacgctg | cacttcgtgc | cgtcgatgct | gcaggccttc | 1740 |
| ctgcaggacg | aagacgtcgt | ctcctgcacc | agcctgaaac | gcatcgtttg | cagcggcgag | 1800 |
| gcgctgtcgg | cggacgccca | gcagcaggtg | ttcgccaagc | tgccgcaggc | cggcctctat | 1860 |
| aacctctatg | gcccgaccga | gcggccatc | gacgtcaccc | actggagctg | cgtggaggag | 1920 |
| ggcaaggacg | cggtgccgat | cggcggccg | atcgccaacc | tgggctgcta | catcctcgat | 1980 |
| ggcgacctgg | agccggtgcc | ggtgggcgtg | ctcggcgagc | tgtacctggc | cggtcggggc | 2040 |
| ctggctcgtg | gctaccacca | gcgtccgggg | ctgactgccg | agcgtttcgt | cgccagcccg | 2100 |
| ttcgtggctg | gggagcggat | gtaccgcacc | ggcgacctgg | cgcgctaccg | cgccgatggg | 2160 |

```
gtgatcgagt acgccgggcg gatcgaccac caggtgaagc tgcgcggcct gcgcatcgag   2220
ctgggcgaga tcgaggcgcg cctgctggag catccgtggg tgcgcgaggc ggcggtgctg   2280
gcggtggaca gcaggcagtt ggtcggctac gtggtgctgg agagcgaggg cggcgactgg   2340
cgcgaagcgc tggccgcgca cctggcgaca agcctgccgg aatacatggt gccggcgcag   2400
tggctggcgc tggagcggat gccgctgagt ccgaacggca agctggatcg caaggcgctg   2460
ccgcgaccgc aagctgctgc ggggcagacg catgttgcgc cgcagaatga aatggagcga   2520
cgtatcgcgg ccgtctgggc ggacgtgctg aagctggagg aggtgggcgc caccgacaac   2580
ttctttgccc tgggtggcga ttccatcgtt tcgatccagg tggtgagtcg atgccgtgcg   2640
gcgggcatcc agttcactcc gaaggacctg ttccaacaac agaccgtaca ggggctggcg   2700
cgagtcgccc gcgtagggc tgcggtgcaa atggagcagg gcctgtgag cggcgagacg   2760 gtgttgttgc cgttccagcg gttgttcttc gaacagccga ttcccaatcg ccagcactgg   2820
aaccagtcat tgctgttgaa gccgcgcgag gccctgaatg cgaaggcact cgaagcggcc   2880
ttgcaggccc tggttgaaca tcacgacgca ttgcgtctgc gcttccatga acggacgga   2940 acctggcatg ccgaacatgc cgaagcaacg ctgggcggtg cgctgctctg gcgtgccgag   3000
gcggtggacc gacaagcgct ggagtcgctc tgcgaggagt cgcagcgcag cctggacctg   3060
gccgacggcc cactgttgcg gagcctgttg gtggatatgg ccgacggcgg ccagcgtctg   3120
ttgttggtga tccaccatct ggtggtggac ggggtgtcct ggcgcattct gctggaggat   3180
ttgcaaaggg cttaccagca gagcctccgt ggagaagctc cgcggctgcc tggcaagacc   3240
agcccgttca aggcctgggc cggccgagtg agcgagcatg cccgtggtga gtcgatgaag   3300
gcgcaattgc agttttggcg cgagctgctg aaggtgcgc cggccgagct tccgtgcgag   3360
catccgcaag gcgctctgga gcagcgtttc gctacctccg tgcagagtcg cttcgaccgc   3420
agcttgaccg aacgcttgct gaagcaggcg ccggcagcct accggaccca ggtcaacgat   3480
cttctgctga ccgccctggc gcgagtggtc tgccgttgga gcggcgcctc ttcaagcctg   3540
gtacagctgg aagggcatgg gcgcgaggag ctgttcgccg atatcgacct gagtcgcacc   3600
gtgggttggt tcaccagttt gttcccggtg cgcctgagcc cggtcgcgga tcttggcgag   3660
tccctgaagg cgatcaagga acagttgcgt gcgattcccg acaagggcct gggttatggc   3720
ttgctgcgct atctggctgg agaggaaagt gcccgggtcc tggcggggtt gccgcaggcg   3780
cggatcactt tcaattacct gggccagttc gacgctcagt tcgacgagat ggctctgctg   3840
gacccggctg gcgaaagcgc gggggcagag atggaccccg gcgctccgct ggacaactgg   3900
ctgagtctca atggccgggt gttcgacggt gaactgagta tcgactggag cttcagctcg   3960
cagatgttcg gcgaggacca ggtgcgtcgc ctggccgatg actatgtggc tgagctgacg   4020
gcgctggtcg acttctgctg cgattcgcca cggcatggcg cgacgccttc cgatttcccg   4080
ctggcggggt tggaccaggc gcgtctggat gccctgccgg tcgcgctgga agaggtcgag   4140
gacatctatc cgctgtcacc catgcagcag ggcatgctgt tccattcgct gtacgagcag   4200
gcatcgagcg actacatcaa tcagatgcgt gtggatgtgt ccggcctcga tctcccgcgc   4260
ttccgcgcag cctggcagtc cgccctggac cggcacgcga tcctgcgcag tggtttcgcc   4320
tggcaggggg agctgcagca gcccttgcag atcgtctatc gacagcgcca gttgcccttc   4380
gccgaagagg acctgagcca ggcggcgaat cgggacgccg cgctgctcgc gctggctgcg   4440
gccgagcgca aacgcggttt cgaactgcag cgtgcgccac tgttgcggct gctgttggtg   4500
aagactgccg aaggtgagca tcacctgatc tacacccatc atcacatcct gctggacgga   4560
```

```
tggagcaatg cccagttgct cagcgaggtg ctggagtcct atgccggacg ctcgccggag    4620
cagctccggg atggccgcta tagcgactac atcgcctggt tgcagcggca ggacgcggca    4680
gctaccgagg cattctggcg cgagcagatg gcggctctgg acgagccgac gcgattggtc    4740
gaggcactgg ctcagccggg actgacatcg gccaacggcg tcggagagca cctgcgtgag    4800
gtggacgcaa cggctaccgc gcggctccgg gatttcgccc ggcgccacca ggtcactctc    4860
aataccctgg tccaggcggg ctgggcgctg ctcctgcaac gctataccgg acaacacacc    4920
gtggtcttcg gcgccaccgt ctccgggcgc cctgccgatc tgccgggtgt cgagaaccag    4980
gtcgggttgt tcatcaatac cttgccggtg gtggtaacgc tggctccaca gatgaccctc    5040
gacgaactgc tgcaagggct gcaacggcag aacctggcgt tgcgcgaaca ggagcacacg    5100
cctctgttcg agctgcagcg ctgggcgggg ttcggcggcg aggcggtttt cgacaacctg    5160
ttggtgttcg aaaactaccc ggtggacgag gtgctcgaac ggtcctccgc tggaggcgtg    5220
cgtttcggtg ccgtagcgat gcacgagcag accaactatc cgctggccct ggcgctgggt    5280
ggcggggata gcttgtcact gcaattcagc tacgatcgcg gactgttccc ggccgctacg    5340
atcgagcgcc tgggtcgcca cctgacgact ctgctggagg cattcgccga acatccgcag    5400
cgacgtctgg tcgatctgca gatgctcgag aaggcggagc ttagcgctat cggcgctatc    5460
tggaaccgca gcgattcggg ctatccggca acgccgctgg tacaccagcg agtggccgag    5520
cgggcgcgta tggcgccgga tgcggtggcg gtgatcttcg acgaggaaaa gctcacctac    5580
gccgagctgg atagccgggc caaccgcctg gcacatgcgt tgatcgcccg aggcgtcggc    5640
cccgaagtgc gtgtggcgat cgccatgcag cgcagcgcgg agatcatggt ggcgttcctg    5700
gcggtactga aggccggcgg cgcctacgtg ccgctggaca tcgaatacccc gcgcgagcgc    5760 ctgctgtaca tgatgcagga cagtcgcgcg cacctgctgc tgacccatag ccacctgctg    5820
gagcgtctgc cgatccccga ggggttgtcc tgcctgtccg tggatcgcga ggaggagtgg    5880
gccggcttcc ccgcccatga tccagaggtg gcgctgcacg gcgacaacct ggcctatgtg    5940
atctacacct ccggctccac cggcatgccc aagggcgtgg cggtgtccca cggtccgttg    6000
atcgcccata tcgtggctac cggcgagcgc tacgagatga ccccggagga ctgcgagctg    6060
cacttcatgt cgttcgcctt cgacggttcc cacgaaggct ggatgcaccc gttgatcaac    6120
ggcgcgcggg tgctgatccg cgacgacagc ctgtggctgc cggaacggac ctacgccgag    6180
atgcatcgcc acgggtaac ggtgggggtg ttcccgccgg tgtacctgca gcaactggcc    6240
gagcatgccg agcgcgacgg caatccgccg ccggtacggg tctattgctt cggcggcgac    6300
gcggtggcgc aggccagcta tgacctggcg tggcgggcgc tgaagccgaa gtacctgttc    6360
aacggctacg gcccgaccga cggtggtg acgccgctgc tgtggaaagc acgggcgggc    6420
gatgcctgcg cgcggccta catgccgatc ggtacgctgc tgggcaaccg tagcggctac    6480
atcctcgacg ggcagttgaa cctgctgccg gtaggcgtgg cgggcgaact gtacctgggc    6540
ggggaagggg tggcgcgcgg ctacctggag cgtccggcgc tgaccgccga gcgtttcgtg    6600
ccggatccct ttggcgcgcc gggcagccgg ctgtaccgca gcggcgacct gacccgtggg    6660
cgtgcggatg gggtggtgga ctacctcgga cgggtggacc accaggtgaa gatccgaggc    6720
ttccgcatcg aactgggaga gatcgaggcg cgcctgcgcg agcatccgtc ggtgcgcgag    6780
gcggtggtgg tgcccagcc gggcgcggtg gccagcagt tggtgggcta cgtggtggcg    6840
caggcgccag cggtcgcgga ttcgccggaa gcgcaggcgg agtgccgggc gcagttgaag    6900
```

-continued

```
acggcgctgc gcgagcgcct gccggaatac atggtgccgt cgcacctgtt gttcctggcg      6960
cggatgccgc tgacgccgaa cggcaagctg accgcaagg gcctgccaca gccggatgcg       7020
agcctgttgc agcaggtcta cgtggcgccg cgaagcgatc tggagcaaca ggtcgcgggg      7080
atctgggcgg aggtcctgca attgcaacag gtcgggctcg acgacaactt cttcgagctt     7140
ggcggccact cgttgctggc gatccaggta actgcccgga tgcagagcga ggtcggcgtg     7200
gagctgccgc tggcggcgct gttccagacc gagtcgctga agcctatgc cgagcttgcc     7260 gcggcgcaga cttccagcaa tgacaccgat ttcgatgacc ttcgtgaatt catgagcgaa    7320
ctagaggcga tctga                                                      7335

<210> SEQ ID NO 33
<211> LENGTH: 2556
<212> TYPE: DNA
<213> ORGANISM: Pseudomonas aeruginosa

<400> SEQUENCE: 33
atgctttcca atccaaacct ggacctcgtg tcccgcttcg ttcgcctgcc tctggcgcag        60
cagaaattgt tctatcagcg tgtccaggcc aagggcatga gcttcgcccg cctgccgatc       120
ccgcagactc gccaggagat ggacaacctg ccgctgtcct atgcccaaga gcggcagtgg       180
ttcctctggc agctggagcc ggagagttcc gcctaccaca ttcctaccgc cctgcgcctg       240
cgcggcaggt tggacattgc gtccttgcag cgcagcttcg cggcgctcgt cgagcggcac       300
gaaagcctgc gcacgcggat cgcgcggatg ggtgatgaat gggtgcaggt cgtctccgcc       360
gacgtctcgc tggcgctcga agtcgaagtg caacgggac tcgacgaaca gcgattgctg        420
gagcgggtcg aggcggagat cgcacgaccc ttcgatctcg aacagggacc gttactgcgg       480
gtgactttgc tggaggtgga cgccgacgag catgtgctgg tcatggtcca gcaccatatc       540
gtctccgacg gttggtcgat gcaattgatg gtcgaggaac tggtccagct ctatgccgcc      600
tatagccaag ggctcgacgt ggtgttgccg gccctgccga tccagtacgc ggactacgcc      660
ctgtggcagc gcagctggat ggaggcgggg gaaaaggagc gccagttggc gtactggacc      720
ggcctgctgg gcggcgagca gccggtgatc gagttgcccc tcgatcaccc gcggcagccg      780
ctgcgcagct atcgtggagc gcaattggac ctggagctgg agccacacct ggcccttgcc      840
ttgaaacagc tggttcagcg caagggtgtg accatgttca tgctgttgct ggcttccttc      900
caggcgctgt tgcatcgcta tagcggacag gcggatatcc gtgtcggcgt gcctatcgcc      960
aaccgtaacc gggttgaaac cgagcggctg atcggtttct tcgtcaacac ccaggtgctc     1020
aaggccgaca tcaatggccg gatgggtttc gacgagttgc tggcccaggc cgccagcgc      1080 gcgctggagg cacaggctca ccaggacctg ccgttcgagc aactggtgga ggcttttgcag    1140 ccggaacgca gcctcggcca caaccgttg ttccaggtca tgttcaatca ccaggccgac      1200
tctcgttcgg ccaaccaggg cgtgcaactg ccaggcctgt cgctggagcg gatggagtgg    1260
cggagcagct ccgtggcctt cgacctgacg ctggacgtgc acgaggccga ggacggtatc    1320
tgggcatcgt tcggctatgc cacggatctg ttcgaggcct cgaccgtcga gcgcctggct    1380
cggcactggc agaatctcct gcgcggcatc gtggccgaac cgggccggcc ggtcgccgag    1440
ttgccgctgt tgctggacga ggagcgcgat tgcctgtcgc gggcctgggc agagaacgcc    1500
gacgagggtg ggttgccgcc cctggtccag ttgcagatcc aggagcaggc ccgtctgcgt    1560
ccgcaggcgc aagcactggc gctggagggg caggccttga gctacgccga gctcaacgcc    1620
cgcgccaatc gtctggctca ctgcctgata gcgcgtggcg tcggtcccga tgtgctggtg    1680
```

-continued

```
ggaatcgccg tcgagcgctc gctggacatg gtggtcggtc tgctggcgat cctcaaggcc    1740
ggtggtgcct atgtgccgct ggacccgacc tatccgcagg accgtttgcg tcacatgctc    1800
gaggacagcg ccgtcggcct gttgctcagc caggagcatt tgctgcccgg gctgcctttg    1860
cacgaagggc tggaggtgct ctccatcgac cgcctggaac gggacgcatc ggtgtctacg    1920
gatgatccgg tggtgaacct gcggccggag aacctggcct atgtgatcta cacctccggc    1980
tccaccggaa aacccaaggg cgtggccatc agccatgcgg cgcttgcgca gttctcgcgt    2040
atcgccagtg gttattccgc gctcaccccg gaggatcgga tattgcagtt cgccaccctg    2100
agcttcgacg gcttcgtcga acagctctat ccggcgctga cccgtggtgc ctgcgtggtc    2160
ctgcgtggcg cgacctctg ggataccggt gagctgtatc ggcagatagt cgagcagggc    2220 gtgaccettg ccgacctgcc cacggcgtac tggaacctgt cctgctcga tgccctggcc    2280 gagccacggc gttcctacgg tgccttgcgg cagatccaca tcggtggcga agccatgcca    2340
ctggaggggc cgaagctctg gcggcaagcc ggcatgggcc gggtgaggtt gctcaatacc    2400
tatggaccga ccgaggccac ggtggtgtcc agcgtcttcg attgttccgc cgagaacgcc    2460
cgggtgggca atgccagtcc tatcggccag gcgctacccg gccgtacgtt gctggtgctg    2520
gatgaacatc tcggcctact gcccgtaggg cggtag                              2556
```

<210> SEQ ID NO 34
<211> LENGTH: 2334
<212> TYPE: DNA
<213> ORGANISM: Pseudomonas aeruginosa

<400> SEQUENCE: 34

```
atgtcccggc cgttccggcc accactttgc agagaaacga catcgatggg gatgcgtacc      60
gtactgaccg gcctggccgg catgctgttg ggttcgatga tgccggtcca ggccgatatg     120
ccgcggccga ccgggctggc cgcggatatc cgctggaccg cctatggcgt gccgcacatc     180
cgggccaagg atgagcgcgg cctgggctat ggcatcggct acgcctacgc gcgcgacaac     240
gcctgcctgc tggccgagga gatcgtcacc gcgcgcggcg agcgggcgcg ctatttcggc     300
agcgagggca agtcgtcggc cgagctggac aacctgccgt ccgacatctt ctacgcctgg     360
ctcaaccaac ccgaggcgct gcaagccttc tggcaggcgc agacgcccgc ggtacgccag     420
ttgctcgaag gctacgccgc cggtttcaac cgcttcctcc gcgaggccga cggcaagacc     480
accagttgcc ttggccagcc ctggctgcgg ccatcgcga ccgatgacct gctgcgcctg     540
acccggcgcc tgctggtcga aggcggggtc ggccagttcg ccgacgcgct ggtggccgcc     600
gcgccgcccg gagcggagaa ggtcgccttg agcggcgagc aggcgttcca ggtcgccgag     660
cagcggcgcc agcgcttccg cctggagcgc ggcagcaacg ccattgccgt tggcagcgaa     720
cgttcggcgg acggcaaggg catgctcctg gccaacccgc acttccctg aacggcgcg      780 atgcgtttct accagatgca cctgaccatt cccggccggc tcgacgtgat ggggcctcg     840 ctgcccggcc tgccggtggt caacatcggc ttcagccgcc acctggcctg acccacacg     900 gtggatacct ccagccactt caccctgtat cgcctggcgc tggacccgaa ggaccgcgg     960 cgctacctgg tcgacggtcg ttcgctgccg ctggaggaga agtccgtcgc gatcgaggtg    1020
cgcggcgccg acggcaagct gtcgcgcgtc gagcacaagg tctaccagtc gatctacggc    1080
ccgctggtgg tctggcccgg caagctggac tggaaccgca gcgaggccta tgcgctgcgt    1140
gacgccaacc tggagaacac ccgggtactg caacagtggt actcgatcaa ccaggccagc    1200
```

-continued

```
gacgtcgccg acctgcgccg gcgcgtcgag gcgctacagg ggatcccctg ggtcaacacc   1260
ctggccgcgg acgagcaggg caacgccctg tacatgaacc agtcggtggt gccctacctg   1320
aagccggaac tgattcccgc ctgcgccatt ccgcaactgg tcgccgaagg cctgccggcc   1380
ctccaggggc aggacagccg ctgtgcctgg agtcgcgacc cggccgcggc ccaggctggc   1440
atcaccccgg cggcgcaact gccggtgctg ttgcgcaggg acttcgtgca gaactccaac   1500
gacagcgcct ggctgaccaa cccggcgagc ccgctgcagg gcttctcgcc cctggtcagc   1560
caggagaagc ccatcggtcc gcgggcgcgc tacgccctga ccggctacag ggcaagcag    1620 ccgctggagg cgaagacgct cgaggagatg gtcaccgcca accatgtctt cagcgccgac   1680
caggtgctgc cggacctgct ccgcctgtgc cgcgacaacc agggcgagaa gtcccttgcc   1740
cgcgcctgcg cggccctggc gcagtgggac cgtggcgcca acctcgacag cggcagcggc   1800
ttcgtctact ccagcgcctt catgcaacgc ttcgccgaac tcgacggcgc gtggaaggaa   1860
ccgttcgatg cgcaacgtcc cctggatacg ccgcaaggca tcgccctcga ccggccgcag   1920
gtggcgaccc aggtgcgcca ggcgctggcg gacgcggcgg cggaggtgga aagagcggg    1980 attcccgacg gcgcgcgctg gggcgacctg caagtgagca cccgtggcca ggaacgcatc   2040
gcgattcccg gcggcgatgg ccatttcggg gtctacaacg cgatccagag cgtccgcaag   2100
ggcgaccacc tggaggtggt cggcggcact agctacatcc agctggtgac cttccccgag   2160
gaagggccca aggctcgcgg gttgctggct ttctcccagt ccagcgatcc gcgctcgccg   2220
cactaccgcg accagaccga gctgttttcc cgccagcaat ggcagacctt gccgttcagc   2280
gacaggcaga tcgacgccga cccgcaactg caacggctaa gcattcgcga atga         2334
```

<210> SEQ ID NO 35
<211> LENGTH: 6390
<212> TYPE: DNA
<213> ORGANISM: Pseudomonas aeruginosa

<400> SEQUENCE: 35

```
gtgcgaggga tagccatgag tgcgtcagaa gacctgcaat ccgctgtgca accggccgcg     60
agcgaagcgc tcgaaggatt cccgctgtct cccttgcaga cccgcgcctg gcgccgccat    120
gccgagcggc cggaaaatac ggttgtcggc gtgcgcctgc acgccccggc cgatcccgtg    180
gcgacgctgg agcggctgcg ccgggcgctg acggcgaggc gcaactgcg cgtggcctac     240 cggacgatgc cggcatgag cctgccggtg caggtactgg atgggcgcgc ggccgatctg     300
ctggtcgagc gcctgccggg agacggcgac tgggccggac gcttcgcgcg cgaaagcgcg    360
cgtctcgccg cttcgcccct gggcggggaa ggccagccgg tactggcgct cggcctgctg    420
ctggacgccg ccggagagac gctccagggg ctgttgctgg cggcgccggc gttcgtcgtc    480
gatgcggcca gcctggtggc gctgctgcgc gcggcctggg gccggccgg ccaggcgagc     540 gcggacgagg gagacgaggc gctgctgttc cagcatttct ccgagtgggc caacgaggcg    600
ctggccggcg aagacggcga aagcgccagc ggttactggc gagagcaggc ggccgttgcg    660
gcggagagtc cgctggcgct ggcggacgac ctgggcgaag gcgagtggac ggcgcggcgc    720
ctgctgccgc gcgcgctgct cgaacgcctg gccgccaacg gcttgccgga ggcggccgcc    780
ctgctggcct ggacccaggt cgccgggcag ttccagggcg acgagggcct cccgctggaa    840
atggcgcgac tggtctcggg gcgcctgttc aacgagttcg ccgagctggc cggaccgttc    900
gccggggtcg cgccgctgtg cctggagaat gtccgcgcgg cagcgtcgg cgagcggctc     960 gacgccctcc aggcggcgat cctcgcccag gaggaggcag cggccctgcg cgatcccttt    1020
```

```
gcccccgact ggccgctcgc cgagttgggc ttcgcctggc tggcgggcga actggatggc    1080
gccggggtgg ccgagctgga ttgccgtcag ccgccgctgg gcgggttcct cgagttgcag    1140
gtgctgcccc acggcgaagg caggctggcc agcctgcggg tccgtcgcga ccatgacgga    1200
acgctggccg ggcgcttgct cgacgcctgg gtcgaatgcc tggaaagcat cgccgccgac    1260
aggcaactgc cactgccgg gctgccgttg atcggcgcgg ccgagcgcga gcgctaccag    1320
gcctggcagg gcgagcgcgt ggagcccgcg ccggtggaat ccctggtggc cgcgttcgat    1380
ctgcgcgccg ccctgcagcc gcaggcgccg gcgttgctgg atgcccacgg cagcctggat    1440
ttcgccacgc tgcgcgcgcg cagcgaagcg gtcgccgaag cgctgctggc tgccggcgtg    1500
cggcccggcc aggcggtggc ggtgatgacc gggcgcaacc gcgaggcgat cgtcgccctg    1560
ctcggggtga tgcgcgcggc ggcggtgtac accccggtca atccggagtt ccggcggcg    1620 cgggtggagc ggatgcgcga agcgggcggg atcgtcttcg cccttgccga tgccgagtgc    1680
gccgggcgcg cccgcgaggc cttcgccggg gcctgcctgg acctgtcgac gctgccgctt    1740
gccggcagcg gcatgagcct gccggcgccg ggcgggcgcg atgcggccta catgatcttc    1800
acctcgggca ccagcggcca gcccaaaggc gtggtggtcg agcacgccag cgcgctcaac    1860
ctgtcccagg ccctgcgcg cacggtatac gcgaacgtgg tgggcgaggg cctgcgggtg    1920
acggtcaacg cgccgttctc cttcgactcc tcgatcaagc agattctcca gttgctctcc    1980
ggccattgcc tggtcctggt gccgcaggag gtgcgcagcg atccgcagcg gatgctgggg    2040
ttcctcgaag aacggcgcat cgacgtgctc gactgcaccc cgtcgctgtt ccgcctgctg    2100
ctccaggccg gcctcgacga tgcccacccg gcgctgcccg gcgcatcct ggtaggggc    2160 gagcgcttcg acgaagcgtc ctgggaggtc gccgccggct ggcgccgctg ccaggtgttc    2220
aatctctacg gtcctaccga agccacggtg aacgccagcc tggcgcgggt cgccgagcat    2280
gcgcggccga ccatcggccg cgccctggcc aacgtcgatc tgcatgtggt cgatggcctc    2340
ggtcgtcgca agacccgtgg cgccagcggc gaactgtgga tcggcggcgc cggggtggcg    2400
cgcggctatg ccggcgacgc cggcgaggcg gccgggcgct tcgtcgagga gggctggccg    2460
ggcagcggcc gcctgtaccg cagcggcgac ctggtgcgct ggcgcgccga cggttgcctg    2520
gagttcctcg gcggatcga cgaacaggtg aagatcaacg gctaccgcat cgaactgggc    2580
gagatccgca gcgcgttgct ggaacacccg gcggtgggcg aggcggcggt actcaccgac    2640
gaggccgatg cggccgaacc gggcgcggat cgccggatcg tcgccttcgt caccgccgcc    2700
gaggagaccg cggacgagtc ctggctggaa gtcgacctgc ccagcgggca ccgggtcgcc    2760
ggactgaacc tcaacgaaac cgagtacgtc taccaggaaa tcttcgtcga cgaggtctac    2820
agccgcgacg gcatcgtcct gccgccggac gcggtggtcc tcgacgtcgg tgccaacatc    2880
ggcctgttct cgctgtacat cgccagccgc gcgccgcgcg cgcgagtggt cgccttcgag    2940
ccgctggcac cgatccgccg gcgcctggag gccaacctcg gacgctacgc accgcaggtc    3000
gaggtattcg gcatcggtct gtccgacgcc gagcgtgagg aaaccttcac ctactatccg    3060
ggctactcga ccttctccgg gatcgccgag tacgccgacg ccagcggcga acgcgacgtc    3120
atccgacgct acctgagcaa ccagggcgag gagggcgggg ccaacctgct gctggacaac    3180
atcgacgaaa tcctcgacga ccgcctgcgc gccgaagccc accgctgccg cctgcgccgc    3240
ctcgaccagg tgatcggcga actgggcctg gagcgtatcg acctgctgaa gatcgacgtg    3300
cagcgcgcgg aaatggatgt gctgctcggt ctcgacgatg cggcgctggc caaggtccgg    3360
```

```
cagatcgtcc tggaggtcca tgacaagcgc gacggtgcca ccgccggccg cgccgatgcc      3420
ttgagcgacc tgctgcgccg ccatggcttc gaggtgagca tccgtcagga cgcgctgctg      3480
gagggtaccg accgttacaa ctgctacgcg gtgcgcccgg ctatgccga gtcgctggct       3540
gagcgcatcg actggcgcgc gctcgcgccg cgccccgccg cggccctcgg cggcgagctg      3600
agcgagcagg ccctgcgtgg cttcctcgag gcgcgcctgc cggcctacat gctgccgagc      3660
cggatcgccc gggtcgaacg cctgccgctg accgccgaag gcaagctcga ccgtcgcgcg      3720
ctgttggcgg cgctggccgc cgaggcggcc gcgcagaccc tggaagcgcc ggccaatgcc      3780
accgaggcg ccctgctgga gatctggaag agcgtgctga acgcccggc gatcggcgtc        3840
agcgacaatt tcttccaggt cggcggcgac tccatccgcc tgatccagat gcaggtcatg      3900
gcgcgcgagg cggggcttgc ctttaccctg cgcgacgtgt tcaaccacca gagcatccgc      3960
gaactggcgc gcctgctggc cgctccggcg agtccggcgg atgcgctcgg gacctcggcg      4020
ccgcagtcgc tggagccgtt cgccctgttg tcggcggcgg aacgcaagcg cctgccggag      4080
gggctcgacg acgcctatcc gatgaccagc ctgcaacagg gcatgctcct gcaaagcgag      4140
gccagcggcg atccacggct gttgcacaac gtcgtcctgc acgaggtgca tggacgcctg      4200
gacggcgagt tgctggcgcg cgcctgggcg atcctgatcg gccgccacgc gatcctgcgt      4260
accggcttcg atctgcacgg tggccaggtt cccctgcaat gggtccaccc ggccacggcg      4320
gtcgccgccg aggtgccggt gcacgacctg tgtggcctcg atggggaaac acggcgcctg      4380
cgcctgcgtg cctggatcga ggaagagcag gccaccccgt tcgactggag ccgcccaccg      4440
ctggtgcgcc tcgccgcgct ggcgctggac gagcggcgct tcgccctggg cgtcgccgaa      4500
caccatagcg tgctggacgg ctggagcctg caaagcctgg tggacgagct gctggcggtc      4560
tacgccgacc ttctcgccgg tgtcgtcgcg cgggaagcgg aagcgcccgc ggtaggcttc      4620
cgcgactacg tggcgctgga gcgtgaggcc gaggccaacg ccgcctcggc gctgttctgg      4680
ctcgactacc tggccggcgc ccgctaccgg ccgttgcccg gcctggcgga ggagggaccc      4740
cggcgcatgg cggcggtccg cgtggacgtg ccggccgaca gcctgtcgcg cttgcgcgcc      4800
ctggccgaac gcagcggctt gcccttgcgt tcgttgttgc tggcggcgca tggccgagcg      4860
ttgtgccgct tcagcgatgc cgatgaagta gtcaccggct tcgtcagcca cgggcgcccc      4920
gaggagccgg gagcggaccg cctgctcggc ctgttcctga cacccctgcc gtgccggctg      4980
tcggcttccg tcgatctgct cgacagcgcc cgtcgcgcat tcgactacga gcgcgcgagc      5040
ctggaacatc ggcgccatcc gctggcggcg attcgcaggc gcaaccgcga gttgcgcctg      5100
gacagcctgt tcaacttcgt cgacttccac caggacgacg ccgcgccggc gggagtaagg      5160
cacggcggca tcctcgacca ggtggtggtg gacgtcgacg tgccgctggc ggtggacttc      5220
gaggtggccg cgagcgcct cgaggtgggc ttccagtatg ccgccggacg tttccccgcc      5280
gagcgcgccg aggcactggc cggcgcctac cgcgaggcgt gctggcgct gctcggagac       5340
ccggtgcagc cgcccgcggc ggcccaggcc gaggacagcg tggagctgcg gcgggtgctc      5400
aaggtgttgt cccgggtgct cggccggccg ctggcggccg accagggctt cgccagcgcc      5460
ggcgggcatt cgctgctggg cgtgcaggcg atcgccgaat gcgccggct gaccggcagg       5520
caactgagcc tggggctgtt gcagggcgat ccggatgccc gcgaagtggt gcgccgctgc      5580
catgccgccg acgcgccgcc gttgccgccc gccaccgagc gcgcccgggc cctgtggttg      5640
cagcgcagcg ggagcgcgca gccgcgcctg cgcctgatcg cgctgccgcc gcggggcggc      5700
aacgccggca ctttccgtgg ttgggacgcg cgcctgccgg cggacgtgga gctgctggcg      5760
```

-continued

| | |
|---|---|
| atccagtatc cggggcgcca ggaacgccag gacgagccat tcgtcaccga tgtagaggcc | 5820 |
| atgctctgtg ccatcgacga cgcgctcctg ccattgctcg accgtccgtt cgccctgatc | 5880 |
| ggcgccagcc tcggcggcat gctcgcctac gaactggcgg cacgcctgga aagcctgcac | 5940 |
| ggcctgcgcg ccaggcagtt gttcgtgatc agcagccgcg ctccggggcc ggacctggaa | 6000 |
| tacccgcgct tccatgcgat gggcgacgcc gagttgctgc gaaccctgcg cgagtacgac | 6060 |
| gtgctgccgc tggaagtgct cgacgacccg gagctgcgcg agatcagcct ggccaccctg | 6120 |
| cgcgccgatt cgcgcctggc cgccgactat cgctaccgcc cgcgcgagcc gctggccata | 6180 |
| ccgatcaccg cgatcctcgg cgagcaggac ccgggcgtct ccagggtggc catcgacggc | 6240 |
| tggcggcggc acgccagccg ctacgagctg gagaccctgg ccggcggcca ggcctggtg | 6300 |
| gtgacggcgg cggaggaggt ctgcgcgatc ctgcggcagc gcctggcgcc cgatgtgcct | 6360 |
| ggcggcgtgc cggcgaacct ggcaacctga | 6390 |

<210> SEQ ID NO 36
<211> LENGTH: 1395
<212> TYPE: DNA
<213> ORGANISM: Pseudomonas aeruginosa

<400> SEQUENCE: 36

| | |
|---|---|
| atgaacctgc gcccggtgat cgtcggcggc ggctcggccg gcatggccgc agccatcgag | 60 |
| ctggccaggc gcggggtccc ctgcgtcctc ttcgacgagg cctcgcgtcc ggcggggtg | 120 |
| gtctatcgcg gccccttgcg ggccggcgtc gatccggcct acctcggcgc gcgctacacc | 180 |
| cggatgctgg aaaaactgcg gcgcgatttc tccgcctgcg ccgggcacat cgacctgcgc | 240 |
| ctgaacagcc gcgtggtcgg tggcgacggc cagcgcctga tggtcctcga cgaggcggaa | 300 |
| cggctgcacg aggtggagta ttcgcacctg ctcctggcca ccggctgcca tgagcgcagc | 360 |
| gtgccgtttc ccgctggac cctgcccggg gtgatgctcc tcggcggcct gcaattgcag | 420 |
| atcaagagcg gcgtggtgaa gcccctgggc gatacctga tcgccggcag cggcccgctg | 480 |
| ctgccactgg tggcctgcca gctgcatgcg gccggggtac gtgtcgccgg ggtctacgag | 540 |
| gcctgcgcgt tcggccgcat ggccagggaa agcctggcgc tgctgaacaa gccgcaactg | 600 |
| ttcctcgacg gcctgagcat gctcggctat ctcaagctca acggcattcc gctgcactat | 660 |
| ggctggggcg tggtggaggc cagcggcgat ggggaactga cggaagtgac ggtagcgccc | 720 |
| tacgacgaag agtggcggcc cgacctggaa aacgcgcgac cggtgaaggc cagcaccctg | 780 |
| gcggtcggct atggcttcat cccgcgcacc cagctcagcc agcagttggg tctggagcac | 840 |
| ggcttcagcg acgacggata cctgcgcgcg gaatgcaacg tctggcagca gagcagccaa | 900 |
| ccgcacatcc acctggccgg cgacatggcg ggtatccgcg gcggcgaggc ggcgatgatc | 960 |
| ggcgggcgca tcgcggcctt gtcgatcctc ctgcaacgcg aggccatcgc gcccgccgag | 1020 |
| gccatcgaac gccgagaatc ccatctcgcc cgcctggagg cgatcaagcg cttccgcgcc | 1080 |
| ggagtcgagc gctacacccca gcgcggcgcc cgccaggtcg aactggcgcg ggccgatacg | 1140 |
| gtgatctgcc gctgcgaaca ggtcacccgt ggcgacatcg agcgcgcgct cgaacagggc | 1200 |
| gtgcaggaca tcgccgggct gaagatgcgc accgcgccg gcatgggcga ctgccagggg | 1260 |
| cggatgtgca tcggctactg cagcgatcgc ctgcgccgtg ccaccggacg ccacgacgtc | 1320 |
| ggctggctgc ggccgcgttt cccgatcgat ccgatcccgt tttccgcatt ccagaacctc | 1380 |
| ggtacggaag cctga | 1395 |

<210> SEQ ID NO 37
<211> LENGTH: 801
<212> TYPE: DNA
<213> ORGANISM: Pseudomonas aeruginosa

<400> SEQUENCE: 37

| | | | | | |
|---|---|---|---|---|---|
| atggcgtccg | cccctaagga | agaggagata | aatatgattt | attacttgat | cggagtggcg | 60 |
| ctattcatct | tcatgctgga | acagttggtt | cccggctgga | aattgcccaa | ggtgagcacc | 120 |
| tgggtggccc | gggtgatctt | cctcaacatc | gtccaggtgt | cgatcgccct | gctcgccggc | 180 |
| atcacctgga | acaaatggat | gatggggcac | agcctgctgc | acacctcgga | tgccctgcca | 240 |
| ccactgctgg | ccggcttcgc | cgcctacttc | gtcaacacct | tcgtcaccta | ctggtggcat | 300 |
| cgcgcgcgcc | acgccaacga | cacgctctgg | cggctgttcc | accagttgca | ccacgcgccg | 360 |
| caacgcatcg | aggtattcac | ctccttctac | aagcatccga | ccgagatggt | cttcaactcg | 420 |
| ctgctgggca | gcttcgtcgc | ctacgtggtg | atgggcatca | gcatcgaggc | cggcgcctac | 480 |
| tacatcatgt | tcgccgcgct | cggcgagatg | ttctaccact | cgaacctgcg | caccccgcac | 540 |
| gtcctcggct | acctgttcca | gcgcccggag | atgcaccgca | tccaccacca | gcgcgaccgt | 600 |
| cacgagtgca | actacagcga | cttcccgatc | tgggacatgt | tgttcggcac | ctacgagaac | 660 |
| ccccgccgca | tcgacgagcc | gcagggcttc | gccggcgaca | aggagcagca | gttcgtcgac | 720 |
| atgctgctgt | tccgcgacgt | gcacagcctc | cccggaaaaa | cccagcccgc | tcccgtcctg | 780 |
| gtcaagcccg | acgtcaggtg | a | | | | 801 |

<210> SEQ ID NO 38
<211> LENGTH: 20
<212> TYPE: DNA
<213> ORGANISM: Pseudomonas aeruginosa

<400> SEQUENCE: 38

| | | |
|---|---|---|
| acctgcccgg | aagggcaggt | 20 |

<210> SEQ ID NO 39
<211> LENGTH: 468
<212> TYPE: DNA
<213> ORGANISM: Pseudomonas aeruginosa

<400> SEQUENCE: 39

| | | | | | |
|---|---|---|---|---|---|
| ggggtacctg | gcacctacca | gatcgtgtag | ttgagccggt | acgagcgttc | tgtgttttat | 60 |
| gcaatccaca | tcagcgacca | gggatgctgg | ctatttgaaa | cacttcacgg | aatgacgctg | 120 |
| aaagtcttcg | cgacctcgtc | tgtcgcacct | taacgaaagc | attgcgaatc | cattaccgac | 180 |
| aggtttccaa | aagaaacccg | ggatgaaact | cctattgcct | ttcgaaaatt | ggaaacgaca | 240 |
| ggcgaacata | tgtaacgcga | aatttcaccc | tacgtataaa | caatgcgccc | agcgaatatc | 300 |
| gctcccttac | cgagcgacga | actcctgcgc | gccagcgaat | aaccgatgcc | gcgagggaaa | 360 |
| agtttctccg | gcatacctgg | agagccctct | cggaggcggc | gcatgaacgg | tcagcggtac | 420 |
| agggaaacac | ccctcgacat | cgagccgtct | gcggcgcctt | ctagagca | | 468 |